US006867323B2

(12) United States Patent
Denmark et al.

(10) Patent No.: US 6,867,323 B2
(45) Date of Patent: Mar. 15, 2005

(54) CROSS-COUPLING REACTION OF ORGANOSILICON NUCLEOPHILES

(75) Inventors: Scott E. Denmark, Champaign, IL (US); Jun Young Choi, Taejon (KR); Daniel Wehrli, Zurich (CH); Zhicai Wu, New York, NY (US); Luc Neuville, Urbana, IL (US); Weitao Pan, Urbana, IL (US); Ramzi F. Sweis, Champaign, IL (US); Zhigang Wang, Montreal (CA); Shyh-Ming Yang, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/875,777

(22) Filed: Jun. 6, 2001

(65) Prior Publication Data

US 2002/0183516 A1 Dec. 5, 2002

Related U.S. Application Data

(60) Provisional application No. 60/209,682, filed on Jun. 6, 2000.

(51) Int. Cl.[7] .............................................. C07C 67/00
(52) U.S. Cl. ........................... 560/96; 549/427; 549/80; 568/316; 568/875; 568/876; 568/648; 568/902; 585/467
(58) Field of Search ........................... 560/96; 544/427, 544/80; 568/316, 875, 876, 648, 402; 585/467

(56) References Cited

U.S. PATENT DOCUMENTS

| | | | |
|---|---|---|---|
| 4,985,565 A | 1/1991 | Baney et al. | 548/110 |
| 5,147,945 A | 9/1992 | Woodside et al. | 525/475 |
| 5,171,792 A | 12/1992 | Weber et al. | 525/326.5 |
| 5,194,649 A | 3/1993 | Okawa | 556/451 |
| 5,331,077 A | 7/1994 | Braun et al. | 528/31 |
| 5,362,896 A | 11/1994 | Ozai et al. | 556/464 |
| 5,663,397 A | 9/1997 | Yamashita et al. | 556/464 |
| 6,284,858 B1 | 9/2001 | Fujiyama et al. | 528/12 |

OTHER PUBLICATIONS

Ahmed, M. et al., "A Tripartite Asymmetric Allylboration—Silicon Tethered Alkene Ring Closing Metathesis—in situ Ring Opening Protocol for the Regiospecific Generation of Functionalized (E)–Disubstituted Homoallylic Alcohols" (Mar. 1999) Tetrahedron 55:3219–3232.
Barrett, A.G. M. et al., "Asymmetric Allylboration and Ring Closing Alkene Metathesis: A Novel Strategy for the Synthesis of Glycosphingolipids " (Published on Web Sep. 13, 2000) J. Org. Chem. 65(20):6508–6514.
Chang, S. and Grubbs, R. H., "A Simple Method To Polyhydroxylated Olefinic Molecules Using Ring–Closing Olefin Metathesis " (1997) Tetrahedron Lett. 28(27):4757–4760.

Denmark, S.E. et al., "Convergence of Mechanistic Pathways in the Palladium (O)–Catalyzed Cross–Coupling of Alkenylsilacyclobutanes and Alkylsilanols " (Published on Web Jul. 13, 2000) Org. Lett. 2(16):2491–2494.
Denmark, S.E. and Choi, J.Y.J., "Highly Stereospecific, Cross–Coupling Reactions of Alkenylsilacyclobutanes " (Jun. 1999) J. Am.Chem. Soc. 121(24)5821–5822.
Denmark, S.E. and Neuville, L., "Mild and General Cross–Coupling of (α–Alkoxyvinyl)silanols and –silyl Hydrides " (Published on Web Sep. 7, 2000) Org. Lett. 2(20):3221–3224.
Denmark, S.E. and Pan, W., "Intramolecular Hydrosilylation and Silicon–Assisted Cross–Coupling: An Efficient Route to Trisubstituted Homoallylic Alcohols " (Published on Web Dec. 14, 2000) Org. Lett. 3(1):61–64.
Denmark, S.E. and Wang, Z., "Cross–coupling of vinylpolysiloxanes with aryl iodides" (Apr. 2001) J. Organometall. Chem. 624:372–375.
Denmark, S.E. and Wang, Z., "1–Methyl–1–vinyl– and 1–Methyl–1–(prop–2–enyl)silacyclobutane: Reagents for Palladium–catalyzed Cross–Coupling Reactions of Aryl Halides" (Jul. 2000) Synthesis 7:999–1003.
Denmark, S.E. and Wang, Z., "Highly Stereoselective Hydrocarbation of Terminal Alkynes via Pt–Catalyzed Hydrosilylation/Pd–Catalyzed Cross–Coupling Reactions" (Published on Web Mar. 10, 2001) Org. Lett. 3(7):1073–1076.
Denmark, S.E. and Wehrli, D., "Highly Sterospecific, Palladium–Catalyzed Cross–Coupling of Alkenylsilanols" (Published on Web Feb. 1, 2000) Org. Lett. 2(4):565–568.
Denmark, S.E. and Wu, Z., "Synthesis of Unsymmetrical Biaryls from Arylsilacyclobutanes" (Published on Web Sep. 30, 1999) Org. Lett. 1(9):1495–1498.

(List continued on next page.)

*Primary Examiner*—Samuel Barts
(74) *Attorney, Agent, or Firm*—Greenlee, Winner and Sullivan, P.C.

(57) ABSTRACT

Improved methods for generating a —C—C— bond by cross-coupling of a transferable group with an acceptor group. The transferable group is a substituent of an organosilicon nucleophile and the acceptor group is provided as an organic electrophile. The reaction is catalyzed by a Group 10 transition metal complex (e.g., Ni, Pt or Pd), particularly by a palladium complex. Certain methods of this invention use improved organosilicon nucleophiles which are readily prepared, can give high product yields and exhibit high stereoselectivity. Methods of this invention employ activating ions such as halides, hydroxide, hydride and silyloxides. In specific embodiments, organosilicon nucleophilic reagents of this invention include siloxanes, particularly cyclic siloxanes. The combination of the cross-coupling reactions of this invention with ring-closing metathesis, hydrosilylation and intramolecular hydrosilylation reactions provide useful synthetic strategies that have wide application.

72 Claims, No Drawings

OTHER PUBLICATIONS

Denmark, S.E. and Yang, S.M., "Sequential Ring–Closing Metathesis and Silicon–Assisted Cross–Coupling Reactions: Stereocontrolled Synthesis of Highly Substituted Unsaturated Alcohols" (Published on Web May 9, 2001) Org. Lett. 3(11):1749–1752.

Hatanaka, Y. and Hiyama, T., "Alkenylfluorosilanes as Widely Applicable Substrates for the Palladium–Catalyzed Coupling of Alkenylsilane/F− Reagents with Alkenyl Iodides" (1989) J. Org. Chem. 54:268–270.

Hatanaka, Y. and Hiyama, T., "Cross–Coupling of Organosilanes with Organic Halides Mediated by Palladium Catalyst and Tris (diethylamino) sulfonium Difluorotrimethylsilicate" (1988) J. Org. Chem. 53:918–920.

Hatanaka, Y. and Hiyama, T., "Highly Selective Cross–Coupling Reactions of Organosilicon Compounds Mediated by Fluoride Ion and a Palladium Catalyst" (1991) Synlett p. 845–853.

Hantanaka, Y. et al., "A One–Pot Synthesis Of Conjugated Dienynes By Palladium–Mediated Three Component Cross– Coupling Reaction" (1989) Tetrahedron Letters 30(18):2403–2406.

Hirabayashi, K. et al., "A Facile Preparation and Cyclopropanation of 1–Alkenylsilanols"(1998) Bull. Chem. Soc. Jpn. 71(10:2409–2417.

Hirabayashi, K. et al., "A New Transformation of Silanols, Palladium–catalyzed Cross–Coupling with Organic Halides in the Presence of Silver(I) Oxide " (Jul. 1999) Org. Lett. 1(2):299–301.

Hiyama, T. "Organosilicon Compounds in Cross–coupling Reactions " (1998) Metal–Catalyzed, Cross–Coupling Reactions: Diederich, F. et al. (eds.), Wiley–VCH: Weinheim Chapter 10.

Hiyama, T. and Hatanaka, Y. "Palladium–catalyzed cross–coupling reaction of organometalloids through activation with fluoride ion" (1994) Pure Appl. Chem. 66(7):1471–1478.

Kirkland, T.A. and Grubbs, R. H., "Effects of Olefin Substitution on the Ring–Closing Metathesis of Dienes" (1997) J. Org. Chem. 62(21):7310–7318.

Mowery, M.E. and DeShong, P. "Cross–Coupling Reactions of Hypervalent Siloxane Derivatives: An Alternative to Stille and Suzuki Couplings" (Published on web Mar. 5, 1999) J. Org. Chem 64(5):1684–1688.

Tamao, K., "Palladium–Catalyzed Cross–Coupling Reactions of Alkenylalkoxysilanes with Aryl and Alkenyl Halides in the Presence of a Fluoride Ion" (1989) 30(44):6051–6054.

CROSS-COUPLING REACTION OF ORGANOSILICON NUCLEOPHILES

CROSS-REFERENCE TO RELATED APPLICATIONS

This application takes priority under 35 U.S.C. 119(e) from U.S. provisional application Ser. No. 60/209,682, filed Jun. 6, 2000 which is incorporated in its entirety by reference herein.

STATEMENT OF FEDERAL SUPPORT

This invention was funded by the United States government through a National Science Foundation grant NSF CHO 9803124 and 9500397. The United States government has certain rights in this invention.

BACKGROUND OF THE INVENTION

Metal-catalyzed, cross-coupling reactions have, in general, become an important synthetic tool for the construction of carbon-carbon bonds (Scheme 1) (1, 2).

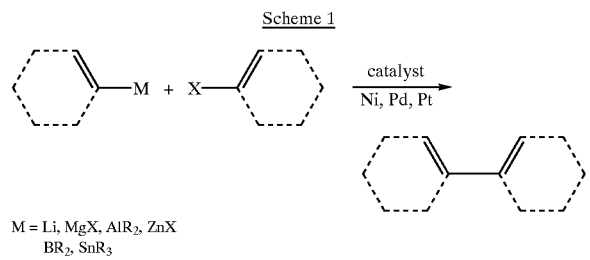

Scheme 1

M = Li, MgX, AlR$_2$, ZnX
BR$_2$, SnR$_3$

This fundamental transformation has been demonstrated to occur with a variety of organometallic nucleophiles and organic electrophiles typically catalyzed by Ni or Pd. The Suzuki coupling of organoboranes (3) and the Stille (Migita-Kosugi) coupling of organostannanes (4), for example, employ stable, isolable reagents that are extremely weak nucleophiles with good functional group compatibility. Cross-coupling reactions (1, 2) can be used, for example, to construct biaryl subunits which are a commonly found in biologically active molecules (5). Biaryl-containing compounds are also useful in the design of new compounds including organic semiconductors and liquid crystals (6). Existing methods and reagents for metal-catalyzed cross-coupling reactions, however, have some disadvantages, including attenuated and substrate-dependent reactivity, oxygen-sensitivity, high molecule weight and toxicity, which limit their utility and scope of application.

There is continuing interest in the development of new cross-coupling reactions that employ milder procedures and have broader structural generality. Desirable aspects of improved cross-coupling reactions include:(1) increased ease of preparation of the reagents (2) mildness of reaction conditions (3) stereospecificity of reaction (4) functional group compatibility and (5) tractability of by-products.

Hiyama group (7–11, 13) has reported that functionalized organosilanes: aryl and/or alkenylfluorosilanes (7–11), -fluorosiliconates (10a) and -orthosiliconates (10b, 12), do engage in cross-coupling reactions. However, these reagents are difficult to synthesize in geometrically defined form, are difficult to purify and require somewhat harsh reaction conditions for cross-coupling. Silanols (13) have also been demonstrated as appropriate coupling partners. In this reference the authors state "the coupling reaction occurred when Ag$_2$O was employed as an activator," that "several silver salts resulted in lower yields (AgOT$_f$, 21%); AgBF$_4$, 23%; AgNO$_3$, 16%) and that no reaction occurred under similar conditions when "metal oxides such as CuO, CaO, and BaO" were examined. The authors further state =We currently consider that the role of Ag$_2$O is a base to activate the organosilicon reagent."

Ideally an organosilicon reagent for use in a cross-coupling reaction will have low molecular weight, be highly effective for cross-coupling, easy to synthesize, stable under chromatographic purification conditions, easily activated toward organic electrophiles, particularly organic halides, and converted to harmless (or at least less toxic) by-products. It is further desirable that the organosilicon reagent be compatible with a variety of functional groups and exhibit stereoselectivity in reaction.

The present invention provides methods for metal-catalyzed cross-coupling and improved organometallic nucleophiles for use in such reactions.

SUMMARY OF THE INVENTION

The present invention provides improved methods for generating a —C—C— bond by cross-coupling of a transferable group with an acceptor group. The transferable group is a substituent of an organosilicon nucleophile and the acceptor group is provided as an organic electrophile. The reaction is catalyzed by a Group 10 transition metal complex (e.g., Ni, Pt or Pd), particularly by a palladium complex.

A first important aspect of this invention is the use of improved organosilicon nucleophiles which are readily prepared, and can give high product yields and exhibit high stereospecificity. A further important aspect of the invention is the activation of the organosilicon nucleophile by addition of an activation agent that provides an activating anion (e.g., a halide ion, hydroxide ion, hydride etc.). The activated organosilicon nucleophile is then reacted with the acceptor group in the presence of the palladium complex to generate the cross-coupling product.

Activation of the organosilicon nucleophile prior to contact with the acceptor group significantly decreases the formation of undesired side-products that may result from reduction of the organic electrophile. It has also been found that the amount and type of activating agent can affect the rate of the reaction. It is believed that preferred activator anions (e.g., F⁻ and OH⁻) should be capable of acting as bases to assist in the association with the metal (e.g., palladium) intermediate, but should also be capable of acting as nucleophiles to further promote the transmetallation by forming siliconate complexes.

More specifically, the invention provides improved cross-coupling reactions employing the organosilicon nucleophile of formula I wherein the silicon donor reacts with an organic electrophile (R$^3$—Y) in the presence of a palladium catalyst (M-Ln, where Ln

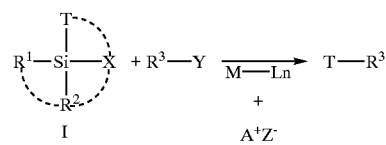

represents various ligands) to form the —C—C— coupled product (T$^3$KR), where T is a transferable group on the organosilicon nucleophile, R$^3$ is the acceptor group and Y is the leaving group of the organic electrophile (Y can be various halides, among others). The reaction is performed in the presence of an activating agent, the salt $A^+Z^-$.

The organosilicon nucleophile can contain more than one transferable group, spectator (non-transferred) groups (e.g., $R^1$ or $R^2$) and other functional groups X, which may be covalently linked to each other as indicated by dashed lines in formula I.

In a preferred embodiment, the organo silicon nucleophile is activated with the activating agent prior to reaction with the organic electrophile. The reaction is typically carried out in an appropriate solvent including, among others, polar aprotic solvents, for example, ethers, THF (tetrahydrofuran), DMF (dimethylformamide), $CH_3CN$, TBME (t-butylmethylether) or mixtures thereof.

The transferable group (T) can be selected from aromatic (including aryl and substituted aryl), substituted aromatic, heteroaromatic, olefinic, substituted olefinic, allylic, substituted allylic, acetylenic, substituted acetylenic, allenic, substituted allenic, an acyl group, and an alkyl including: cycloalkyl and heterocycloalkyl groups, and substituted alkyl groups, including perfluoralkyl groups. T groups can also contain one or more substituents (R's) that are protected from reaction during the cross-coupling reaction by an appropriate protective group, as is understood in the art.

T groups specifically include, cyclopropyl groups, epoxy groups, vinyl groups, propenyl groups, butenyl groups, pentenyl groups, hexenyl groups, heptenyl groups, acetylenic groups, propargyl groups, aryl-substituted alkenyl groups, phenyl groups, naphthyl groups, thienyl, pyridinyl groups or acyl groups. All T groups can be substituted with one or more non-hydrogen substituents (R's), which can include among others halides, CN, and $NO_2$ groups.

$R^3$ is an acceptor group to which T will be coupled and which can be an aromatic, substituted aromatic, heteroaromatic, olefinic, substituted olefinic, allylic, substituted allylic, acetylenic, substituted acetylenic, allenic, substituted allenic, alkyl, and substituted alkyl groups. Y is any leaving group that will not otherwise interfere with the reaction, including among others: I, Br, Cl, OTf (triflate), OTs (tosyl), nonaflate, phosphates, iodonium ions, or $N_2^+$. Preferred leaving groups are I and Br. The acceptor group can carry one or more non-hydrogen substituents (Rs) which can include electron withdrawing groups and electron donating groups.

M-Ln is a Group 10 metal complex, where Ln can represent the presence of one or more ligands. Preferred metal complexes are palladium complexes which can have 2–4 ligands/Pd. The catalyst can contain more than one palladium and have ligands bridging the palladiums. Ln can be organic groups or halides or mixtures of organic groups and halides. Palladium catalyst include, among others, $Pd(dba)_2$; $Pd_2(dba)_3$·solvent; $[Pd(allyl)Cl]_2$; $PdCl_2$; $Pd(OAc)_2$; $Pd(OTFA)_2$; $(Ph_3P)_4Pd$; $(Ph_3P)_2PdCl_2$; (COD) $PdBr_2$; $Pd(OTf)_2$; $(PhCN)_2PdCl_2$; and $(Ph_3P)_2PdBrCl$. Preferred Pd catalysts are $Pd(dba)_2$; $Pd_2(dba)_3$·solvent; and $[Pd(allyl)Cl]_2$ (dba is dibenzylidene acetone, OAc is acetate, OTFA is trifluoracetate, Ph is phenyl, COD is 1,4-cyclooctadiene, and OTf is triflate.) M-Ln can be prepared and added to a reaction or prepared in situ by separate addition of a stable organic source of the metal, e.g. a stable organic source of palladium, and a selected ligand or mixture of ligands.

The activity of a given catalyst for the cross-coupling reaction of this invention may in some cases be enhanced by addition of an additive, such as CuI or other additives that have been shown to enhance coupling reactions such as the Stille Coupling reaction.

The activating agent $A^+Z^-$ for activating the organosilicon nucleophile is an anion source. Preferred anions are those that can function as a base as well as a nucleophile. Anions include $F^-$, $OH^-$, $CN^-$, $N_3^-$, $HF_2^-$, $H_2F_3^-$, $H^-$, $RO^-$, where R is an alkyl or aromatic (including an aryl) group, $(R)_3SiF_2^-$ where different R's in the same anion can be the same or different and are alkyl groups or aromatic (including aryl) groups, e.g., $(CH_3)_3SiF_2$—, $(Ph)_3SiF_2^-$; and $(R)_3Si$—O. Anions can be provided as salts with any appropriate cation. Cations include $K^+$, $Na^+$, $R_4N^-$, $Cs^+$, $(R_2N)_3S^+$ (where R is aliphatic). The cation is typically selected to facilitate solubility of the activating agent in the selected reaction solvent.

In a specific embodiment, the cross-coupling reaction is performed free of fluoride ion. In this embodiment, the preferred activating agent is a base such as hydride ($H^-$) or a silanolate anion $((R)_3$—Si—$O^-)$. Fluorine-free cross-coupling is preferred for use with coupling substrates (T or $R^3$—Y) which contain silyl protective groups. The use of activating anions that are not fluorine expands the utility of the cross-coupling reaction to allow the use of silyl protective groups. The preferred organosilicon nucleophiles for use in fluoride-free cross-coupling are organosilanols.

In a specific embodiment, the invention provides a method for generating biaryl moieties in the cross-coupling reaction. In this case, T and $R^3$ are aryl groups or substituted aryl groups. In another specific embodiment, the invention provides a method for generating dienes in the cross-coupling reaction. In this case, T and $R^3$ are olefinic groups or substituted olefinic groups.

The cross-coupling reaction of this invention is compatible with a number of other reactions which can be used to form organosilicon nucleophiles that can then participate in the cross-coupling reaction. In certain cases, the reagents for the cross-coupling reaction can be combined with those for generating the organosilicon nucleophile, so that a one-pot protocol can be employed to generate desired cross-coupling products.

For example, the formal addition of an aryl-H or alkenyl-H bond across a terminal alkyne can be accomplished in a single reaction vessel by combination of a platinum-catalyzed hydrosilyation followed by the cross-coupling reaction of this invention. Highly stereoselective conversion of homopropargyl alchols to trisubstituted homoallylic alcohols can be achieved in a one-pot reaction by coupling of alkylidenesilacycloakanes formed from intramolecular hydrosilyation of homopropargyl alcohols.

The cross-coupling reaction of this invention can be combined with ring-closing metathesis of silylvinyl ethers to generate unsaturated alcohols (e.g., diene alcohols or styrene alcohols).

The present invention also provides improved organosilicon reagents for use in metal-catalyzed cross-coupling reactions. The reagents are alkenyl- or aryl-substituted silanes or siloxanes which are highly effective for cross-coupling, compatible with a wide range of functional groups, and which provide generally high reaction yields and stereoselectiveness.

Organosilicon reagents include those of formula I:

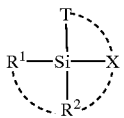

I where T is a transferable group as described above; $R^1$ and $R^2$ are spectator groups (non-transferred) which can be selected from alkyl or substituted alkyl groups or groups containing —O—Si—, particularly groups containing one or more —O—Si($R_A$ $R_B$)— groups and —O—Si—($R_A$ $R_B$ $R_C$) groups or one or both of $R^1$ and $R^2$ can be transferable groups (T). $R_A$, $R_B$, and $R_C$, independently, can be spectator groups, functional groups (X), or transferable groups (T), including halides, OH, alkyl or aromatic groups which are optionally substituted, silane groups or siloxane groups.

X is a functional group which can be selected from a halide, OH, H, N(R')$_2$ group where R' is hydrogen, an alkyl group or a substituted alkyl group, or a group containing —O—Si—. X can also be a transferable group. If $R^1$, $R^2$ or X is a transferable group, it is preferred that it is the same group as T. The organosilicon reagent can contain up to three transferable groups substituted onto each Si in the reagent. Two of $R^1$, $R^2$ and X can be covalently linked to each other to form a cyclic alkyl, substituted cyclic alkyl group or cyclic siloxane; T groups include olefinic aromatic, allylic, acetylenic, allenic, and alkyl groups that are in turn substituted with silane or siloxane groups.

In specific embodiments, $R^1$ and $R^2$ groups are spectator groups that are alkyl groups: including straight-chain, branched and cyclic alkyl groups that are optionally substituted. Preferred alkyl groups are those that have from 1 to about 6 carbon atoms. Substituents for alkyl $R^1$ and $R^2$ groups include, among others, halogens, R", COR", COOR", N(R")$_2$, OR" groups (where R" is H, an alkyl group or an aromatic group), and SR where R is an alkyl group or an aromatic group, nitro groups, or nitrile groups. Substituents on $R^1$ and $R^2$ groups are preferably non-reactive under the conditions of the cross-coupling reaction and do not significantly interfere with the desired cross-coupling reaction. Reactive $R^1$ and $R^2$ groups may be protected using conventional protective groups. $R^1$ and $R^2$ may be covalently linked together to form cyclic moieties, e.g., 3- to 6-member rings.

In other specific embodiments, one or both of $R^1$ and $R^2$ are silane or siloxane groups. Silane groups include, among others, —Si($R_A$ $R_B$ $R_C$) groups where $R_A$, $R_B$, and $R_C$ independently are H, halide, or optionally substituted alkyl or aromatic groups. $R_A$, $R_B$, and $R_C$ can also be any X or T groups.

For X that are alkyl, olefinic, acetylenic, or aryl, preferred substituents are halides, OH, R COOR, OR (where R is alkyl or aromatic), nitro groups, or nitrile groups. For X that are OR or N(R)$_2$ groups preferred substituents on the R groups are halides.

In a specific embodiment, $R^1$ and $R^2$ may together form a cyclic group:

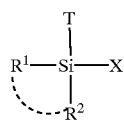

II where X is as defined above, but is preferably a halogen, particularly F or Cl, OH, OR (where R is an optionally a substituted alkyl or aromatic group) or NRR' (where R or R', independently, are H or an optionally substituted alkyl or aromatic group). In a more specific embodiment, $R^1$ and $R^2$ may together form a silacycloalkyl group, such as

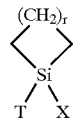

II-1 where T and X are as defined above and r is an integer ranging from 1 to about 4. In preferred organosilanes of formula II-1, X is a halogen, particularly F or Cl, OH, OR (where R is an optionally a substituted alkyl or aromatic group) and NRR' (where R or R', independently, are H or an optionally substituted alkyl or aromatic group). In preferred organosilanes, r is 1 (silylcyclobutanes), such as

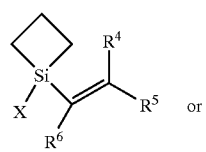

II-2

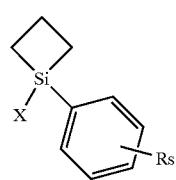

II-3 where X is as defined above and $R^{4-6}$ can be H, alkyl (linear, branched and cyclic), alkenyl, aromatic (aryl), heterocyclic, heteroaromatic any of which may be substituted with Rs groups including halides, alkyls, alkoxy groups, OH, CN, NO$_2$, among others. Two or more of $R^{4-6}$ can be covalently linked. In formula II-3, Rs can be, among others, any electron withdrawing or electron donating groups.

In another specific embodiment, $R^1$ and $R^2$ are alkyl groups or substituted alkyl groups having from 1 to about 20 carbon atoms, and preferably having from 1 to about 10 carbon atoms, X is a halide and T is as defined above. Preferred halides are fluorine and chlorine. Preferred substituents for $R^1$ and $R^2$ alkyl groups are halides. In other specific embodiments, $R^1$ and $R^2$ are alkyl groups or substituted alkyl groups having from 1 to about 20 carbon atoms, and preferably having from 1 to about 10 carbon atoms, T is as defined above and X is OH or H.

Organosilicon reagents of this invention include silanols and silyl hydrides (where x is H or OH) and particularly silanols of formulas III-1:

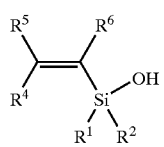

III-1 as well as (α-alkoxyvinyl)silanols of formula III-2 and cyclic (α-alkoxyvinyl)silanols of formulas III-3 and III-4:

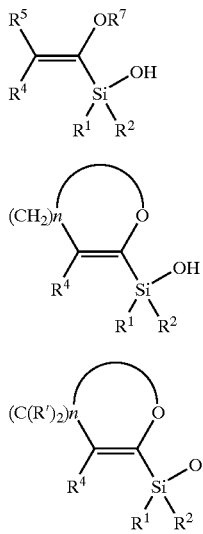

Organosilicon reagents can also be hydrides of formulas IV-1, IV-2, IV-3 and IV-4:

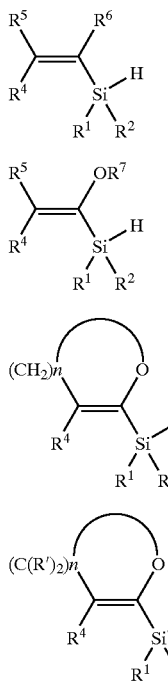

where $R^{1-2}$, $R^{4-6}$ are as defined above, $R^7$ is hydrogen, alkyl (linear, branched or cyclic), alkenyl, aromatic (aryl), heterocyclic, heteroaromatic any of which may be substituted with non-hydrogen substituents (Rs) and R' can be the same or different groups in the same compound and are selected from H, alkyl, alkenyl or aromatic each of which can be substituted with one or more non-hydrogen substituents Rs. $R^5$ or $R^4$ or both may be covalently linked to $R^7$. In III-3, n is an integer which is preferably 2–4, inclusive.

where variables are defined as for compounds of Formula III-1–III-4 above.

Organosilicon reagents of this invention can also be cyclic silyl ethers (compounds of Formula I in which T and X groups are covalently linked. Exemplary cyclic silyl ethers include:

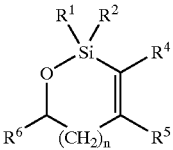

where variables $R^{1-2}$, $R^{4-6}$ are defined as above and may also be any Rs as above and n is zero or an integer, preferably n ranges from 0–3, inclusive, and more preferably n=1 and

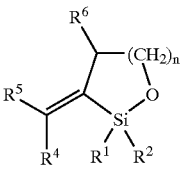

where variables $R^{1-2}$, $R^{4-6}$ are defined as above and may also be any Rs as above and n is an integer, preferably n ranges from 1–4, inclusive and more preferably n=1 or 2. In formulas V-1 and V-2 ring positions other than those indicated may be substituted with $R^{4-6}$ groups or Rs.

Organosilicon reagents of this invention also include siloxanes, such as those of formula I above where T is a transferably group and X, $R^1$ or $R^2$ are as defined above and at least one of X, $R^1$ or $R^2$ contains an —O—Si($R_A$ $R_B$)— group (where $R_A$ and $R_B$, independently can be optionally substituted alkyl or aromatic groups or X functional groups). One or more of X, $R^1$, $R^2$, $R_A$ or $R_B$ can also be a transferrable group. Useful siloxane reagents include linear (VI-L) branched (VI-B) or cyclic (VI-C) siloxanes, e.g., of formulas:

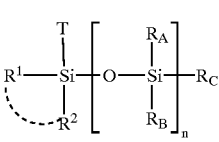

where $R_A$–$R_C$ can be any of the $R^1$, $R^2$, X or T groups defined above and n is an integer greater than or equal to 1. $R_A$ and $R_B$ groups on different Si atoms may be the same or different. Any pair of $R^1$, $R^2$, $R_A$, $R_B$ or $R_C$ can be optionally covalently linked;

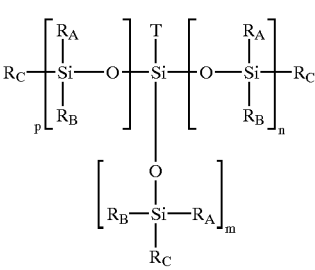

where $R_A$–$R_C$ can be the same or different on different Si and can be any of the $R^1$, $R^2$, X or T groups defined above m, n and p are 0 or integers greater than or equal to 1 and two of m, n or p are 1 or more. Any pair of $R_A$, $R_B$ and $R_C$ groups can be optionally covalently linked; or

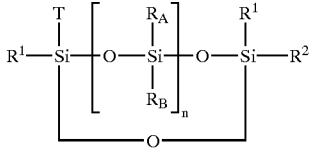

VI-C where $R_A$ and $R_B$ can be the same or different on different Si and can be any of the $R^1$, $R^2$, X or T groups defined above and n is an integer greater than or equal to 1. $R_A$ and $R_B$ and/or $R^1$ and $R^2$ groups are optionally covalently linked.

Linear siloxanes include disiloxanes, trisiloxanes and higher siloxanes and include siloxanes of formula:

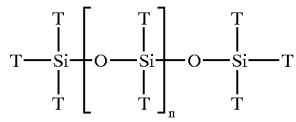

VI-L-2 where n is 0 or an integer greater than or equal to 1 and all T are the same transferrable group, e.g., an olefin or aryl group or the linear siloxane:

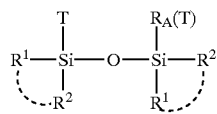

V-L-3 where any or all of $R^1$, $R^2$ and $R_A$ can be T.

Branched siloxanes include:

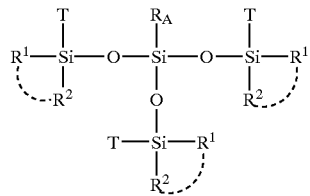

VI-B-2 where all T are the same transferable group. The formula illustrates optionally covalent linkage of $R^1$ and $R^2$ groups on the same silicon atom. $R^1$ and $R^2$ groups from different silicon atoms can optionally be covalently linked as well.

Cyclic siloxanes include:

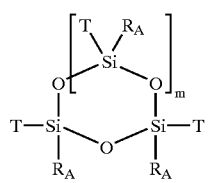

VI-C-2 where all of T are the same transferable group, m is an integer ranging from 1–4, which is preferably 1 or 2, and $R_A$ can be any of $R^1$, $R^2$, X or T groups as defined above.

In another specific embodiment, the invention provides a method for making —C—C— bonds which employs a bis-silyl reagent of formula (VII-1):

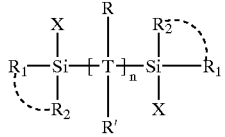

VII-1 where T is a transferrable group or groups linked between two silicon atoms, n is an integer greater than or equal to 1, X, $R^1$ and $R^2$ are as defined above and may be the same or different on different Si atoms. R and R' are optional substituents on the T groups and can take any of the values of $R^1$, $R^2$ or X. In preferred reagents of formula VII-1, X is OH, H, F or OR (where R is an alkyl or substituted alkyl groups). The product of the reaction employing reagent VII-1 contains two $R^3$ groups:

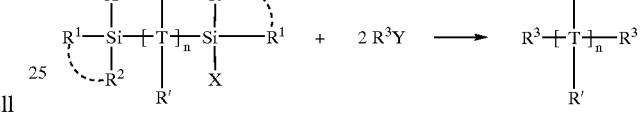

The transferable group is inserted between two $R^3$ groups. In preferred reagents of formula VII-1 T is an optionally substituted olefin and when n is 2 the transferable group is an optionally substituted diene. The transferable group may also be a non-conjugated diene or a group containing more than two double bonds. This type of organosilicon reagent is particularly useful for the synthesis of stilbenes.

The invention also provides reagent kits which combine a selected organosilicon nucleophile of formula I (and all other formulas illustrated above) carrying a selected transferable group T with an activating agent $A^+Z^-$ and optionally also contains a catalysts which may be provided as a stable organic source of the Group 10 metal in combination with a selected ligand or mixture of ligands. Preferably, the catalyst and activating agent are selected to facilitate the cross-coupling of the organosilicon reagent included in the kit and may be optimized for use with a choice of organic electrophiles. The kit may further include instructions for carrying out the reaction. The kit may also provide appropriate solvent and/or an appropriate reaction vessel for carrying out the reaction. In preferred embodiments, kits of this invention comprise an organosilicon cross-coupling reagent that is a silacyclobutane, a siloxane (linear, cyclic or branched) or a bis-silyl compound.

DETAILED DESCRIPTION OF THE INVENTION

Definitions

The term silane is used herein to refer to subsets of organosilicon cross-coupling reagents which can contain one or more silicon atoms, but do not contain —Si—O—Si— linkages. The term siloxanes is used to refer to subsets of organosilicon cross coupling reagents having one or more —Si—O—Si— linkages.

The term aliphatic refers to groups that are saturated hydrocarbons and includes alkyl, substituted alkyl, and alicyclic (cyclic alkyl) groups. Alkyl groups include lower alkyl groups (having 1–6 carbon atoms), intermediate length alkyls (having 7–20 carbon atoms) and higher alkyl groups (having over 20 carbon atoms). Alkyl groups may be branched, straight-chain (linear) or cyclic. Cyclic alkyl groups can include cyclopropyl, cyclobutyl, cyclopentyl, or cyclohexyl groups, among others. Alkyl groups include those that have portions that are linear or branched combined with cyclic portions (e.g., methylcyclohexyl-). Alkyl groups include monocyclic species (e.g., cyclopropyl) as well as bicyclic groups (e.g., norbornyl).

The term aromatic (or aryl) is used generally herein to refer to groups that contain one or more aromatic rings which may be fused rings or non-fused rings or a combination of fused and non-fused rings. Aromatic rings can be 5- or 6-member rings. Aromatic groups include, among others, phenyl groups, substituted phenyl groups, naphthyl groups, substituted naphthyl groups, biphenyl groups, substituted biphenyl groups, phenanthrene and substituted phenanthrene groups.

The term heteroaromatic is used generally herein to refer to groups that contain one or more aromatic rings containing one or more non-carbon ring atoms (e.g., N, S or O). Heteroaromatic rings can be 5- or 6-member rings and can include species that have more than one aromatic ring that may be fused or non-fused. Heteroaromatic groups include among others: pyrroles, furans, thiophenes, pyridine, diazines, pyrolidines, pyrimidines, quinolines, isoquinolines, indoles, benzofarans, benzothiophenes, each of which may be substituted.

The term olefinic (or alkenyl) is used broadly herein to refer to organic groups having one or more double bonds, which may or may not be conjugated. Olefinic groups include, among others: $R^A R^B$—C=C—$R^C$— where $R^{A-C}$ can be various aliphatic, or aromatic groups with various substituents. For example, olefinic groups include $R^A R^B$—C=C—$R^C$—, where $R^{A-C}$ independently, can be hydrogen, alkyl or aryl groups (which may be substituted) and particularly, include those where $R^A$ and $R^B$ are alkyl or aryl groups (which may be substituted) and $R^C$ is hydrogen. Alkenyl groups can include linear alkenes, branched alkenes or cyclic alkenes (e.g., cyclohexenyl). The term "diene" refers to groups that have two double bonds which may be conjugated (e.g., —HC=CH—CH=CH—) or non-conjugated (e.g., —CH=CH—CH$_2$—CH$_2$—CH=CH—). The term "polyenes" refers generally to any group that contains more than one double bond. Allylic species are groups having the structure $R^A R^B$—C=C—$R_C$—$CR^D R^E$—, where $R^{A-E}$ can be various aliphatic, or aromatic groups with various substituents. Allylic species include $R^A R^B$C=$CR^C CR^D R^E$—, where $R^{A-E}$, independently, are hydrogen, alkyl or aryl groups and particularly include groups where $R^A$ and $R^B$ are alkyl or aryl groups and $R^{C-E}$ are hydrogens. Allenic species are groups having the structure: $R^A R^B$—C=C=C—$R^C$—, where $R^{A-C}$ can be various aliphatic or aromatic groups that may be substituted. Allenic groups include $R^A R^B$—C=C=C—$R^C$—, where $R^{A-C}$, independently, are hydrogen, alkyl or aryl groups and particularly the groups where $R_A$ and $R^B$ are alkyl or aryl groups and $R_{C-E}$ are hydrogens.

The term alkynyl is used broadly herein to refer to organic groups having one or more triple bonds, which may or may not be conjugated. The term acetylenic refers to groups having the structure $R^A$—C≡C— where $R^A$ can be a variety of alkyl, substituted alkyl, aryl or substituted aryl groups. A terminal alkyne has the structure $R^A$—C≡CH where $R^A$ can be various aliphatic or aromatic groups that may be substituted with one or more non-hydrogen substituents (Rs).

The term substituent as used in reference to various groups (e.g., substituted alkyl or substituted aromatic) is used broadly herein to refer to the introduction of various non-hydrogen substituents (generally Rs) into the named group. A substituent can replace a H in a given named group, it may replace a —CH$_2$— group in a straight-chain, branched or cyclic alkyl moiety, or it may replace a ring carbon in an aromatic or aryl compound. Preferred substituents include halides, CN—, NO$_2$—, OH—, SH—, N(R)$_2$ groups where R is a hydrogen, an alkyl or aryl group, or a substituted alkyl or substituted aryl group; an SR group where R is an alkyl or aryl group, or a substituted alkyl or substituted aryl group; an acyl group, or an RO—, ROCO$_2$— or RCO— group where R is an alkyl, aryl, substituted alkyl or substituted aryl group. For example, one or more non-neighboring —CH$_2$— groups in any named group may be substituted with an —O— (to give an ether group), —S— (to give a thioether group), NH or NR (where R is alkyl)(to give an amine group), —NH—CO— (to give an amide group), C=O (to give a ketone group), and —O—C=O (to give an ester group).

Substituents are preferably non-reactive under the cross-coupling reaction conditions applied. However, reactive substituents can be accommodated if protected with protecting groups, as is known in the art.

The reactions of this invention are conducted in a solvent. The solvent is preferably chosen to provide a substantially homogeneous reaction mixture to maintain reactants, activator and catalyst substantially in solution to facilitate reaction. Preferred solvents are polar aprotic solvents, including ethers, DMF, THF, CH$_3$CN, TBME and mixtures thereof, which facilitate the cross-coupling reaction.

Cross-coupling reaction can generally be carried out at temperatures ranging from sub-ambient to ambient to the temperature of refluxing solvent. It is preferred that the reaction be carried out at the lowest temperature possible without cooling (most preferably at ambient room temperature) to minimize energy costs of reaction and to avoid unnecessary decomposition of reactants, catalyst or activator.

As illustrated herein, reaction rates and yield of the desired product can be affected by the relative amounts of reagents and activator present in the reaction mixture. In general, in the cross-coupling reactions of this invention, the organosilicon nucleophile is preferably provided in excess (in molar equivalents) over the organic electrophile. The organosilicon nucleophile is preferably employed at more than 1 up to about 2 equivalents. A more preferred range for the organosilicon nucleophile is from about 1 to about 1.5 equivalents and a more preferred range is from about 1.1 to about 1.2 equivalents. The activator, also in general, is preferably provided in excess over the organosilicon nucleophile, at a level of at least about 5% or more equivalents of the organosilicon nucleophile. As discussed below, it was found that the desired coupling reaction was significantly facilitated by the use of a larger excess of the activator. Thus, in preferred embodiments the activator is present in the reaction mixture at levels of 2 to 3 times (in equivalents) of that of the organosilicon nucleophile. A preferred range for the activator is from about 2 to about 4.5 equivalents (based on the organic electrophile).

Reaction products can generally be isolated and purified by methods well-known in the art. It was found that the desired coupling reaction products, which were, in general, rather nonpolar, could be removed from siloxane by-products by initial silica gel plug filtration of the reaction mixture, followed by reversed-phase chromatography which was followed by distillation. Coupling reaction products that are solids may be further purified by recrystalization or other methods known in the art.

Organosilicon nucleophiles of this invention can be readily prepared by methods illustrated herein or by routine modification or adaptation of those methods in view of what is generally known in the art and what is specifically described herein. A variety of organosilicon compounds suitable for use as nucleophiles in this invention are commercially available.

A variety of organic electrophiles, catalysts, particularly Pd catalysts, ligands, and activator salts useful in the reactions of this invention are commercially available or readily synthesized using methods disclosed herein or that are well-known in the art.

As illustrated herein, reaction conditions can be readily optimized for a given organosilicon nucleophile, organic electrophile, activator, or catalyst in view of the teachings herein and what is generally known in the art.

The invention also provides reagent kits which combine an organosilicon nucleophile of this invention with an activating agent and optionally also a catalyst. The kit may contain components in relative amounts optimal for carrying out a selected coupling reaction with the organosilicon reagent provided in the kit.

Alkenylsilacycloalkanes

The methods of this invention that employ alkenylsilacycloakanes are illustrated by examining the coupling of (E)- and (Z)-1-(1-heptenyl)-1-methysilacyclobutane ((E)-21 and (Z)-21) with a variety of electrophiles. These substrates are readily prepared in high yield and geometrical purity (with the E/Z ratios determined by GC analysis, see below) as shown in Scheme 2. Because of the enhanced electrophilicity of 1-chloro-1-methylsilacyclobutane, the intermediate vinylalane obtained by hydroalumination of 1-heptyne reacted in good yield to afford (E)-21 in >99/1 isomeric purity. The corresponding (Z)-21 isomer was prepared by adaptation of related literature procedures (14). Although 1-chloro-1-methylsilacyclobutane is commercially available (Gelest Inc. or Aldrich), it can be prepared in large quantities by Wurtz coupling of dichloro(3-chloropropyl)methylsilane (15, 16).

First, a survey of many palladium catalysts showed a dramatic influence on reaction rate in the following order: $Pd(dba)_2 \sim Pd_2(dba)_3 > [allylPdCl]_2 > Pd(OAc)_2 \sim Pd(OTf)_2 > (COD)PdBr_2 > (PhCN)_2PdCl_2 \sim (Ph_3P)_2PdCl_2 \sim (Ph_3P)_2BnPdCl$ for alkenyl iodides. The order may be different for other reactants.

Second, the nature and amount of the fluoride source was also found to be important. TBAF (tetrabutylammonium fluoride) was found to be effective with the alkenylsilacycloalkanes; however, neither $(Me_2N)_3S^+$, $Me_3SiF_2^-$ (TASF) nor KF gave coupling products in the reactions examined with these reagents. The corresponding TBA-OR (where R is alkyl, e.g., methyl) or related tetraalkylammonium fluorides or alkoxides can also be used with these nucleophiles. Also, the reactions displayed a strange rate profile. With 1.5 equiv of TBAF, initial rates were fast (nearly 80% conversion in 10 min, but the reactions required another 8–9 h to go to completion ($^1$H NMR analysis). Thus, by simply employing additional TBAF (e.g., 3 equiv.), the reactions proceeded rapidly to completion within minutes. In view of the teachings herein, the amount of activating agent (e.g., TBAF, TMAF (tetramethylammonium fluoride) or tetraalkylammonium hydroxide or -alkoxide) can be readily optimized for a given cross-coupling reaction.

Finally, the order of mixing of the reagents is important for achieving high yields and reproducible reactions. Specifically, premixing of the silacyclobutane and activating agent eliminated the formation of reduction by-products with many of the Pd catalysts. Thus, specifically for the silacyclobutane reagents, the preferred reaction protocol employs 1.1–1.2 equiv of 21, 3.0 equiv of TBAF (1.0 M in THF as solvent), and 5 mol % $Pd(dba)_2$. The reactions are preferably run at ambient (RT) temperatures.

Stereoselectivity and synthetic generality of the process were investigated in coupling reactions of (E)- and (Z)-21 with aryl iodides (Table 1). For all substrates examined, the reactions were highly stereospecific (see E/Z ratio). Moreover, both electron-deficient (entries 7 and 8) arenes and electron rich (entries 9 and 10) arenes reacted rapidly and in high yield. To achieve such high yields of analytically pure materials, a purification protocol was needed to remove the siloxane by-products from the rather non-polar coupling products. Thus, the styrenes 22a–22e (where the identifiy of the Aryl group is listed in Table 1) were all purified by silica gel plug filtration, C-18 reversed-phase chromatography (MeOH/$H_2O$), and distillation.

Alkenyl halides are excellent partners in $sp^2/sp^2$ couplings with 21. The results of Pd-catalyzed coupling with alkenyl iodides and bromides under identical reaction conditions to give dienes 24 and 26 (minor amounts) are collected in Table 2. As in the alkenyl/aryl couplings these reactions were also highly stereospecific even for the production of (Z,Z)-24c (entry 7). The reactions proceeded smoothly at room temperature, though for β-bromostyrene, [allylPdCl]$_2$ gave the best results. Moreover, the free OH$^-$ group in (E)- or (Z)-6-iodo-5-hexenol did not interfere with the coupling. In all cases a minor byproduct of cine substitution 26 was detected which presumably arose from a Heck type process previously documented in organoborane (3)/organostannane couplings (17). However, with α-bromostyrene (E)-28, (E)-21coupled in high yield to give (E)-30 and without a trace of the regioisomer (Scheme 3).

Arylsilacycloalkanes

Initial studies of the cross-coupling reaction of methyl-(phenyl)silacyclobutane with either aryl or alkenyl iodides gave no desired products under various conditions, including those optimized for alkenylsilacyclobutanes. The reactivity of the arylsilacyclobutanes was enhanced by introducing a heteroatom on the silicon. Chlorosilane 40 and fluorosilane 42 were prepared in a straightforward fashion from dichlorosilacyclobutane (38) (available from Aldrich or Gelest Inc.), Scheme 4.

Orienting experiments with 42 and iodobenzene revealed that under standard coupling conditions (TBAF/Pd(dba)$_2$/ THF/RT, see 18) 25% conversion could be obtained in 48 hours. Screening different Pd sources identified [allylPdCl]$_2$ as the superior catalyst in terms of rate and amount of side reaction. With this catalyst, fluorosilane 42 was found to be more reactive than chlorosilane 40 and thus was used to optimize the other reaction variables.

Careful investigation of the reaction between 42 and iodobenzene showed that homocoupling of both these substrates (to generate 45 or 46, for example) was a serious liability (entry 1, Table 3) (11, 19). Where no ligand was added both possible homocoupling products 45 and 46 were observed. To facilitate the transmetallation and eliminate the homocoupling, various additives were surveyed with ratio of ligand/palladium of 2.0. The additives examined (Table 3) cover a wide range of donor properties and steric bulk. While (o-tol)$_3$P (entry 2), ($C_6F_5$)$_3$P (entry 3), and phosphite 48 (entry 9) suppressed the desired coupling, the other ligands such as tri(2-furyl)-phosphine (entry 4) and triphenylarsine (entry 5) and the bulky ligands such as tri(tert-butyl)phosphine (entry 6) (20) and tricyclohexylphosphine (entry 7) were effective in eliminating the homocoupling of arylsilanes and significantly suppressing the homocoupling of aryl iodides. Nevertheless, the desired cross-coupling was still rather sluggish. It was surprising that recently introduced ligand 47 (entry 8) did not inhibit the generation of 45 (21).

To accelerate the cross-coupling process, the reaction temperature was increased to 50° C. Again, a variety of ligands were surveyed, and the results are collected in Table 4. With the exception of $P(C_6F_5)_3$ (entry 2) and DMPE (entry 5), all the other ligands allowed the reaction to be complete in 24 hours. As is evident from Table 5, the ligands have a dramatic effect on the generation of homocoupling product 45. Tri(tert-butyl)phosphine was the best ligand to suppress this side reaction; only 6% of 45 was produced (Table 4, entry 7).

To further reduce the amount of 45, the ligand/Pd ratio was examined with most effective additive tri(tert-butyl) phosphine. As is apparent from Table 5, the more ligand added, the less 45 generated. However, the desired cross-coupling reaction was also retarded by the ligand. When the ligand/Pd ratio was over about 4.2, the reaction was not complete in 22 hours. Thus, the preferred ratio of (tert-Bu)$_3$P/Pd is about 2.0 for the coupling of fluorosilane 42 with aryl iodides at 50° C.

Preliminary studies found fluorosilane 42 to be superior to chlorosilacyclobutane 40 in the cross-coupling reaction. Under the identical conditions noted above in Table 5 (THF/50° C.), the reaction with the chlorosilacyclobutane 40 was not complete within 22 hours. By carrying out the reaction in refluxing THF, complete conversion could be observed within 16 hours (Table 6). However, at the elevated temperature, the amount of side product 45 increased to 11% with a (t-Bu)$_3$P/Pd ratio of 2.2. The amount of 45 can be reduced to less than 5% when the ratio of P(t-Bu)$_3$/Pd is increased to 4.0.

From the foregoing studies it is apparent that both chlorosilane 40 and fluorosilane 42 are appropriate partners for the cross-coupling with aryl iodides. The fluorosilane is more reactive and can perform the coupling at slightly lower temperature and with less additive. On the other hand, the chlorosilane can be easily prepared in one step.

Optimized conditions were established as follows for reaction of the chlorosilane 40: pre-treatment of 40 with TBAF (3.0 equiv), [allylPdCl]$_2^-$ (2.5 mol %) as catalyst, and tri(tert-butyl)phosphine (20 mol %) as ligand in refluxing THF. The reactions with a variety of aryl iodides bearing electron-withdrawing or -donating groups in the para, meta, or ortho positions were investigated to show the generality of the electrophilic component (Table 7). The desired unsymmetrical biaryls were obtained in good to excellent yields within several hours for all the aryl iodides tested. The mild reaction conditions are compatible with a wide range of functional groups including carbethoxy (entry 2), acetyl (entry 3), nitro (entry 4), and cyano (entry 5). It is noteworthy that even though the coupling is slightly slowed by ortho substituents, the reaction still goes to completion within three hours for both 2-nitrophenyl iodide (entry 11) and 2-methylphenyl iodide (entry 10). Also, heteroaromatic iodides such as 3-iodopyridine (entry 12) are well-suited for the cross-coupling reaction.

To investigate the effect of ortho substitution at the arylsilane, aryl(chloro)silacyclobutane 49 was synthesized and its reactivity was examined with several aryl iodides (Table 8). Even though the reactions were slower than those with chlorosilane 40, all the couplings with 49 give good yields of the corresponding biaryl compounds. Remarkably, sterically crowded 2-methyl-2'-nitrobiphenyl (entry 3) and 2,2'-dimethylbiphenyl (entry 4) can be prepared cleanly in 77% and 85% yields, respectively.

Extensive reaction optimization revealed five important variables: (1) palladium source, (2) arylsilane, (3) additive, (4) ligand/Pd ratio, and (5) reaction temperature. The optimal conditions involve [allylPdCl]$_2$ as catalyst and (t-Bu)$_3$P as the additive. A heteroatom substituent on the silicon of arylsilacyclobutanes is important to enhance the reactivity.

When fluorosilanes are employed, the reaction is preferably run at 50° C. with a ligand/Pd ratio equal to about 2.0. If chlorosilanes are used, the reaction is preferably performed in refluxing THF with a ligand/Pd ratio of about 4.0. For the biaryl synthesis, these conditions are milder than the other palladium-catalyzed processes including the acyclic arylsilanes and the typical Stille and Suzuki reactions.

Alkenylsilanols

To make direct comparisons to cross-coupling with alkenylsilacyclobutanes, the geometrically defined (1-heptenyl)dimethylsilanols (E)-50, and (Z)-50, and (1-heptenyl)di(isopropyl)silanol (E)-52 and (Z)-52 were chosen. These substrates are readily prepared following established procedures as outlined in Schemes 5 and 6 (22, 23). Treatment of (E)-1-bromo-1-heptene (24) with t-butyllithium, followed by the addition of hexamethyltrisiloxane resulted in the formation of (E)-50 in 74% yield. The corresponding Z-isomer was prepared in a similar manner from (Z)-1-iodo-1-heptene which upon treatment with n-butyllithium and hexamethyltrisiloxane afforded (Z)-50 in 68% yield. Silanols (E)- and (Z)-50 and (E)- and (Z)-52 were all obtained in geometrically pure form (>99%) as established by capillary CG analysis.

To investigate the influence of the non-transferable groups on the silicon atom (and illustrate an alternative entry to the silanol precursors) di(isopropyl(silanols (E)-52 and (Z)-52 (Scheme 6) were prepared. Catalytic (H$_2$PtCl$_6$) hydrosilylation of 1-heptyne with chlorodi(isopropyl)silane followed by alkaline hydrolysis provided (E)-52 in 78% yield (25). The stereoisomer (Z)-52, was produced by a high yielding four-step synthesis starting from (Z)-1-iodo-1-heptene. Lithium-iodide exchange with n-butyllithium, followed by the addition of chlorodi(isopropyl)silane formed the intermediate (1-heptenyl)di(isopropyl)silane in 95% yield. Oxidation with chlorine (0.9 M solution in CCl$_4$), followed by mild hydrolysis produced (Z)-52 in 90% yield over two steps.

The extensive optimization of reaction conditions (palladium catalyst, fluoride source, stoichiometry, solvent and temperature) already carried out in the context of the silacyclobutane coupling was the starting point for these studies. Accordingly, the silanol was first combined with tetrabutylammonium fluoride (TBAF) in THF for 10 min at room temperature, followed by the addition of the organic iodide and the palladium complex (Pd(dba)$_2$). The reactions were generally complete within 10–30 min (Table 9) to give the corresponding products 53(a–e). These conditions differ from those employed for silacyclobutanes only in the amount of TBAF added. It was shown that only two equiv. of a freshly prepared TBAF solution were sufficient to effectively promote the cross-coupling of silanols within 10 min. Further reduction in the amount of the TBAF, however, resulted in a decrease of the reaction rate and yield (cf. entries 8 and 9 in Table 9). Activator is required however, as omission of TBAF from the reaction mixtures resulted in complete recovery of both the aryl iodide and the silanol. Although a basic/nucleophilic activator is essential, it need not be fluoride. Indeed, substitution of tetrabutylammonium fluoride with the corresponding hydroxide (as a 2.0 M solution in methanol) gave rise to comparable rate and yield for the coupling of (E)-50 with naphthyl iodide (cf. entries 3 and 5, Table 9). However, the product is accompanied by 2.5% of the cine rearrangement product when TBA-OH/methanol is used.

Removal of the silicon-containing byproducts and isolation of the styrenes was readily accomplished by a three step procedure, (1) filtration of the crude reaction mixture through a plug of silica gel; (2) column chromatography (silica gel or reverse phase C18); and (3) distillation.

The experiments described in Table 9, clearly demonstrate that the influence of the different functional groups present on the aryl iodide is minimal. The rate and yield of the reactions are not affected by functional groups. The presence of electronically neutral (entries 1–5), electron donating (entries 12 and 13) as well as electron withdrawing (entries 8 and 9) substituents is well tolerated.

Rates and yields for the cross coupling of silacyclobutanes and dimethylsilanols were similar, but the selectivities obtained with the dimethylsilanols were slightly lower than those observed with the silacyclobutanes; up to 5.5% of the geometrical isomer was observed, starting from a single, pure isomer of the (E)- and (Z)-52. The results summarized in Table 10 show that the rates for the cross coupling are independent of the substituents on the silicon atom. The selectivity of the reaction is now comparable to the selectivity observed with silacyclobutane and substantially improved over the selectivity obtained with the dimethylsilanols (for example cf. Table 9, entries 1 and 2 and Table 10, entries 1 and 2). Moreover, when tetrabutylammonium hydroxide was used as the activator (cf. Table 9, entry 5 and Table 10, entry 5) no cine rearrangement produce was observed.

As was the case with alkenylsilacyclobutanes, silanols (E)-50 and (Z)-50 undergo rapid and stereospecific cross-coupling with alkenyl iodides as well. Under conditions identical to those employed previously, the vinyl iodides (E)- and (Z)-6-iodo-5-hexenols reacted with the silanols to give conjugated dienes 54 in good yield (Table 11). The reactions were generally slower than the coupling reactions with aryl iodides. In all cases, the desired products were contaminated with a small and variable amount of an isomeric diene 55 which presumably arose from a cine rearrangement pathway (as was also observed previously). Stereospecificity, again, is similar to that obtained with aryl iodides, some loss in configurational homogeneity of the double bond arising from the silanol is observed, whereas the double bond originating from the iodide is not affected. In entry 5, up to 10% of the stereoisomeric (E,Z)-54 was formed, although, this compound may be prone to isomerization, there is almost twice as much isomerization as with silacyclobutane. In this case a different palladium-catalyst [allylPdCl]$_2$ had to be used, as Pd(dba)$_2$ was not effective, and led to even more isomerization. When the methyl groups on the starting silanols were replaced with isopropyl groups (entries 2 and 6), the selectivities are again improved with respect to the ratios observed with silacyclobutane.

There is a dramatic difference between the rate of coupling of the alkenylsilanols of this invention and those described recently by Hiyama (13). The reactions exemplified herein use different palladium sources and different activators. Hiyama employs Pd(PPh$_3$)$_4$ and silver(I) oxide in DMF solution. Phosphine ligands appear to inhibit the cross-coupling reaction. In contrast, the method of this invention with silanols uses activators which can be other basic and nucleophilic, such as F— or OH— sources, tetraalkylammonium fluoride or the corresponding hydroxide. Without wishing to be bound by any particular mechanism, it is currently believed that there is an association between the silanol (silyloxide) and the palladium center prior to and facilitating the transmetallation event (27). Both types of activators (R$_4$N$^+$X$^-$ and Ag$_2$O) are in principle capable of acting as bases to deprotonate the silanol and, thus, assisting in the association with the palladium intermediate. However, fluoride and hydroxide differ from Ag$_2$O, because both fluoride and hydroxide can also act as nucleophiles to further promote the transmetallation by forming siliconate complexes.

(α-Alkoxyvinyl)silanols

Scheme 7A illustrates the general cross-coupling reaction of (α-Alkoxyvinyl)silanols with aryl electrophiles. The reaction illustrated has been investigated for both cyclic and linear vinyl ethers.

Palladium-catalyzed cross-coupling of cyclic vinyl ether 61 with aryl iodides is exemplified in Table 12.

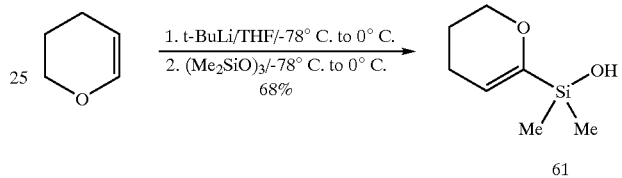

61

Compound 61 was generated by metalation of 2H-3,4-dihydropyran with t-BuLi according to Soderquist's procedure (31) and subsequent reaction with hexamethylcyclotrisiloxane (32) resulted in the formation of [2-(5,6-dihydro-4H-pyranyl)]dimethylsilanol (61) in 68% yield. The optimization of the palladium(0)-catalyzed cross-coupling was guided by the previous studies with alkenylsilanols.

Accordingly, silanol 61 was first combined with a 1.0 M solution of tetrabutylammonium fluoride (TBAF.3H$_2$O, Fluka) in THF at room temperature, followed by the addition of the aryl iodide and the palladium complex (Pd-(dba)$_2$). The reactions were clean and generally complete within 10–20 min. However, as had been noted previously, difficulties were encountered in the purification step because (1) the polarity of the products was similar to the dba ligand and to the polysilicone byproducts and (2) the products were found to be particularly labile in air and on chromatographic media. Moreover, reverse-phase (C-18) silica chromatography was either not efficient or led to partial decomposition of the products if long gradient elutions were used. By using rapid silica gel column chromatography, the polysilicone byproducts could be separated, but the product was always contaminated with dba. By the simple expedient of replacing the Pd(dba)2 catalyst with [allylPdCl]$_2$, the cross coupling products 62 (Table 12) were obtained in an analytically pure form.

The scope of the cross-coupling reaction of 61 was further investigated with aryl iodides bearing electron-withdrawing or electron-donating groups in para, meta, or ortho positions (Table 12). For all aryl iodides examined, the reaction proved to be fast and high yielding. Several features of the reaction are noteworthy: (1) electron-withdrawing or-donating groups exhibit similar reactivity (entries 4 and 6), (2) the steric effect of ortho substituents is minimal (cf. entries 1 and 4–7) except in the case of the 2-carbomethoxy group (entry 3) where chelation between the carbonyl moiety and the palladium may slow the reductive elimination step, (3) the reaction tolerates diverse functionalities such as ester, nitro, cyano (vide infra), ether, and even hydroxyl. The mild reaction conditions and uniformly high yields compare favorably with other methods to produce these compounds.

The cross-coupling of 61 with an alkenyl electrophile, ethyl (E)-3-iodoacrylate, to give cross-coupling product 63 was also examined:

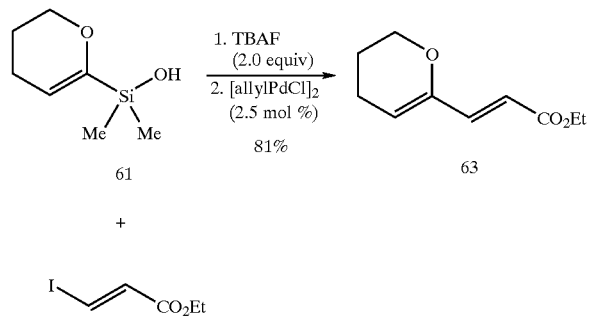

The reaction rate and yield were comparable to that obtained with aryl iodides, and after 2 h, 63 could be isolated in 81% yield after $Al_2O_3$ chromatography. The corresponding (Z)-3-iodoacrylate suffered decomposition under the reaction conditions and did not lead to coupling.

Following the successful coupling of silanol 61, the use of (1-butoxyvinyl)dimethylsilanol and [2-(4,5-dihydrofuranyl)] dimethylsilanol were then considered. However, the sequence established for the synthesis of 61 (lithiation of the vinyl group and subsequent quenching) did not provide the silanols cleanly.

Previous experience with handling silanols suggested that increasing the bulk of the silicon substituent could make the products more tractable. Since hexaisopropylcyclotrisiloxane is not commercially available, an alternative procedure that involves (1) lithiation of the vinyl ether, (2) addition to chlorodiisopropylsilane (to form the intermediate silyl hydride), (3) oxidation of the hydridosilane with chlorine to form the chlorosilane, and (4) alkaline hydrolysis to produce the silanol can be employed to prepare silanols useful in the cross-coupling reactions herein.

Cyclic Silyl Siloxanes

The cyclic silyl siloxane 74 was prepared by ring-closing metathesis (RCM) using the molybdenum carbene complex 72 [($CF_3$)MeCO]$_2$Mo(=CHCMe$_2$Ph)(=NC$_6$H$_3$-2,6-i-Pr$_2$) developed by Schrock et al. (33):

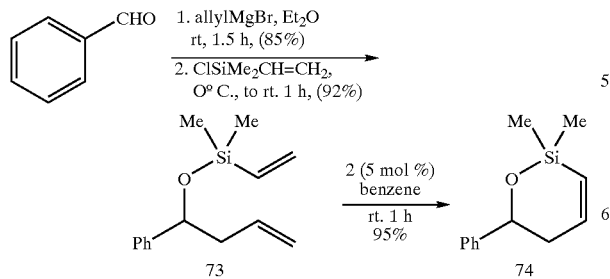

Optimization of the Pd(0)-catalyzed coupling with siloxane 74 and 4-iodoacetophenone employed the conditions developed with alkenyl silanols. Thus, siloxane 74 was combined with a 1.0 M THF solution of tetrabutylammonium fluoride (TBAF.3H$_2$O) at room temperature, followed by the addition of 4-iodoacetophenone and 5 mol % of Pd(dba)$_2$, sequentially. The reaction proceeded cleanly to completion in only 10 min. Decreasing the loading of Pd(dba)$_2$ only marginally affected the rate of the coupling process. However, with a lower catalyst loading (1.0 mol %) or less TBAF (1.0 equiv) the reaction did not go to completion and a significant amount of 4-iodoacetophenone was recovered.

With suitable conditions for the cross-coupling processing in hand, the reaction was examined with various aryl iodides. Scheme B illustrates the reaction of cyclic siloxanes with aryl iodides. Both the nature and position of substituents on the aromatic ring were studied. The results compiled in Table 13 reveal high compatibility with the common functional groups tested. For all aryl iodides examined, the reaction gave uniformly high yields. Noteworthy features of this process include the following: (1) electron-withdrawing or electron-donating groups exhibit similar reactivity (entries 1 and 2), (2) the steric effect of ortho-substituents is minimal (entry 4) except in the cases where a possible chelation between the substituent and the palladium may slow the reductive elimination step (entries 5–7), (3) the reaction tolerates diverse functional groups such as ester, ether, nitro, and even free hydroxy group, and (4) the reactions of all iodides were stereospecific.

The cross-coupling of 74 was also successful with (E)-2-bromostyrene. The reaction rate and yield were slightly lower than that obtained with aryl iodides. With 2.5 mol % of [allylPdCl]$_2$ as the catalyst, the coupling product could be isolated in 78% yield after 5 hr.

The influence of ring size on the cross-coupling reactin was examined. A variety of aryl iodides bearing various functional groups was selected to expand the utility of this transformation. The results collected in Table 14 reveal that (1) the different sizes of cyclic alkenyl silanes exhibit similar reactivity in the coupling reaction (entries 1 and 4) and (2) substitution on the β-trans-position of the silyl group did not affect the reactivity significantly (entry 2). The α-substituted alkenyl silane 76c did undergo the coupling process; however, a significantly reduced reaction rate compared to the related silanes was observed. Moreover, the reaction mixture contained a substantial amount of self-coupling product of ethyl 3-iodobenzoate. The use of additives or slightly elevated temperatures did not improve the results. Fortunately, the addition of the iodide in portions satisfactorily suppressed the formation of the self-coupling product.

Moreover, increasing the loading and portionwise addition of the Pd(0) complex also provided complete conversion and kept the palladium from precipitating in this slow coupling reaction. A comparison between these results and those described above reveals that monosubstitution of alkenyl silanes (silacyclobutanes and silanols) in either the α- or β-position does not effect the rate of the cross-coupling process significantly. The disubstituted alkenyl silanes, including cyclic siloxanes, and silyl hydrides are also very reactive in the coupling process except in the case of the substitution on both of the α- and β-cis-positions, for example, 76c. The steric influence may slow the coupling reaction and allow a competitive homocoupling of the aryl iodides to intervene.

The cyclic siloxane 78 was formed by intramolecular hydrosilyation as will be discussed below.

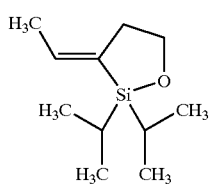

Siloxane 78 was dissolved in 2.0 equiv of a 1.0 M solution of TBAF in THF, followed by the addition of iodobenzene and 5 mol % of Pd(dba)2. The siloxane did undergo the coupling process, however, at a significantly reduced reaction rate compared to the related silanols. Moreover, the reaction mixture was contaminated with a substantial amount of biphenyl (the product of self-coupling of iodobenzene), and thus the yield of the cross-coupling product was attenuated. The addition of various ligands or decreasing the amount of Pd(0) did not meaningfully improve the results. It was found, however, that adding the iodide in portions satisfactorily suppressed the formation of biphenyl and correspondingly improved the yield of the desired coupling product. The portionwise addition of the iodide proved to be effective in reducing the amount of homocoupling byproduct in most cases. For a few, very slow reacting substrates, even this expedient was not helpful.

With a reproducible procedure in hand, the scope of the reaction with regard to the nature and position of substituents on the aromatic ring was explored The results compiled in Table 15 reveal good compatibility with all common functional groups tested (ester, ketone, nitro, alcohol, nitrile, ether). For all aryl iodides examined, the reaction proved to be mild and high yielding except in the case of 2-nitroiodobenzene (entry 4) which was very slow and gave a substantial amount of nitrobenzene as a by-product. Noteworthy features of this process are that (1) electron-withdrawing or electron-donating groups exhibit similar reactivity, (2) ortho substituents on the aryl iodide do not affect the reactivity significantly, (3) the reaction tolerates diverse functional groups such as ester, nitro, cyano, ether, and even free hydroxy group, and (4) the reactions of all halides were stereospecific, with the exception of 4-nitroiodobenzene and l-iodonaphthalene, which gave a small amount of the geometrical isomer.

This variant of the coupling reaction is not limited to benzene derivatives. For instance, 1-iodonaphthalene, 1-bromo-4-tert-butyl-1-cyclohexene (an unactivated vinyl bromide), and 3-iodopyridine reacted with 78 to give the expected products 79k, 79l, and 79m, respectively in reasonable to good yield:

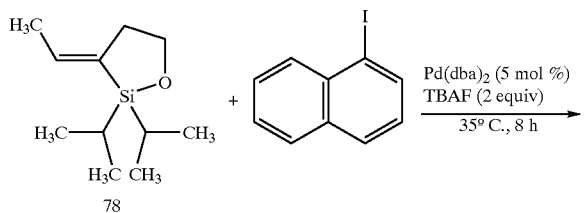

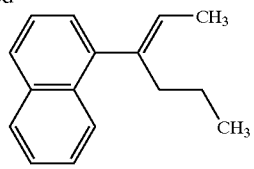

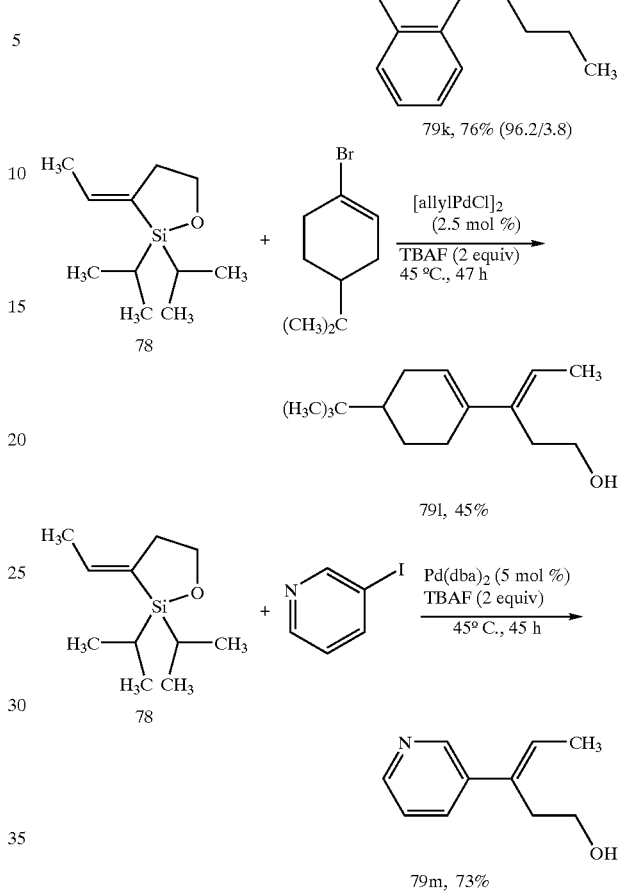

The optimization of this process next turned to the investigation of the importance of the silicon substituents. It was of interest to see whether and how the size of the substituents on the silicon would affect the rate and selectivity of the reaction. Additional benefits such as improved mass efficiency and ease of by-product removal could be realized with a smaller group in place of an isopropyl group. We thus focused our attention oil the corresponding dimethylsiloxane.

However, the synthesis of the siloxanes was problematic. The intramolecular hydrosilylation of dimethylsilylethers with chloroplatinic acid resulted in polymeric materials. Though the platinum(0)-1,3-divinyl-1,1,3,3-tetramethyldisiloxane complex (Pt(DVDS)) gave clean in-tramolecular hydrosilylation, any attempts to obtain the siloxane in a pure state or to scale-up the preparation of the siloxane led to oligomerization.

A practical solution to this problem was conceived in the form of a one-pot protocol that would (1) obviate the need to isolate and purify the delicate silyl ether and siloxane and (2) improve the overall efficiency of the process. Thus, to streamline the procedure and minimize the formation of potentially deleterious byproducts, tetramethyldisilazane (TMDS) was employed as the silylating agent. The one-pot process is discussed below.

Silyl Hydrides

Silyl hydrides are useful precursors for cross-coupling, particularly in those cases where the hydroxyl functionality would not be tolerated. Scheme 7B illustrates the reactions of silyl hydrides with aryliodides. Silyl hydrides were prepared as exemplified for hydrides 84–86:

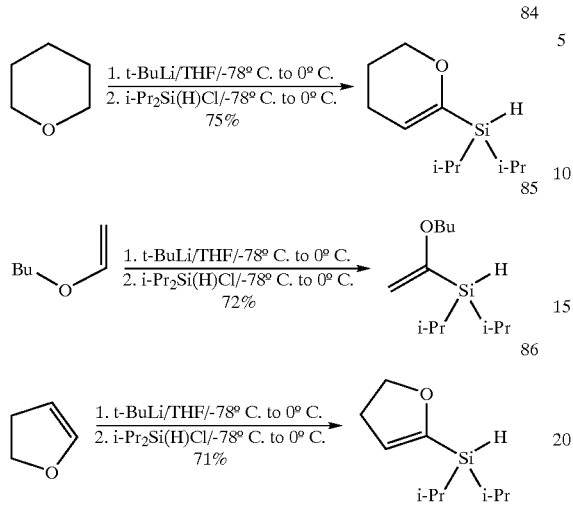

Subjecting the hydridosilane 84 and 2-iodotoluene to the reaction protocol optimized with silanols gave rise to only a small amount of coupling product along with 1,5-diphenyl-3-pentanone from reduction of dba. The evolution of a gas when the silane was mixed with TBAF suggested that the silyl hydride was being hydrolyzed. It is well-known that hydrolysis or alcoholysis of silyl hydrides can be catalyzed by fluoride ion at room temperature to liberate hydrogen gas. Thus, it appeared that the coupling product observed could be the result of silanol generated in situ from the silyl hydride.

The reaction protocol was slightly modified to examine whether or not in situ generation of the silanol from the silyl hydride could be used to obtain cross-coupling. Thus, the silyl hydride was first combined with TBAF (the activator) for 1–20 min. at room temperature until no further gas evolution was observed at which point the organic iodide and palladium catalyst were added sequentially to the reaction mixture. Using this revised method cross-coupling products as listed in Table 16 were prepared.

Attempted reaction of the silyl hydride 86 under these conditions failed. It appears that silyl hydride 86 suffered rapid protiodesilylation in the presence of TBAF releasing dihydrofuran. Replacement of TBAF with tetrabutylammonium hydroxide (3.0 equiv.) in methanol allowed the coupling of 86 with the aryl iodide to proceed smoothly in reasonable yield (Table 16) entry 6.

Siloxanes

A wide variety of siloxanes is available in the art, either through well-known methods of synthesis or from commercial sources (see, for example, Gelest, Inc, Tullytown, Pa.), including siloxanes with one or more substituents that are T groups as defined herein, e.g., vinyl-, allyl-, and aryl-substituted siloxanes. Siloxanes have been found to be useful organosilicon nucleophiles for the cross-coupling reaction of this invention. Scheme 9 generally illustrates the reactions of siloxanes with aryl iodides. The siloxane reagents contain at least one transferable group (T), but typically contain a plurality of transferable groups.

Table 17 lists several exemplary cross-coupling reactions of vinyl-substituted siloxanes, e.g., two cyclic (92, 93), branched (94) and linear siloxane (95). Cross-coupling to form product 97 by reaction of 4-iodoacetophenone 96 with the cyclic and the branched siloxane in the presence of Pd(dba)$_2$ and TBAF (in THF) was substantially complete within about 10 minutes. The linear siloxane was found to be less reactive under the same conditions, where about 91% conversion to product was observed after 8 hours.

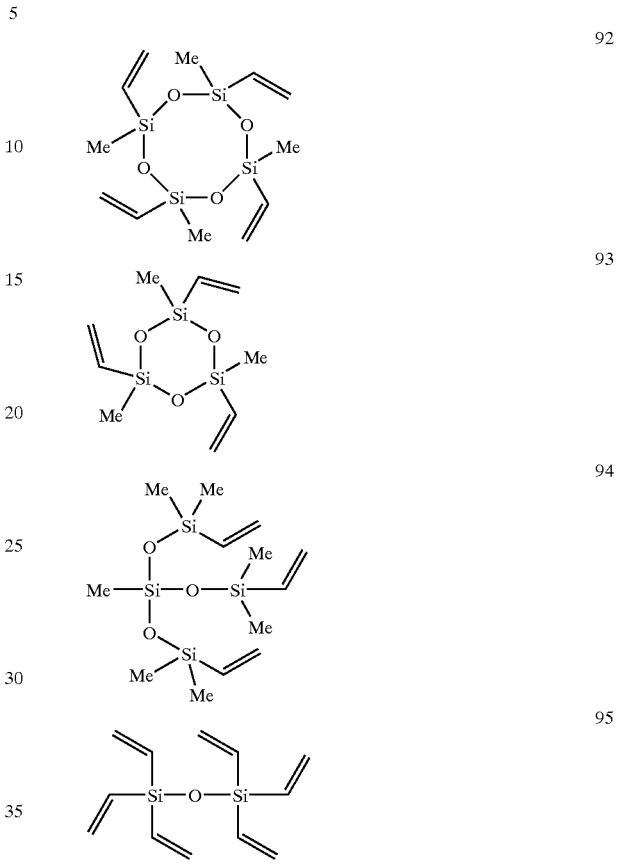

For orienting experiments, 4-iodoacetophenone (96) was chosen to test the coupling of vinylpolysiloxanes using reaction conditions employed previously with minimum modification (5 mol % Pd(dba)$_2$, two equivalents tetrabutylammonium fluoride (1.0 M in THF, room temperature). The established stoichiometry of transferable vinyl group to iodide was maintained at 1.2:1, thus the molar equivalents of each precursor was divided by the number of available vinyl groups. Silanes 92, 93 and 94 underwent rapid coupling. In all of these cases, the starting iodide was completely consumed at room temperature within 10 min to afford the product 97 in 88, 85 and 89% yields, respectively.

The coupling reaction of 95, however, did not proceed to completion. The initial rate of coupling, however, was not slow (78% conversion at 10 min). Even by extending the reaction time to 5 h, the reaction did not go to completion. Further increasing the loading of reagent 95 to 1.5:6 equivalents and also increasing the amount of TBAF to three equivalents gave 93% conversion at 10 min (entry 6), but the progress of the reaction once again stalled. A 2.0 mmol scale descriptive run under these conditions afforded the coupling product in low yield (53%). From these results it is clear that vinylation precursors 92, 93 or 94 could each be employed for this transformation.

On the basis of cost and efficiency of vinyl transfer, the vinylpolysiloxane 92 was chosen for further examination of scope of the coupling reaction with a number of different aryl and alkenyl iodides. The results are collected in Table 18. As had been previously observed, the coupling reaction between 92 and electron poor iodides (4-iodoacetophenone 96, ethyl 4-iodobenzoate 98 and 3-iodonitrobenzene 102) proceeded smoothly to afford the corresponding products in high yields. When the loading of Pd(dba)$_2$ was decreased to 1 mol %, the reaction of 92 with 98 was also complete in 1 h to afford the product in comparable yield (83%). In all these experiments, the catalyst was added last which caused a significant exotherm (up to 55° C. on a 2 mmol scale) for the fast acting substrates (5, 7, 11). A modified procedure in which a solution of 96 was added last such that the temperature was maintained at <30° C., gave comparable results in the same time period (entry 2).

From foregoing studies on the coupling with electron-rich iodides, it is not surprising that the reaction of 4-iodoanisole with 92 was very sluggish under the same conditions. Although 100 was consumed after 4 h under the standard conditions (with three equivalents of TBAF), the isolated yield was quite low 46% (entry 4) and 15% of the corresponding Heck reaction product ((E)-4,4'-dimethoxystilbene) was also isolated. In the cross coupling with 1-methyl-1-vinylsilacy-clobutane, the Heck reaction by-products were primarily observed with 100 and 110. In those cases, the intervention of the stilbene by-products was suppressed simply by increasing the amount of one to 1.2 and 1.5 equivalents, respectively. In this system, however, it seems that the Heck reaction is more competitive since a trace of stilbene was observed in the coupling reaction of 92 with 98 as well as with 100 and 110 (entries 2, 3). Moreover, in the coupling reaction of 100 and 110, increasing the amount of 92 was not effective in suppressing the side reaction. The yields of the desired products improved upon addition of 10 mol % Ph$_3$As (entry 5) although Heck product was still observed. Nevertheless, this material can be easily separated from the product by chromatography. The use of Ph$_3$As was beneficial for most of the slower coupling substrates. This allowed for the solubilization of the palladium (0) through many catalytic cycles.

The effect of sterically demanding substituents observed in the coupling of 1-methyl-1-vinylsilacyclobutane was also seen in reactions with 92. Thus, reaction of 92 with 2-iodoanisole 105 was extremely sluggish compared with that of 4-iodoanisole 100 (6 vs. 24 h for completion). The importance of steric effects was apparent in the reaction of methyl 2-iodobenzoate 108, an electron poor iodide, which required 8 h to go to completion (entry 9, in the presence of 10 mol % Ph$_3$As) compared with just 10 min for the para-isomer 98 (entry 2). The compatibility of a free hydroxyl functional group was demonstrated in the successful coupling of 3-iodobenzyl alcohol (entry 7) at a reasonable rate and in good yield.

Finally, we also examined the coupling of vinylpolysiloxane 92 with (Z)-6-iodo-5-hexen-1-ol 112. Although the reaction was sluggish, it proceeded to completion in 24 h to give the diene 113 in 52% yield. The process was stereospecific as established by GC-MS analysis. The compatibility with the free hydroxyl group is also noted.

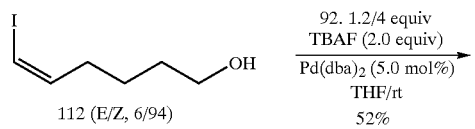

112 (E/Z, 6/94)

92. 1.2/4 equiv
TBAF (2.0 equiv)
Pd(dba)$_2$ (5.0 mol%)
THF/rt
52%

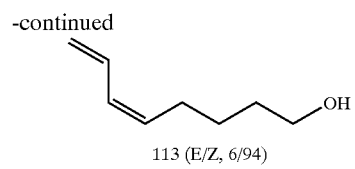

113 (E/Z, 6/94)

Siloxanes such as 92, 93 and 94 are effective vinylation reagents of aryl and alkenyl iodides under mild condition in the presence of TBAF (two equivalents) and Pd(dba)$_2$. In view of the mildness and generality of the transformation along with the cost and non-toxic nature of the silicon reagents and by-products, this procedure should become the reaction of choice for large scale and laboratory preparations.

Bis-silylethenes

It was found that bis-silylethenes were useful reagents in the cross-coupling reaction of this invention and were of particular use for the synthesis of stilbenes on reaction with aryl electrophiles. Bis-silylethenes contain the moiety "Si—C=C—Si." Scheme 10 illustrates cross-coupling reactions of bis-silylethenes with aryl iodides.

More specifically, 1,2-bis(dimethylethoxysilyl)ethene (126, 0.5 equiv) reacted with ethyl 4-iodobenzoate (1 equiv) in the presence of Pd(dba)$_2$ (0.05 equiv) and TBAF (2 equiv) in THF to give the cross-coupling product diethylstilbene-4,4'-dicarboxylate (127) (RT/9.5 h, yield 94% conversion):

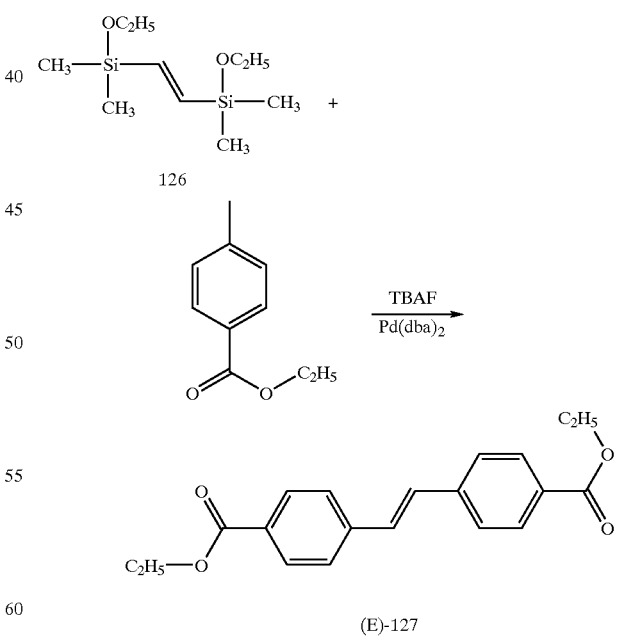

In this case, the transferable group is linked between two silicon atoms in the reagent and ultimately is coupled to two acceptor groups. A bis-silyl reagent is generalized in formula 130. Useful bis-silyl cross-coupling reagents also include those of the formula 131.

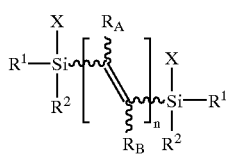

where X, $R^1$, $R^2$ are defined above and $R_A$ and $R_B$ can be any olefin substituent noted above which represents a bis-silyl reagent with monoolefin or conjugated olefin T group; and

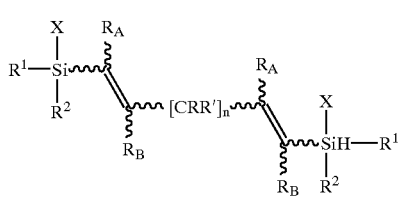

where X, $R^1$, $R^2$, are defined above, n is an integer equal to or greater than 1 (typically less than about 6) and $R_A$ and $R_B$ can be any olefin substituent noted above and R and R' are any alkyl substituents noted above which represents a bis-silyl reagent with a non-conjugated diene T group.

The bis-silyl reagents (e.g., species containing the Si-T-Si moiety) are particularly suitable for linking T groups that are olefins, substituted olefins, dienes, substituted dienes (conjugated or non-conjugated), polyenes and substituted polyenes (conjugated and non-conjugated) between two aryl groups. Table 19 illustrates the results of several reactions of aryl and or olefinic acceptors using the 1,2-bis (dimethylethoxysilyl)ethene reagent 126 where reaction conditions are listed in the Table footnotes.

Fluoride-free Cross Coupling Reactions

One serious limitation in the use of a fluoride source as the activator of the cross-coupling reaction is that this agent precludes employment of this reaction in syntheses where either of the coupling substrates contains silyl protective groups. A non-fluoride-activated, organosilicon cross-coupling using inexpensive commercially available reagents has been developed which overcomes this limitation and further expands the utility of the cross-coupling reactions of this invention.

The results of a survey of bases and solvents using (1-heptenyl)dimethylsilanol (E)-21 and 1-iodonaphthalene are collected in Table 20. Whereas the lithium silyloxide was unreactive, the sodium salt, generated with NaH in THF clearly manifested the feasibility of this new process (entries 1–4). 2.0 equiv of base was needed for complete conversion, which was then used throughout. The reaction is considerably faster in DMF and DME. Other sodium bases (i.e., NaOt-Bu) were less effective promoters. The use of potassium hydride had a dramatic effect on the rate giving complete conversion within 15 in DME. Finally, potassium tert-butoxide was also able to promote the reaction and gave the highest yield despite the having the lowest rate of coupling. Weaker bases, such as $K_2CO_3$ and $K_3PO_4$ were ineffective. In all cases examined the reaction was shown to be highly stereospecific. Scheme 11 illustrates reaction of vinyl silanols with aryl iodides in the presence of bases such as hydride.

Application of the optimal reaction conditions to the coupling of (Z)-21 with 1-iodonaphthalene gave rapid cross-coupling but in markedly lower yields, Table 21, entry 1. The remainder of the mass balance was identified as naphthalene, presumably arising from the formation of a palladium hydride species from the excess KH. Although the formation of naphthalene could be suppressed by the use of KOt-Bu, the reaction rate with this base was far too low to be synthetically viable. Apparently, KOt-Bu is able to compete with the silyloxide for the palladium center thus serving as a competitive inhibitor. From this observation, it appears that the ideal base need only be strong enough to produce a measurable equilibrium concentration of the silyloxide, and not be a competitive inhibitor. Logically, the first choice would be another silyloxide, such as the soluble agent $KOSiMe_3$. 2.0 equiv of this mild base can effect the cross-coupling at room temperature, in excellent yield, with stereospecificity and without reduction by-products (albeit more slowly than KH). Neither increasing nor decreasing the amount of $KOSiMe_3$ improved the rate of the coupling.

The scope of this new, fluoride-free coupling process was examined under the optimal conditions of 2.0 equiv of $KOSiMe_3$ in DME at room temperature. The results in Table 22 illustrate that cross-coupling products were obtained in excellent yields with reasonable rates. High stereospecificities and good yields were obtained in the coupling of (E)-21 and (Z)-21 to 1-iodonaphthalene and iodobenzene. In addition, both electron rich (entries 7 and 8) and electron deficient (entries 5–6 and 9–12) arenes couple quite well, although with varying rates. In general, electron deficient electrophiles couple most rapidly, except 4-iodo-acetophenone. Apparently, the presence of a moderately acidic proton in the substrate has a detrimental effect on the rate of coupling, although the yields were still high and no other by-products were observed. In contrast to the fluoride-activated couplings of silanols, the rates of coupling with (Z)-21 were significantly lower than those with (E)-21 .

The synthetic potential of this new method is clearly demonstrated by the compatibility of a silyl protective group as shown in entries 13–14. The coupling reaction occurs cleanly in the presence of a TBS protected alcohol on the aryl iodide, 154 g, without any observable deprotection.

One-pot Hydrosilyation/Cross-coupling

Scheme 1 illustrates the hydrosilyation of terminal alkynes combined with cross-coupling reactions of this invention. A one-pot protocol was developed to carry out this reaction.

The initial development of a one-pot protocol focused on the Pt-catalyzed hydrosilylation event. To optimize the hydrosilylation, the reaction of 1-heptyne with diisopropylchlorosilane was studied and the results were evaluated by directly carrying out the Pd-catalyzed cross-coupling (THF, 1.0M TBAF (2 equiv.), $Pd(dba)_2$ (5 mol %), RT, 10 min.) with 1-iodonaphthalene. Hydrosilylation of 1-heptyne with diisopropylchlorosilane in the presence of $H_2PtCl_6$ (0.1 mol %) at 50° C. for 30 min, followed by treatment with TBAF, $Pd(dba)_2$, and 1-iodonaphthalene gave incomplete coupling (70–80% conversion). No other isomeric, cross-coupling products ((Z)-169a or 170a) were observed by GC analysis. However, all attempts to improve the conversion failed. Consequently, a survey was performed to screen other silane sources and Pt catalysts for their activity and stereoselectivity in this transformation. Orienting experiments revealed that the regio- and stereoselectivity was strongly affected by the structure of silane. In the presence of Speier's catalyst, tetramethyldisiloxane, tetramethylcyclotetrasilioxane, and methyldiethoxysilane can participate in the hydrosilylation/cross-coupling reaction smoothly as evidenced by the complete consumption of 1-iodo naphthalene after 10 mm.

However, a small amount of the isomer 170a (12–16%) resulting from regio-reversed hydrosilylation was observed. To improve the hydrosilylation regioselectivity, tetraisopropyldisiloxane was used, but only a trace of cross-coupling product was observed even after extended reaction time or at elevated reaction temperatures. Diethylethoxysilane was then examined as a compromise between reactivity and selectivity. Surprisingly, this silane gave the poorest results; the regioselectivity was worse than with the methylsilanes, and the conversion was below about 60%.

The next stage of optimization involved the examination of these silanes with other platinum catalysts to improve the rate and/or regioselectivity. The organic soluble complex Pt(0)-1,3-divinyl-1,1,3,3-tetramethyldisiloxane (Pt(DVDS)) gave results comparable to those obtained with Speier's catalyst. However, the t-Bu$_3$P-modified Pt(DVDS) complex gave significantly improved results. The hydrosilylation with both 162 and 163 was complete within 30 min at room temperature in the presence of t-Bu$_3$P—Pt(DVDS), and the subsequent coupling reaction with 1-iodo naphthalene was complete in 10 min at room temperature. Moreover, with 162 the coupling product contained only 2% of the regioisomer 170.

With an optimized procedure for the hydrosilylation/cross-coupling reaction in hand, a variety of iodides bearing various functional groups and substitution patterns were selected to define the scope of the one-pot process. The results presented Table 23 reveal that the rate, yield, and selectivity of this protocol correspond well to those features of the previous cross-coupling reactions of isolated silanols. For example, both electron-rich (entries 3, 4, 7, and 9) and electron-poor (entries 2, 5, 6, and 8) iodides underwent the coupling smoothly to give the desired product in high yield and excellent stereoselectivity.

The position and nature of substituents had little effect for most iodides (cf. entries 3 and 9). However, the rate of coupling of 168f was very slow and stalled as has been noted previously. This problem was resolved by adding 10 mol % of AsPh$_3$. The coupling of 168h also proceeded smoothly to give desired product in reasonable yield, although some loss of specificity was observed. Further, 168i also showed good results when [allylPdCl]$_2$ was used, but the specificity again was lower than with aryl halides. The origin of the erosion in stereospecificity is not understood at this time. As found in previous studies, it was possible to reduce the loading of the Pd catalyst for the coupling of electron-poor iodides, e.g., 168d. In the presence of 1 mol % of Pd(dba)$_2$ the coupling product 169d was produced in 89% yield by extending the reaction time to 60 min with comparable selectivities (cf. entries 5 and 6). The standard reaction protocol developed in earlier studies for the cross-coupling calls for the addition of the palladium catalyst last (procedure I). For reactive electrophiles such as electron-deficient aryl iodides, the reaction becomes rather exothermic. This potential problem can be solved by simply changing the addition sequence such that TBAF and Pd(dba)$_2$ were added to the hydrosilylation mixture first. The heat of reaction is then modulated by the slow addition of the iodide such that the internal temperature does not exceed 30° C. (procedure II). The one-pot coupling of 168c gave 169c in 89% yield by using this modified procedure (cf. entries 3 and 4). The overall process displays good generality and functional compatibility with regard to the alkyne component as well, Table 24.

A number of alkynes were evaluated with typical electron-poor (168b) and electron-rich (168c) substrates. The alkyne diversity is represented by aromatic (171), linear aliphatic (172), and branched aliphatic (173) types. In addition, we included unprotected alcohol functions (12 and 173) and a remote double bond (174). The coupling reaction of 171 proceeded smoothly to give products in high yield, and no regioisomer was detected by GC analysis. Furthermore, those alkynes that contain free hydroxy groups underwent facile, highly stereoselective coupling though the latter required a longer reaction time. The coupling of 174 also gave exceptional results. The double bond did not compete with the alkyne in the hydrosilylation, and no Heck reaction products were observed. However, some Sonogashira coupling of the alkyne was observed when the ratio of 162 to 174 was 0.65 /1.5 equiv. The by-product can be eliminated by increasing the 162/174 ratio to 0.98/1.5 and also extending the reaction time to 60 min.

In summary, an efficient hydrosilylation system uses inexpensive, nontoxic silicon reagents and soluble Pt catalyst. The in situ generated disiloxanes then undergo a Pd-catalyzed, cross-coupling for the mild, one-pot hydrocarbation of 1-alkynes. This method is characterized by good generality, functional group compatibility, and stereoselectivity.

Ring-closing Metathesis Combined with Cross-coupling of this Invention

Cross-coupling reactions of the five-, six- and seven-membered cycloakenylsiloxane (74 and 76) are summarized in Tables 13 and 14 above. These siloxanes carry substituents on both alkenyl carbons and cross-coupling reaction with aryl iodides results in stereocontrolled synthesis of highly substituted unsaturated alcohols. The starting siloxanes 74 and 76 were prepared by ring closing metathesis of alkenyldialkylsilyl ethers of ω-unsaturated alcohols.

Ring-closing metathesis (RCM) catalyzed by Mo or Ru complexes has revolutionized the way in which carbocycles and heterocycles are constructed. (34). In view of the not uncommon use of silyl ethers as tether anchor points, there is an opportunity for the combination of RCM and Pd-catalyzed cross-coupling chemistry of this invention by use of alkenyl silylethers. Scheme 13 illustrates the combination of RCM reaction catalyzed by a Mo complex and the cross-coupling reaction of this invention.

RCM of the sterically more demanding vinylsilyl ether dienes requires the less sterically sensitive molybdenum carbene complex [(CF$_3$)$_2$MeCO]$_2$Mo(=CHCMe$_2$Ph) (=NC$_6$H$_3$-2,6-i-Pr$_2$)(202), developed by Schrock et al.(33).

To test the feasibility of the overall transformation, combining the two types of reaction the vinylsilyl ether, 203, was prepared as a starting material for RCM by addition of allylmagnesium bromide to benzaldehyde followed by silylation with commercially available chlorodimethylvinylsilane. Initial studies on the RCM reaction of 203 using the Grubbs alkylidene complex none of the desired ring-closure product 74, was observed. All variations in conditions, including change of solvent and/or temperature were unsuccessful. Substrate 203 did undergo the RCM process when the molybdenum complex 202 was used as the catalyst. After careful optimization a near quantitative yield of 74 was obtained with 5 mol % of 202 in benzene at ambient temperature.

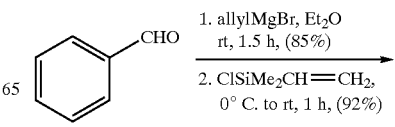

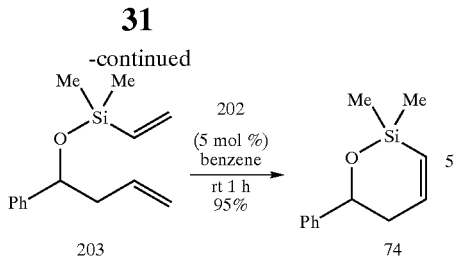

The influence of tether length (i.e., ring size) and substituents on the RCM/cross-coupling process was examined as shown in Table 25. The allylic ether 207a (a five-membered ring precursor) suffered RCM under the standard conditions (5 mol % of Mo complex in benzene, 1 h); however, only 75% conversion could be obtained in 1 h. This problem was solved by increasing the catalyst loading; using 7 mol % of catalyst, the complete consumption of 207a was achieved within 3 h to afford the product 208a in 89% yield (Table 25, entry 1) However, for the preparation of seven-membered siloxane 208d, the reaction only went to 91% completion, giving an 81% yield under these conditions. With a monosubstituted alkene or monosubstituted vinylsilane (entries 2 and 3), the RCM process proceeded slowly compared to 74 albeit ultimately to completion. Unfortunately, substitution on both the alkene and vinylsilane (entry 4) did not lead to successful closure (even under harsher conditions), presumably as a result of the significant increase in steric demand.

The results illustrated in Table 25 demonstrating successful RCM reaction to form the cyclic siloxanes (such as 74) along with the results of successful cross-coupling reactions of those siloxanes illustrated in Tables 13 and 14 demonstrate the viability of sequential RCM/cross-coupling reactions employing readily available silyl ethers. The cycloalkenylsiloxane serves as a competent donor undergoing rapid and high-yielding cross-coupling with various aryl and alkenyl halides.

Intramolecular Hydrosilylation combined with Cross-coupling

Facsile cross-coupling reactions of this invention are observed with organosilicon reagents having oxygen function on the silicon, e.g., alcohols, ethers or disiloxanes. Starting materials for the coupling reactions herein can be obtained by intramolecular hydrosilylation of a pendant silyl ether (35). This process provides an unambiguous route to geometrically defined vinyl silanes having an oxygen function. This strategy, as illustrated in Scheme 14, is exemplified for the preparation of stereo defined homoallylic alcohols.

In particular, the cyclic siloxane 78 (where R is CH$_3$—) derived from 3-pentyn-ol (211, where R is CH$_3$—) was examined to illustrate the combination of intramolecular hydrosilylation and cross-coupling of this invention. Silylation of the alkynol with diisopropylchlorosilane provided a silyl ether in good yield which was then subjected to intramolecular hydrosilylation using a catalytic amount of Speier's catalyst:

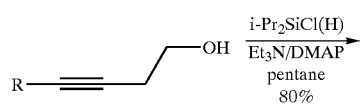

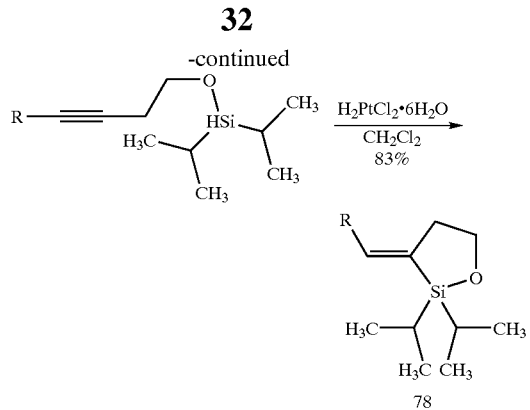

Palladium cross-coupling reaction of 78 with various aryl iodides are examined in Table 15, discussed above. Attempts to extend the intramolecular hydrosilyation to dimethyl siloxanes resulted in the generation of undesired polymeric materials. A practical solution to this problem was the establishment of a one-pot protocol that obviated the isolation and purification of delicate silyl ethers and siloxanes and improved overall efficiency of the process.

In this process a homopropargyl alcohol (e.g., 211) is treated with a silylating agent, tetramethyl disilazane (TMDS). The product (not isolated) is dissolved in THF in the presence of a platinum catalyst to facilitate intramolecular silylation ring closure. Cross-coupling was then carried out with the siloxane ring closure product (also not isolated). The results of the one-pot arylation of homopropargyl alcohols are shown in Table 26. As indicated in the table, increased loading of Pd(dba)$_2$ to 10 mol % resulted in significant improvement in rate and yield of the cross-coupling product.

It is believed that residual TMDS, which may poison the palladium catalyst, is detrimental to the cross-coupling reaction. TMDS is preferably removed (if possible in view of the volatility of the silyl ether) by evaporation upon completion of silylation. When a higher molecular weight alcohol (e.g., 3-octyn-1-ol) was used as the starting material, TMDS could be easily removed and cross-coupling was effectively promoted with lower levels of Pd catalyst (5 mol % Pd(dba)$_2$).

The advantages of the one-pot procedure are clear: (1) ease of experimental protocol, (2) no need to add aryl iodide portionwise to avoid homocoupling, (3) intermediate silyl ethers need not be isolated, and (4) superior overall yields. However, the multi-stage procedure in which the isopropyl substituted siloxane 78 is isolated is superior in providing for stereospecificity in the products. In the one-pot procedure using the dimethylsiloxane a small amount of the other stereoisomer (the (Z)-isomer in the examples of Table 26) was observed. All attempts to suppress the formation of this isomer where unsuccessful. The minor product was not eliminated, for example, by decreasing the reaction concentration for hydrosilylation or by changing the hydrosilylation catalyst.

These results demonstrate the expanded synthetic potential of the silicon-based cross-coupling reaction of this invention. The silicon atom has served in the following capacities: as a temporary protecting group for the hydoxyl function, as a temporary tether to fix the geometry of the vinyl silane and as the locus for directing formation of a new C—C bond. In a very mild and environmentally friendly manner, homopropargyl alcohols are elaborated stereospecifically to trisubstituted homoallylic alcohols in good yields. These structures are often encountered in natural products and also are useful synthetic intermediates.

EXAMPLE 1

General Experimental

Analytical thin-layer chromatography was performed on Merck silica gel pates with QF-254 indicator Visualization was accomplished with UV light and/or potassium permanganate. Methanol was of reagent grade and used as received; other solvents for chromatography and filtration were technical grade and distilled from the indicated drying agents: hexane and pentane ($CaCl_2$) ethyl acetate ($K_2CO_3$). Column chromatography was performed using Science 230–400 mesh silica gel or ICN silica RP C18 (32–63 μm) 60A.

Analytical capillary gas chromatography (GC) was performed using a Hewlett Packard 5890 Series II gas chromatograph fitted with a flame ionization detector ($H_2$ carrier gas, 1 mL/min) and an HP-5 (50-m, 0.2 mm) cross-linked phenyl methyl silicone capillary column. The injector temperature was 225° C., the detector temperature was 300° C. Oven temperature and head pressures specified. Retention times ($t_R$) and integrated ratios were obtained from Hewlett Packard 3393A integrators.

Kugelrohr distillations were performed on a Büchi GKR-50 Kugelrohr; boiling points (bp) corresponding to uncorrected air-bath temperature. All commercial reagents were purified by distillation prior to use.

The solvents used in reactions were reagent grade and distilled from the indicated drying agents under a nitrogen atmosphere: acetonitrile: $CaH_2$, tetrahydrofuran (THF):and diethyl ether ($Et_2O$): sodium metal/benzophenone ketyl. The solvents used for extraction and chromatography were technical grade and distilled from the indicated drying agents: hexane, pentane, dichloromethane ($CH_2Cl_2$): ($CaCl_2$); ethyl acetate:$K_2CO_3$. Unless otherwise noted, all nonaqucous reactions were performed in oven-and/or flame-dried glassware under an atmosphere of dry nitrogen.

Tetrabutylammonium fluoride (TBAF) solution in THF (1.0 M) was made from TBAF trihydrate solid bought from Fluka. Tri-t-butylphosphine solution in THF (1.0 M) was made from tri-t-butylphosphine purchased from Strem. 1,1-Dichlorosilacyclobutane (1) was prepared according to literature.[5]

Preparation of (E)-1-(1-Heptenyl)-1-methylsilacyclobutane ((E)21)

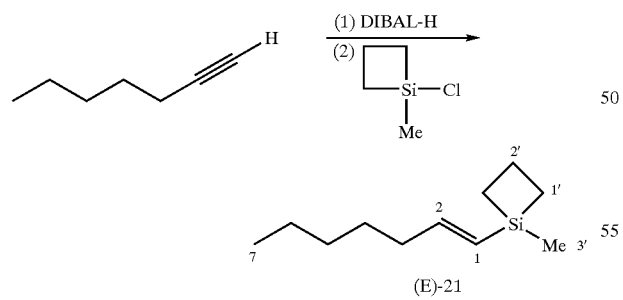

(E)-21

To a solution of 1-heptyne (2.62 mL, 1.91 g, d=0.7328, 20.0 mmol) in n-hexane (7 mL) was added a solution of DIBAL-H (20 mL, 1.0 M in n-hexane, 20.0 mmol 1.0 equiv) at −78° C. The reaction mixture was heated at 50° C. for 2 h, then was cooled to 0° C. 1-Chloro-1-methylsilacyclobutane (2.41 g, 20.0 mmol, 1.0 equiv) was added dropwise with syringe to the reaction mixture at 0° C., which was stirred for 48 h at 50° C. Cold water (1.28 mL, 71 mmol, 3.5 equiv) was added to the action solution carefully at 0° C. The resulting white suspension was filtered through Celite and the filtrate was concentrated in vacuo. The crude product was purified by column chromatography ($SiO_2$, pentane) and distillation to afford 2.96 g (81%) of (E)-1 as a colorless oil. 1-Methyl-(1-heptynyl)silacyclobutane (145 mg, 8%) was also isolated after column chromatography.

Preparation of 1-(1-Heptynyl)-1-methylsilacyclobutane

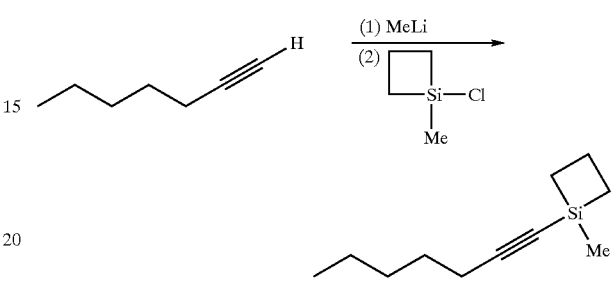

To a solution of 1-heptyne (1.31 mL, d=0.7238, 0.960 g, 10.0 mmol) in $Et_2O$ (10 mL) was added a solution of MeLi (9.43 mL, 1.06 M in $Et_2O$, 1.0 equiv) at −78° C. After being stirred for 3 h, 1-chloro-1-methylsilacyclobutane (1.16 mL, 1.0 equiv) was added dropwise to the reaction solution at the same temperature, which was then stirred for another 5 h. The reaction mixture was quenched with $H_2O$ (10 mL) and then was extracted with pentane (3×25 mL). The combined organic layers were dried ($MgSO_4$) and concentrated in vacuo to afford the crude product, which was purified by column chromatography ($SiO_2$, pentane) and Kugelrohr distillation to afford 1.66 g (92%) of 1-(1heptynyl)-1-methylsilacyclobutane as colorless oil Preparation of (Z)-1-(1-Heptenyl)-1-methylsilacyclobutane (Z)-21

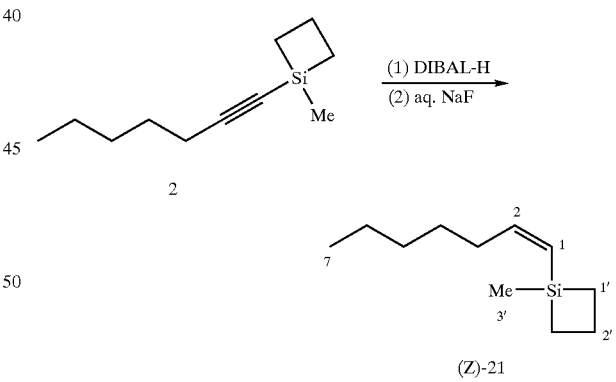

(Z)-21

Neat DIBAL-H (1.93 mL, 1.52 g, d=0.789, 10.7 mmol, 1.2 equiv) was added to a solution of 1-(1-hexynyl)-1-methylsilacyclobutane (1.62 g, 9,0 mmol) in hexane (14 mL) and $Et_2O$ (9 mL) at 0° C. The mixture was stirred for 3 h at 0° C., 9 h at rt, and then was diluted with $CH_2Cl_2$ (40 mL). Solid NaF (3.21 g, 76.4 mmol, 8.5 equiv) was added, followed by $H_2O$ (2.9 mL, 161 mmol, 17.8 equiv) and the suspension was stirred for 3 h, then was filtered and the filtrate was concentrated in vacuo. The crude product was purified by column chromatography ($SiO_2$, pentane) and Kugelrohr distillation to afford 1.35 g (82%) of (Z)-1 as a colorless oil.

General Procedure: Palladium Catalyzed Cross Coupling Reaction of Alkenyl Silanes with Aryl or Alkenyl Halides To the neat alkenylsilane (1.1–1.5 equiv) was added a solution of tetra n-butylammonium fluoride (TBAF) (1.0 M in THF 3.0 equiv). The initial exotherm was allowed to subside and the solution was stirred until it returned to rt, (ca. 10 min). The aryl iodide or alkenyl halide (1.0 equiv) was added to the solution followed by the palladium catalyst (2.5 or 5 mol %) and the mixture was stirred at rt for 10 min–7 h. The reaction mixture was filtered through a short silica gel column (20 g). After concentration in vacuo, the residue was purified by column chromatography (Reverse Phase C18 or SiO$_2$) and distillation to afford the product.

Preparation of (E)-1-Heptenylbenzene

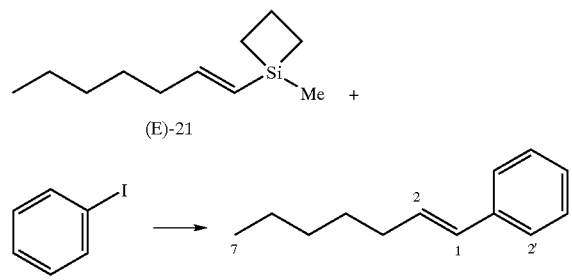

Following the General Procedure, (E)-21 (201 mg, 1.1 mmol, 1.1 equiv), a solution of TBAF (3.0 mL, 1.0 M in THF, 3.0 mmol, 3.0 equiv), iodobenzene (112 μL, 205 mg, d=1.831, 1.0 mmol) and Pd(dba)$_2$ (29 mg, 0.05 mmol, 0.05 equiv) were stirred at rt for 10 min, and the mixture was filtered through SiO$_2$. Purification of the crude product by column chromatography (RP C18, MeOH/H$_2$O, 9/1) and Kugelrohr distillation afforded 159 mg (91%) of (E)-1-heptenyl-benzene as a colorless oil.

Preparation of (E)-2-(1-Heptenyl)thiophene ((E)-3c)

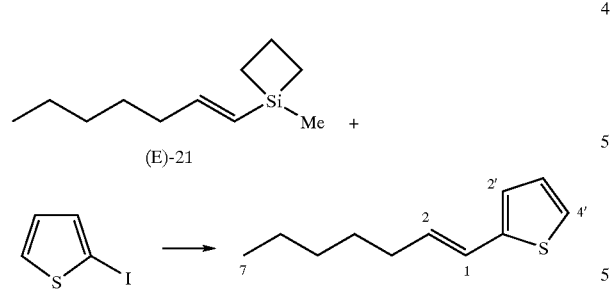

Following the General Procedure, (E)-21 (219 mg, 1.2 mmol, 1.2 equiv), a solution of TBAF (3 mL, 1.0 M in THF, 3.0 equiv), 1-iodothiophene (111 μL, 211 mg, d=1.902, 1.0 mmol) and Pd(dba)$_2$ (29 mg, 0.05 mmol, 0.05 equiv) were stirred at rt for 3 h, and the mixture was filtered through SiO$_2$. Purification of the crude product by column chromatography (RP C18, MeOH/H$_2$O, 9/1) and Kugelrohr distillation afforded 160 mg (89%) of (E)-2-(1-heptenyl)thiophene as a colorless oil.

Preparation of (E,E)-1,3-Nonadienylbenzene

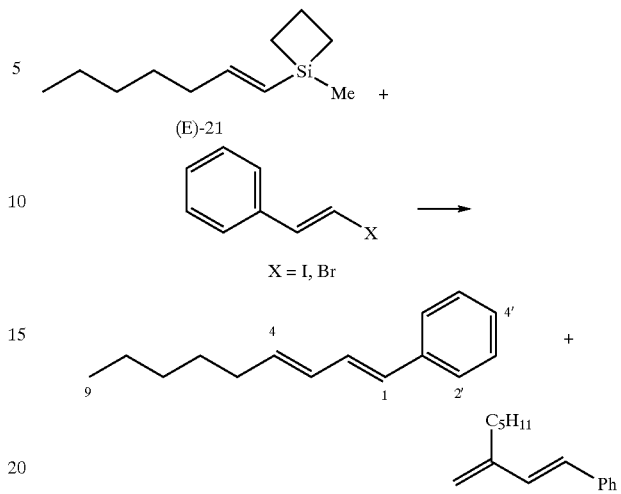

Following the General Procedure, (E)-21 (201 mg, 1.1 mmol, 1.1 equiv), a solution of TBAF (3 mL, 1.0 M in THF, 3.0 equiv), (E)-β-iodostyrene (231 mg, 1.0 mmol) and Pd(dba)$_2$ (29 mg, 0.05 mmol, 0.05 equiv) were stirred at rt for 10 min and then was filtered through SiO$_2$. Purification of the crude product by column chromatography (RP C18, MeOH/H$_2$O, 9/1) and Kugelrohr distillation afforded 146 mg (73%) of (E,E,)-1,3-nonadienylbenzene as a colorless oil.

Following the General Procedure, (E)-21 (274 mg, 1.5 mmol, 1.5 equiv), a solution of TBAF (3 mL, 1.0 M in THF, 3.0 equiv), (E)-β-bromostyrene (128 μL, 183 mg, d=1.427, 1.0 mmol) and (allylPdCl)$_2$ (9 mg, 0.025 mmol, 0.025 equiv) were stirred at rt for 1 h and the mixture was filtered through SiO$_2$. Purification of the crude product by column chromatography (RP C18, MeOH/H$_2$O, 9/1) and Kugelrohr distillation afforded 160 mg (80%) of (E,E)-1,3-nonadienylbenzene as a colorless oil.

Preparation of (Z,Z)-5,7-Tridecadien-1-ol

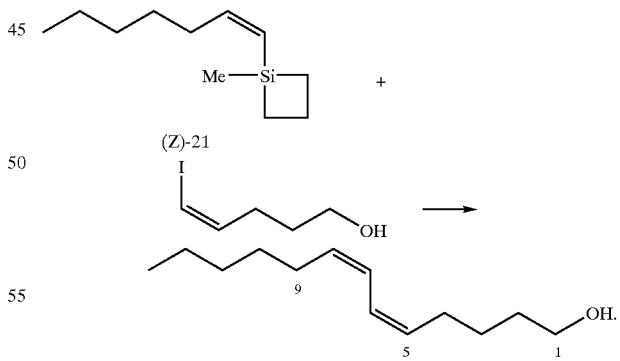

Following the General Procedure, (Z)-21(219 mg, 1.2 mmol, 1.2 equiv), a solution of TBAF (3 mL, 1 M in THF, 3 equiv), (Z)-6-iodo-5-hexen-1-ol (226 mg, 1.0 mmol) and (allylPdCl)$_2$ (9 mg, 0.025 mmol, 0.025 equiv) were stirred at rt for 6 h and the mixture was filtered through SiO$_2$. Purification of the crude product by column chromatography (SiO$_2$, hexane/EtOAc, 41) and Kugelrohr distillation afforded 128 mg (65%) of (Z,Z)-4c as colorless oil.

Literature Preparations

The following compounds were prepared by literature methods: 1-chloro-1-methylsilacyclobutane, (E)-β-bromostyrene[1], (E)-β-iodostyrene[2], (E)-6-iodo-5-hexenol[3] and (Z)-6-iodo-5-hexenol[4].

References for Example 1:
(1) Lloyd-Jones, G. C. Butts, C. P. *Tetrahedron* 1998, 54, 901.
(2) Suzuki, H.; Aihara, M.; Yamamoto, H.; Takamoto Y.; Ogawa, T *Synthesis* 1988, 236.
(3) Stille, J. K; Simson, J. H. *J. Am. Chem. Soc.* 1987, 109, 2138.
(4) Stille, J. K.; Groh, B. L.; *J. Am. Chem. Soc.* 1987, 109, 813.
(5) (a) Denmark, S. E.; Griedel, B. D.; Coe, D. M.; Schnute, M. E. *J. Am. Chem. Soc.* 1994, 116, 7026. (b) Laane, J. *J. Am. Chem. Soc.* 1967, 89, 1144.

EXAMPLE 2

1-Chloro-1-(4'-methoxyphenyl)silacyclobutane B

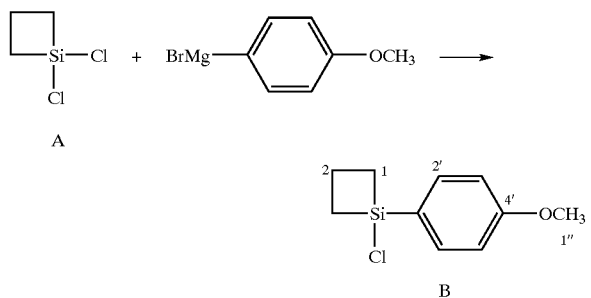

4-Methoxyphenylmagnesium bromide solution in Et$_2$O was prepared in conventional method and titrated.[2] To a solution of $_A$ (5.61 g, 39.7 mmol, 1.2 equiv) in Et$_2$O (80 mL) was added 4-methoxyphenylmagnesium bromide (24.0 mL, 1.38 M, 33.1 mmol) dropwise over 1 h at 0° C. Then the reaction mixture was allowed to warm up to room temperature and was stirred overnight. After Schlenk filtration, all the solvent was removed by simple distillation and the residue was purified by fractional distillation under vacuum to afford 5.21 g (73%) of $_B$ as a colorless oil.

1-Fluoro-1-(4'-methoxyphenyl)silacyclobutane C

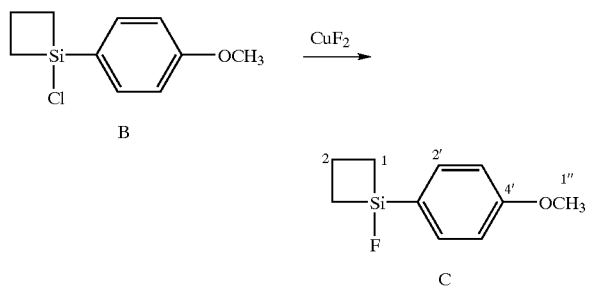

To a solution of $_B$ (2.98 g 14.0 mmol) in Et$_2$O (60 mL) was added CuF$_2$ (0.71 g, 7.0 mmol, 0.5 equiv) at 0° C. The reaction mixture was allowed to warm up to room temperature and was stirred overnight. The solid was removed by quick filtration through celite and the solvent was distilled off by simple distillation. The residue was then purified by fractional distillation under vacuum to afford 1.98 g, (72%) of C as a colorless oil.

1-Chloro-1-(2'-methylphenyl)silacyclobutane D

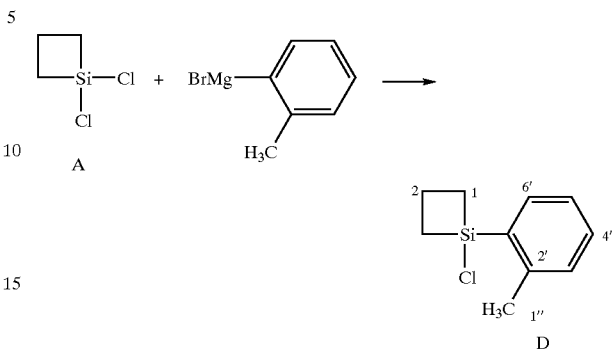

2-Methylphenylmagnesium bromide was prepared by adding a Et$_2$O solution (40 mL) of 2-methylbromobenzene (9.89 g, 57.8 mmol) to Mg (1.55 g, 63.58 mmol, 1.1 equiv) over 1 h and refluxing for 2 h. After cooled to room temperature, the resulted solution was added dropwise to a solution of $_A$ (8.15 g, 57.8 mmol, 1.0 equiv) in Et$_2$O (80 mL) at 0° C. The reaction mixture was allowed to warm up to room temperature and was stirred overnight. After Schlenk filtration, all the solvent was removed by simple distallation and the residue was purified by fractional distillation under vacuum to afford 8.53 (78%) of D as a colorless oil.

Palladium Catalyzed Cross-coupling Reaction of Arylsilanes with Aryl Iodides Representative Procedure: Preparation of 4-Methoxybiphenyl E

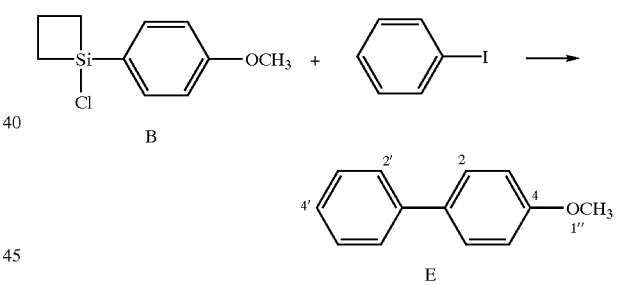

The reaction of arylsilane B and iodobenzene is representative. To the neat $_B$ (2.55 mg, 1.2 mmol, 1.2 equiv) was added a solution of tetra n-butylammonium fluoride (TBAF) (3.6 ml, 1.0 M in THF, 3.6 mmol, 3.6 equiv). The initial exotherm was allowed to subside and the solution was stirred until it returned to rt, (ca. 10 min). Iodobenzene (204 mg, 1.0 mmol) was added to the solution followed by tri(t-butyl)phosphine (0.2 mL, 1.0 M in THF, 0.2 mmol, 0.2 equiv) and [allylPdCl]$_2$ (9.1 mg, 2.5 mol %). The mixture was to reflux for 1 h. After being cooled to rt, the reaction mixture was treated with H$_2$O (10 mL) and extracted with CH$_2$C$_2$ (3×25 mL). The combined organic layers were dried (Na$_2$SO$_4$) and concentrated in vacuo. The crude product was further purified by column chromatography (SiO$_2$, hexane to hexane/EtOAc,50/1) to afford 0.167 g (91%) of $_E$ as a white solid.

References for Example 2:
(1) Watson, S. C.; Eastham, J. F. *J. Organomet. Chem.* 1967, 9, 165.

EXAMPLE 3

Preparation of (E)-Dimethyl-(1-heptenyl)silanol (E)-50

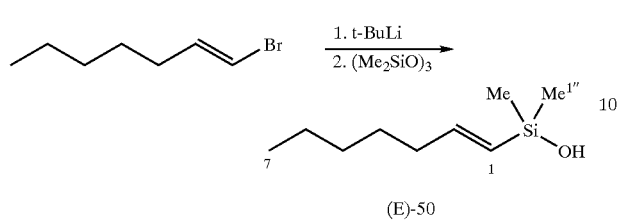

(E)-50

To a solution of (E)-1-bromo-1-heptene (5.313 g, 30.0 mmol) in dry ether (30 mL) under dry $N_2$ at −78° C., t-butyllithium (38.7 mL, 60 mmol, 1.55M) was added over 10 min. The reaction mixture was stirred at −78° C. for 1 h. The hexamethylcyclotrisiloxane (2.225 g, 10.0 mmol) in dry ether (30 mL) was then added over 5 min at −78° C. The reaction was warmed to room temperature and stirred for 24 h. The solution was then cooled to 0° C. and quenched with water (30 mL). The aqueous phase was extracted with ether (3×10 mL) and the combined organic phases were washed with water (1×10 mL) and brine (3×30 mL). The organic layer was dried with magnesium sulfate (anhydrous) and filtered. The solvent was then evaporated in vacuo to give a yellow oil which was purified by distillation to afford 3.836 g (74%) of (E)-50 (3.836 g, 74%) as a colorless oil.

Preparation of (Z)-Dimethyl-(1-heptenyl)silanol (Z)-50

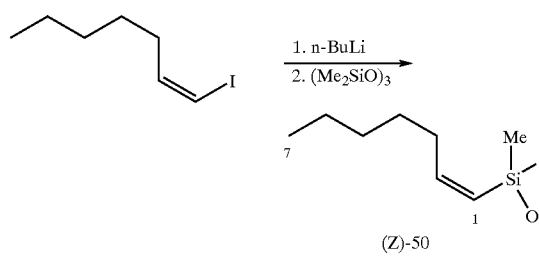

(Z)-50

To a solution of (Z)-1-iodo-1-heptene (2.241 g, 10.0 mmol) in dry ether (30 mL) under dry $N_2$ at −78° C. n-butyllithium (6.1 mL, 10 mmol 1.64M) was added over 10 min. The reaction mixture was stirred at −78° C. for 30 min. The hexamethylcyclotrisiloxane (742 mg, 3.3 mmol) in dry ether (10 mL) was then added over 5 min at −78° C. The reaction was warmed to room temperature and stirred for 24 h The solution was then cooled to 0° C. and was quenched with water (5 mL). The aqueous phase was extracted with ether (3×10 mL) and the combined organic phases were washed with water (1×10 mL) and brine (3×30 mL). The organic layer was dried with magnesium sulfate (anhydrous) and filtered. The filtrate was then evaporated in vacuo to give a yellow oil which was purified by distillation to afford 1.344 g (78%) of (Z)-50 as a colorless oil. Repented distillation provided analytically pure material.

Preparation of (E)-Diisopropyl-(1-heptenyl)silanol (E)-A-2

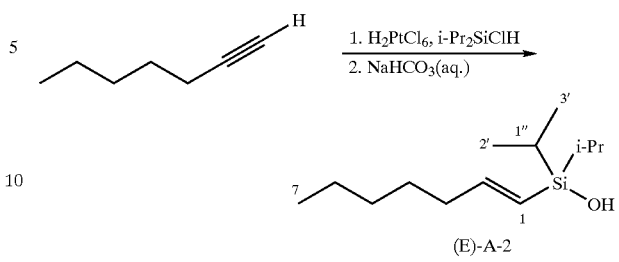

(E)-A-2

Hexachloroplatinic acid (26.6 mg, 65 μmol, 0.005 equiv) was dissolved in 2-propanol (1 mL) and diethyl ether (30 mL) in a dry two-neck, round-bottom flask equipped with a stir bar and a reflux condenser under an atmosphere of dry argon. Chlorodiisopropylsilane (2.155 g, 14.3 mmol, 1.1 equiv) was then added and the mixture was heated to reflux. A solution of 1-heptyne (1.250 g, 13.0 mmol) in dry ether (10 mL) was then added dropwise over 10 min, at a rate to maintain reflux of the reaction mixture. After the addition was complete, the mixture was heated in an oil bath to reflux for 4 h. After cooling to room temperature the solvent was evaporated in vacuo and the residual oil was distilled (114° C. at 6 mmHg) to give the chlorosilane (2.682 g, 83.6%) as a colorless liquid.

The intermediate chlorosilane (2.731 g, 11.1 mmol) was dissolved in ether (20 mL) and saturated aqueous sodium bicarbonate solution (10 mL) was added. The mixture was stirred at room temperature for 30 min and was then poured into pentane (30 mL). The aqueous phase was washed with pentane (3×10 mL). The combined organic phases were then washed with water (3×10 mL) and brine (2×10 mL). The organic layer was dried with $MgSO_4$, filtered and the solvents evaporated in vacuo to give a oil which was distilled twice to give(E)-A-2(2.408 g, 95.3%) as a colorless oil.

Preparation of (Z)-Diisopropyl-(1-heptenyl)silanol (Z)-B-2

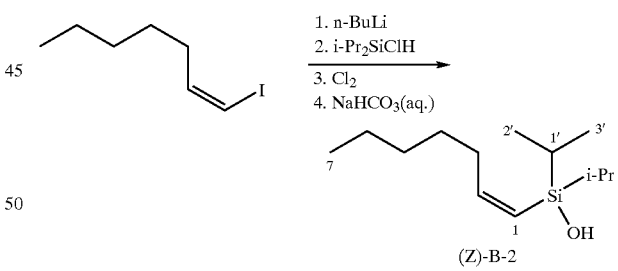

(Z)-B-2

To a solution of (Z)-1-iodo-1-heptene (2.017 g, 9.0 mmol) in dry ether (30 mL) under dry $N_2$ at −78° C. was added n-butyllithium (5.5 mL, 9 mmol, 1.64M, 1 equiv) over 10 min. The reaction mixture was stirred at −78° C. for 30 min whereupon a solution of chlorodiisopropylsilane (1.359 g, 9.0 mmol) in dry ether (10 mL) was, then added over 5 min at −78° C.

The mixture was allowed to warm to room temperature, was stirred for 12 h, then was poured into pentane (30 mL) and water (10 mL). The aqueous phase was extracted with pentane (3×10 mL) and the combined organic phases were washed with brine (3×10 mL). The organic layer was then dried with $MgSO_4$, filtered and the solvent evaporated to give 1.803 g of the intermediate hydridosilane as an oil. The crude intermediate was dissolved in CCl$_4$ (20 mL) and cooled with an ice bath. A solution of chlorine in CCl$_4$ (9.44 mL, 0.9 M, 8.5 mmol, 1.0 equiv) was then added dropwise and the mixture was stirred for 30 min further at 0° C. The solvent was then evaporated in vacuo and the residual oil was taken up in diethyl ether (20 mL). Saturated, aqueous sodium bicarbonate solution (10 mL) was added and the reaction was stirred at room temperature for 30 min and then poured into pentane (30 mL). The aqueous phase was washed with pentane (3×10 mL). The combined organic phases were then washed with water (3×10 mL) and brine (2×10 mL). The organic layer was dried with MgSO$_4$, filtered and the solvents evaporated in vacuo to give an oil which was distilled twice to afford the desired silanol $_{B-2}$ (1.742 g, 85%) as a colorless oil.

General Procedure: Palladium Catalyzed Cross Coupling Reaction of Alkenylsilanes with Aryl or Alkenyl Halides Tetrabutylammonium fluoride (2.0 mmol, 2.0 equiv) was dissolved in dry THF (2 mL) at room temperature under an atmosphere of dry nitrogen. The silanol (1.0–1.2 mmol) was added neat and the mixture was stirred for 10 minutes at room temperature. The corresponding aryl- or alkenyl iodide (1.0 mmol) was added to the mixture, followed by the palladium catalyst (2.5 mol % or 5 mol %) and the mixture was stirred at room temperature for 10 min–5 h. The reaction mixture, was then filtered through a short silica gel column (20 g). The plug war washed with diethyl ether (100 mL) and solvent was evaporated in vacuo. The residue was purified by column chromatography (Reverse Phase C18 or SiO$_2$. 25 g) to afford the corresponding product which was further purified by distillation.

Preparation of (1-E)-1-Heptenylbenzene[1] (E)-C-2

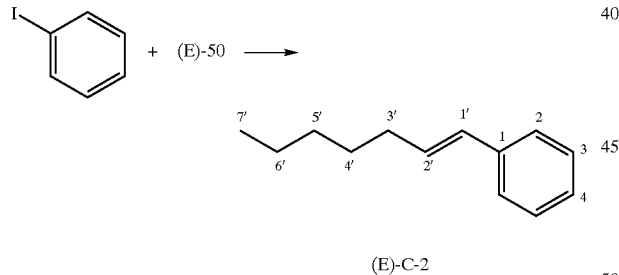

(E)-C-2

Following the general Procedure, (E)-50 (201 mg, 1.1 equiv) TBAF (631 mg, 2.0 equiv) in THF (2 mL), iodobenzene (112 μL, 1.0 mmol) and Pd(dba)$_2$ (29 mg, 0.05 equiv) was stirred at rt for 10 min, and then was filtered through SiO$_2$. Purification by column chromatography (RP C18, MeOH/H$_2$O=9/1) and Kugelrohr distillation afforded 159 mg (91%) of (E)-C-2 as colorless oil.

Preparation of (Z)-1-Heptenylbenzene[2] (Z)-C-2

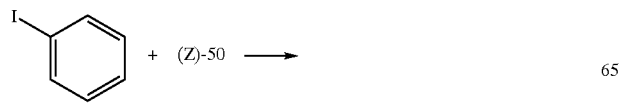

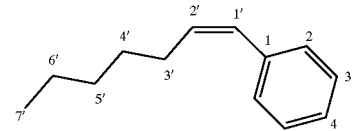

(Z)-C-2

Following the General Procedure, (Z)-50 (201 mg, 1.1 equiv). TBAF (631 mg, 2.0 equiv) in THF (2 mL), iodobenzene (112 μL, 1.0 mmol) and Pd(dba)$_2$ (29 mg, 0.05 equiv) was stirred at rt for 10 min and then was filtered through SiO$_2$. Purification by column chromatography (RP C18, MeOH$_2$O=9/1) and Kugelrohr distillation afforded 157 mg (90%) of (Z)-C-3 as colorless oil.

Preparation of (E)-1-(1-Heptenyl)naphthalene-$^3$,(E)-D-2

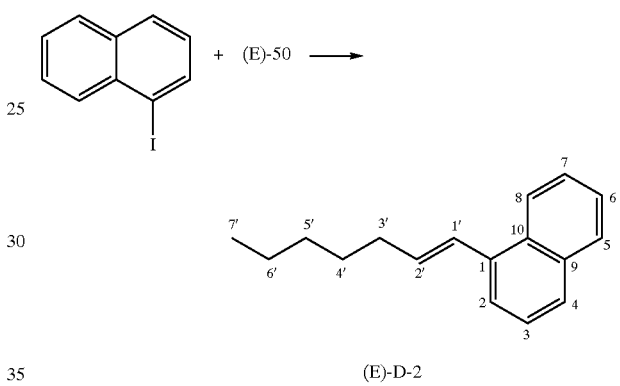

(E)-D-2

Following the General Procedure, (E)-50 (201 mg, 1.1 equiv). TBAF(631 mg, 2.0 equiv) in THF (2 mL), 1-iodonaphthalene (146 μL, 1.0 mmol) and Pd(dba)$_2$ (29 mg, 0.05 equiv) was stirred at rt for 30 min. and then filtered through SiO$_2$. Purification by column chromatography (RP C18, MeOH/H$_2$O=9/1) and Kugelrohr distillation afforded 199 mg (89%) of (E)-D-2 as colorless oil.

Preparation of (E)-1-(1-Heptenyl)naphthalene$^3$-(E)-D-3 Methanolic with Tetrabutylammonium Hydroxide

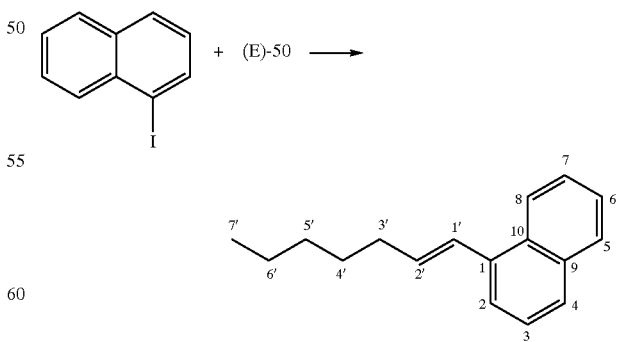

(E)-D-3

Following the General Procedure, (E)-50 (201 mg, 1.1 equiv). TBAOH (1.00 mL, 2.0 mmol, 2M in MeOH) in THF (1.0 mL), 1-iodonaphthalene (146 μL, 1.0 mmol) and Pd(dba)$_2$ (29 mg, 0.05 equiv) was stirred at rt for 30 min, and then filtered through SiO$_2$. Purification by column chromatography (RP C18, MeOH/H$_2$O=9/1) and Kugelrohr distillation afforded 170 mg (76%) of (E)-D-3 as colorless oil.

Preparation of (E)-4-(1-Heptenyl)acetophenone (E)-E-2

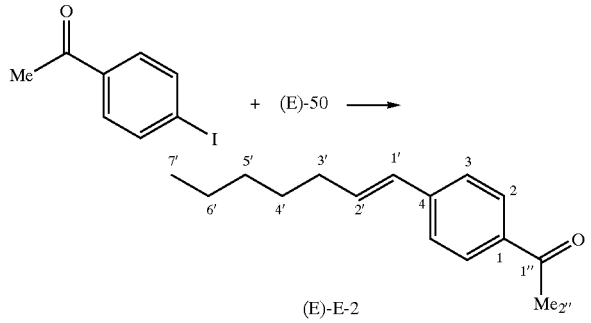

Following the General Procedure, (E)-50 (201 mg, 1.1 equiv) in TBAF (631 mg, 2.0 equiv) in THF (2 mL), 4'-iodoacetophenone (246 mg, 1.0 mmol) and Pd(dba)$_2$ (29 mg, 0.05 equiv) was stirred at rt for 10 min and then was filtered through SiO$_2$. Purification by column chromatography (RP C18, MeOH/H$_2$O=9/1) and Kugelrohr distillation afforded 201 mg (93%) of (E)-E-2 as colorless oil.

Preparation of (E)-4-(1-Heptenyl)acetophenone (E)-E-2 with 1 equivalent of TBAF

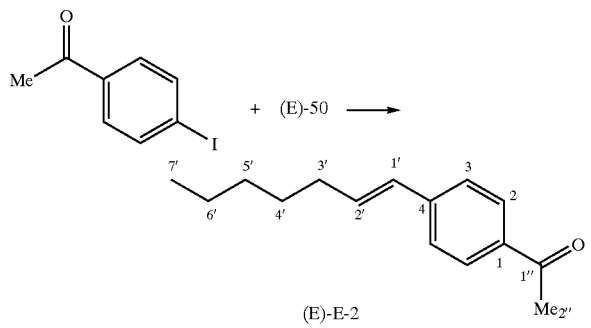

Following the General Procedure, (E)-50 (201 mg, 1.1 equiv), TBAF (1.00 mL, 1M in THF, 1.0 equiv) in THF (2 mL), 4'-iodoacetophenone (246 mg, 1.0 mmol) and Pd(dba)$_2$ (29 mg, 0.05 equiv) was stirred at rt for 60 min and then was filtered through SiO$_2$. Purification by column chromatography (RP C18, MeOH/H$_2$O=9/1) and Kugelrohr distillation afforded 188 mg (87%) of (E)-E-2 as colorless oil.

Preparation of (E)-4-(1-Heptenyl)acetophenone (E)-E-2 from 4-Bromoacetophenone

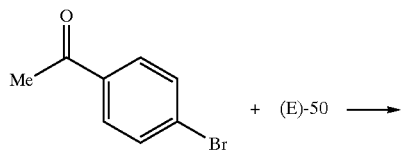

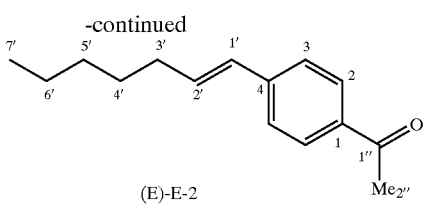

Following the General Procedure, (E)-50 (219 mg, 1.2 equiv), TBAF (631 mg, 2.0 equiv) in THF (2 mL) 4'-bromoacetophenone (199 mg, 1.0 mmol) and [allylPdCl]$_2$ (9.1 mg, 0.025 equiv) was stirred at rt for 120 min. An additional equivalent of TBAF (315 mg) and 1.25 mol % of [allylPdCl]$_2$ (4.5 mg, 0.013 equiv) was added and the reaction was stirred for one more hour. Filtration through SiO$_2$, followed by purification by column chromatography (RP C18, MeOH/H$_2$O=9/1) and Kugelrohr distillation afforded 160 mg (74%) of (E)-E-2 as colorless oil.

Preparation of (1E)-1-Heptenylbenzene[1] (E)-F-2 with di(iso-propyl)heptenylsilanol

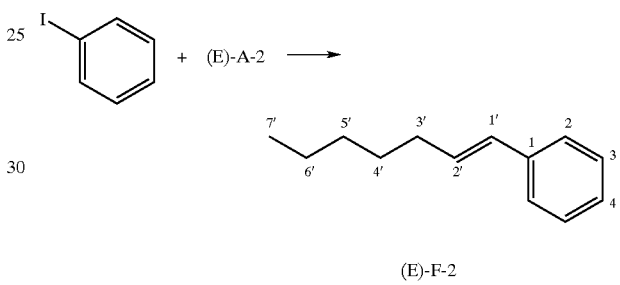

Following the General Procedure, (E)-A-2 (251 mg, 1.1 equiv), TBAF (631 mg, 2.0 equiv) in THF (2 mL), iodobenzene (112 μL, 1.0 mmol) and Pd(dba)$_2$ (29 mg, 0.05 equiv) was stirred at rt for 10 min, and then was filtered through SiO$_2$. Purification by column chromatography (RP C18, MeOH/H$_2$O=9/1) and Kugelrohr distillation afforded 143 mg (82%) of (E)-F-2 as colorless oil.

Preparation of (Z)-1-(1-Heptenyl)naphthalene (Z)-G-2 with di(isopropyl)heptenylsilanol

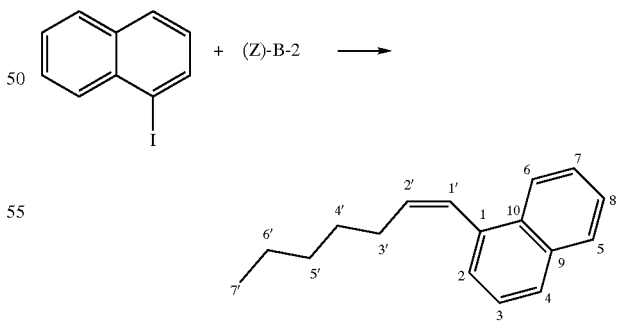

Following the General Procedure, (Z)-B-2 (251 mg, 1.1 equiv). TBAF (631 mg, 2.0 equiv) in THF (2 mL), 1-iodonaphthalene (146 μL, 1.0 mmol) and Pd(dba)$_2$ (29 mg, 0.05 equiv) was stirred at rt for 30 min, and then filtered through SiO$_2$. Purification by column chromatography (RP C18, MeOH/H$_2$O=9/1) and Kugelrohr distillation afforded 178 mg (79%) of (Z)-G-2 as colorless oil.

Preparation of (E)-1-(1-Heptenyl)naphthalene[3] (E)-H-2 with di(isopropyl)heptenylsilanol and with Methanolic Tetrabutylammonium Hydroxide

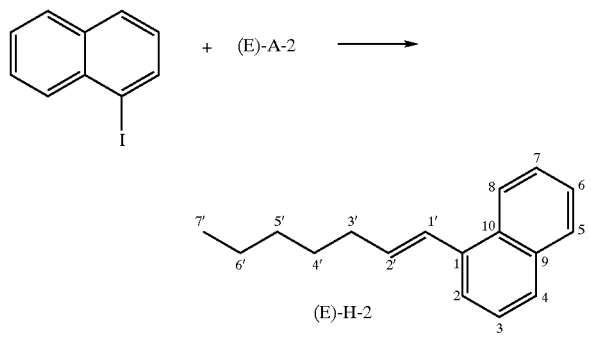

Following the General Procedure, (E)-A-2 (251 mg, 1.1 equiv), TBAOH (1.00 mL, 2.0 mmol, 2M in MeOH) in THF (1.0 mL), 1-iodonaphthalene (146 µL, 1.0 mmol) and Pd(dba)$_2$ (29 mg, 0.05 equiv) was stirred at rt for 30 min, and then filtered through SiO$_2$. Purification by column chromatography (RP C18, MeOH/H$_2$O=9/1) and Kugelrohr distillation afforded 174 mg (78%) of (E)-H-2 as colorless oil.

Preparation of (Z,Z)-5,7-Tridecadien-1-ol[4] (Z,Z)-I-2

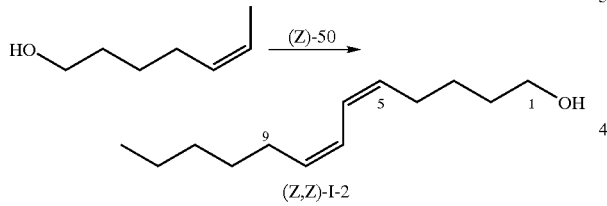

Following the General Procedure, (Z)-50 (219 mg, 1.2 equiv). TBAF (631 mg, 2.0 equiv) in THF (2 mL), (Z)-6-iodo-5-hexen-1-ol (226 mg, 1.0 mmol) and (allylPdCl)$_2$ (9 mg, 0.025 eq) was stirred at rt for 6 h and then was filtered through SiO$_2$. Purification by column chromatography (SiO$_2$, n-hexane/EtOAc=4/1) and Kugelrohr distillation afforded 126 mg (64%) of (Z,Z)-I-2 as colorless oil.

Preparation of (Z,Z)-5,7-Tridecadien-1-ol[4] (Z,Z)-I-2 with di(isopropyl)heptenylsilanol [DW-VII-33]. (Table 3, entry 6)

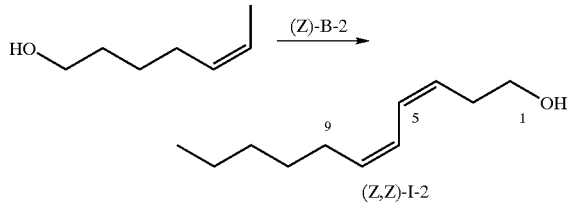

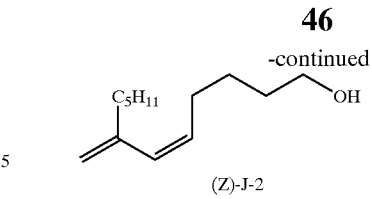

Following the General Procedure, (Z)-B-2 (274 mg, 1.2 equiv). TBAF (631 mg, 2.0 equiv) in THF (2 mL), (Z)-6-iodo-5-hexen-1-ol (226 mg, 1.0 mmol) and (allylPdCl)$_2$ (9 mg, 0.025 eq) was stirred at rt for 6 h and then was filtered through SiO$_2$. Purification by column chromatography (SiO$_2$, n-hexane/EtOAc=4/1) and Kugelrohr distillation afforded 134 mg (68%) of (Z,Z)-I-2 as colorless oil.

References for Example 3:

(1) Yanaginsawa, A; Momura, N; Yamamoto, H. Tetrahedron 1994, 50, 6017.

(2) Kauffmann, T.; Rauch, E; Schulz, J; Chem. Ber. 1973,106, 1612.; Just, G.; O'Connor, B. Tetrahedron Letters, 1985,26, 1799.

(3) Negish, E.; Takahashi, T.; Baba, S.; Van Horn, D. E.; Okukado, N. J Am. Chem, Soc. 1987, 109, 2393.

(4) Matikainerr, J.; Kaltia, S.; Hamalainen, M.; Hase, T. Tetrahedron, 1997, 53, 4531.

EXAMPLE 4

Cross-coupling of (α-Alkoxyvinyl) Silanols

Preparation of [2-(5,6-Dihydro-4H-pyranyl)] dimethylsilanol

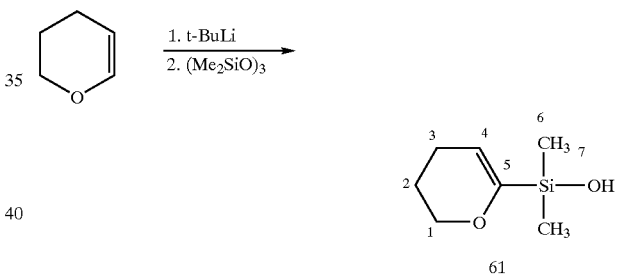

To a solution of t-butyllithium (10.0 mL, 14 mmol, 1.4 M in heptane) under dry N$_2$ at −78° C. was added THF (1.15 mL, 1.4 mmol). The resulting yellow suspension was stirred at −78° C. for 10 min, then 3,4-dihydro-2H-pyran (1.30 mL, 14 mmol, 1.0 equiv) was added. The mixture was allowed to warm to 0° C. and was stirred for 1.5 h whereby a colorless solution was obtained.

After cooling the solution to −78° C., a solution of hexamethylcyclotrisiloxane (1.04 g, 4.6 mmol, 0.33 equiv) in dry THF (2.0 mL) was added over 5 min at −78° C. The mixture was allowed to warm to 0° C. and was stirred for at that temperature 1.5 h. The mixture was then allowed to warm to room temperature and was stirred for 1.5 h during which time a white suspension formed. The solution was then cooled to 0° C. and was quenched with water (20 mL). The aqueous phase was exchanged with ethyl acetate (5×20 mL) and the combined organic phases were washed with water (1×20 mL) and brine (1×20 mL). The combined organic layers were dried over anhydrous sodium sulfate and were filtered. The filtrate was then evaporated in vacuo to give a yellow oil which was purified by column chromatography (silica gel, hexane/ethyl acetate, 7/1) and by distillation to afford 1.51 g (68%) of 61 as a colorless oil.

Reaction of Ethyl 4-Iodobenzoate with Silanol 61 to form Ethyl 4-[2-(5,6-Dihydro-4H-pyranyl)] benzoate 62a

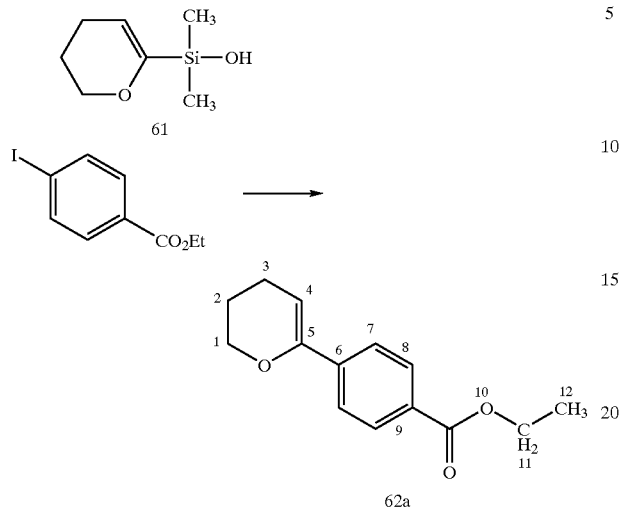

Following the General Procedure, 61 (190 mg, 1.2 mmol 1.2 equiv), was dissolved in a solution of TBAF in THF (1.0 M, 2.0 mL, 2.0 mmol, 2.0 equiv) and was stirred for 10 min at rt. Ethyl 4-iodobenzoate (0.166 mL, 1.0 mmol) and [allylPdCl]$_2$ (9 mg, 0.025 equiv) were added. The suspension was stirred at rt for 10 min and then was filtered through a short plug of SiO$_2$. Purification of the residue by column chromatography (SiO$_2$, hexane/EtOAc, 20/1) and recrystallization from hexane afforded 195 mg (84%) of 62a as a colorless oil.

General Procedure for Coupling of Silanols

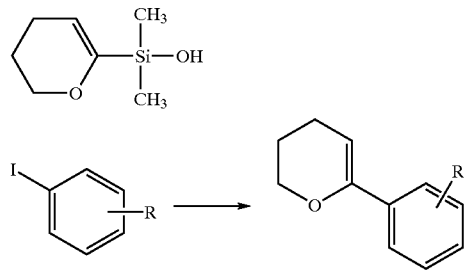

To the organosilanol (1.2 mmol) was added a solution tetrabutylammonium fluoride (TBAF) in THF (1.0 M, 2.0 mL, 2.0 mmol). The aryl iodide or vinyl iodide (1.0 mmol, 1.0 equiv) was added to the mixture followed by the palladium catalyst (5 mol % of Pd) and the mixture was stirred at room temperature for 10 min to 4 h. The mixture was then filtered through a short plug of silica gel or alumina (10 g). The plug was washed with diethyl ether (50 mL) and the solvent was evaporated in vacuo. Purification of the residue by column chromatography afforded the coupling product which was further purified by Kugelrohr distillation or crystallization.

Reaction of Ethyl (E)-2-Iodopropenoate with Silanol 61 to form Ethyl (E)-3-[2-(5,6-Dihydro-4H-pyranyl)]propenoate A-3

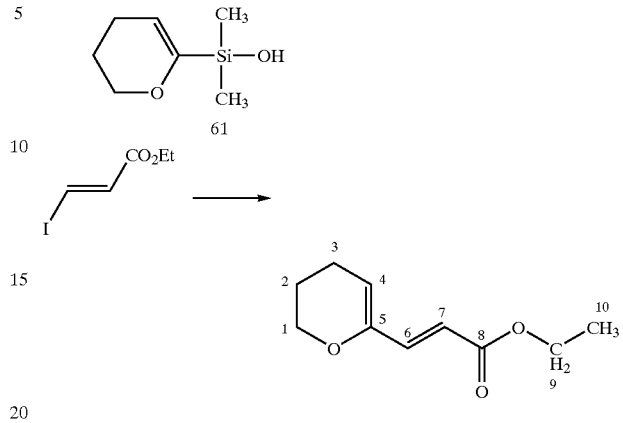

Following the General Procedure, 61 (190 mg, 1.2 mmol, 1.2 equiv), was dissolved in a solution of TBAF in THF (1.0 M, 2.0 mL, 2.0 mmol, 2.0 equiv) and was stirred for 10 min at rt. Ethyl (E)-2-iodopropenoate (226 mg, 1.0 mmol) and [allylPdCl]$_2$ (9 mg, 0.025 equiv) were added. The suspension was stirred at rt for 10 min and then was filtered through a short plug of SiO$_2$. Purification of the residue by column chromatography (Al$_2$O$_3$, hexane/Et$_2$O, 10/1) afforded 148 mg (81%) of A-3 as a colorless oil.

EXAMPLE 5

The Cross-coupling Reaction of (α-Alkoxyvinyl) Silyl Hydrides

Preparation of [2-(5,6-Dihydro4H-pyranyl)] diisopropylsilane 84

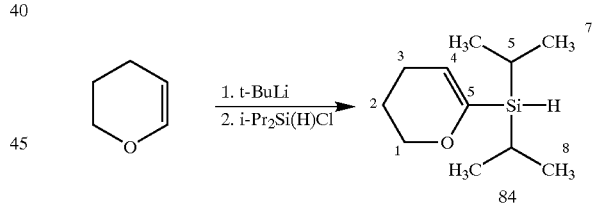

To a solution of t-butyllithium (5.0 mL, 8.0 mmol, 1.6 M in heptane) under dry N$_2$ at −78° C. was added THF (0.65 mL, 8.0 mmol, 1.0 equiv). The resulting yellow suspension was stirred at −78° C. for 10 min, then 3,4-dihydro-2H-pyran (1.30 mL, 8.0 mmol, 1.0 equiv) was added. The mixture was allowed to warm to 0° C. and stirred for 1.5 h whereby a colorless solution was obtained.

After cooling the solution to −78° C., chlorodiisopropylsilane (1.36 mL, 8.0 mmol, 1.0 equiv) was then added. The mixture was stirred for 1.5 h at −78° C., then was allowed to warm to room temperature and was stirred for 1.5 h during which time a white suspension formed. After addition of heptane 10 mL), the suspension was filtered through a short Plug of Celite. The solvent was then evaporated in vacuo to give a white suspension. After Kugelrohr distillation (130° C. at 0.6 mmHg), the colorless oil obtained was purified by column chromatography (silica gel, hexane) and was distilled again to give 1.20 g (75%) of 84 as a colorless oil.

Preparation of (1-Butoxyvinyl)diisopropylsilane 85

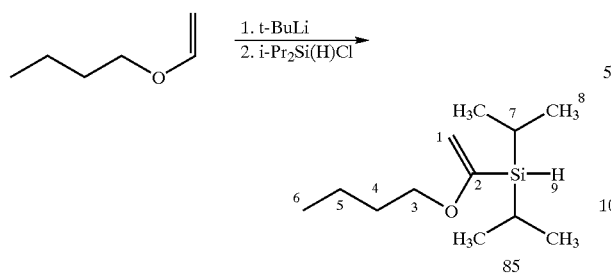

To a solution of t-butyllithium (5.0 mL, 7.5 mmol, 1.5 M in heptane) under dry $N_2$ at −78° C. was added THF (0.60 mL, 7.5 mmol, 1.0 equiv). The resulting yellow suspension was stirred at −78° C. for 10 min then n-butyl vinyl ether (0.97 mL, 7.5 mmol, 1.0 equiv) was added The mixture was allowed to warm to 0° C. and was stirred for 1.5 h whereby a colorless solution was obtained.

After cooling the solution to −78° C., chlorodiisopropylsilane (1.30 mL, 7.5 mmol, 1.0 equiv) was added. The mixture was stirred for 1.5 h at −78° C., was allowed to warm to room temperature and was stirred for 1.5 h during which time a white suspension was formed. After addition of heptane (10 mL), the suspension was filter through a short plug of Celite. The filtrate was then evaporated in vacuo) to give a white suspension. After Kugelrohr distillation (120° C. at 0.6 mmHg), the colorless oil obtained was purified by column chromatography (silica gel, hexane) and was distilled again to give 1.16 g (72%) of 85 as a colorless oil.

Preparation of 2-(4,5-Dihydrofuranyl)diisopropylsilane 86

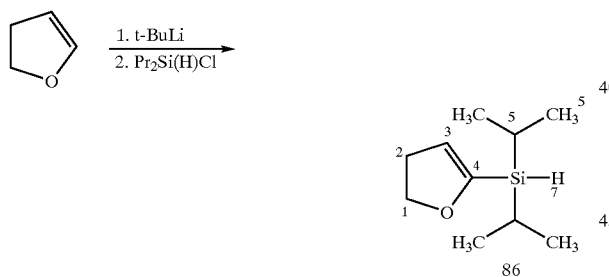

To a solution of t-butyllithium (5.0 mL, 7.5 mmol, 1.5 M in heptane) under dry $N_2$ at −78° C. was added THF (0.60 mL, 7.5 mmol, 1.0 equiv). The resulting yellow suspension was stirred at −78° C. for 10 min, then 2,3-dihydrofuran (0.567 mL, 7.5 mmol, 1.0 equiv) was added. The mixture was warmed to 0° C. and was stirred for 1.5 h whereby a white suspension was obtained.

After cooling the suspension to −78° C., chlorodiisopropylsilane (1.30 mL, 7.5 mmol, 1.0 equiv) was added. The mixture was stirred for 1.5 h at −78° C., was allowed to warm to room temperature and was stirred for 1.5 h. After addition of heptane (10 mL), the suspension was filtered through a short plug of Celite. The filtrate was then evaporated in vacuo to give a white suspension. After Kugelrohr distillation (120° C. at 0.6 mmHg), the colorless oil obtained was purified by column chromatography (silica gel, hexane) and was distilled again to give 987 mg (71%) of 86 as a colorless oil.

General Procedure for Coupling of Hydridosilanes

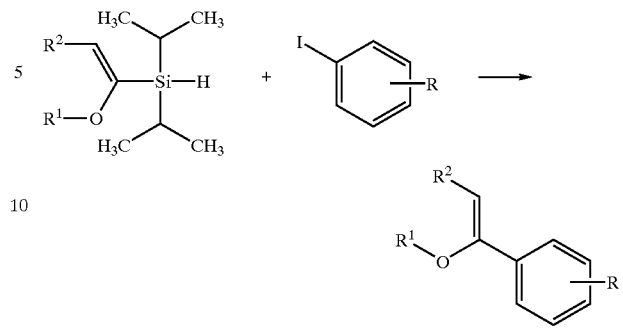

To the hydridosilane (1.2 or 1.4 mmol) at 0° C. was added a solution of TBAF in THF (1.0 M, 2.0 mL or 2.8 mL, 2.0 or 2.8 equiv, (Fluka)) or a solution of tetrabutylammonium hydroxide (TBAOH) in MeOH (1.0 M, 3.0 mL, 3.0 equiv). The mixture was stirred 10 min at 0° C. and 10 min further at rt until no further gas evolution was observed. The aryl iodide (1.0 mmol, 1.0 equiv) was added to the mixture, followed by the palladium complex $[allylPdCl]_2$ (9 mg, 2.5 mol %). The mixture was stirred at rt for 10 min to 15 h and was then filtered through a short plug of silica gel or aluminum oxide (basic, activated, Brockmann I). The plug was washed with diethyl ether (50 mL) and the solvent was evaporated in vacuo. Purification of the residue by column chromatography affords the coupling product which was further purified by Kugelrohr distillation or crystallization.

Reaction of Ethyl 3-Iodobenzoate with Silane 84 to form Ethyl 3-[2-(5,6-Dihydro-4H-pyranyl)]benzoate A-4

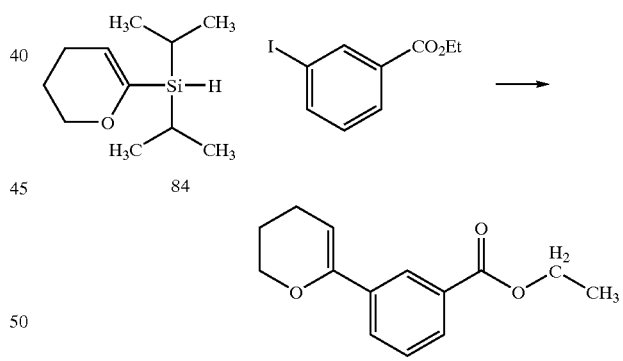

Following the General Procedure, 84 (2.38 mg, 1.2 mmol, 1.2 equiv), was dissolved in a solution of TBAF in THF (1.0 M, 2.0 mL, 2.0 mmol, 2.0 equiv) at 0° C. and was stirred for 10 min. The solution was allowed to warm to rt and was stirred for 10 min further Ethyl 3-iodobenzoate (0.166 mL, 1.0 mmol) and $[allylPdCl]_2$ (9 mg, 0.025 equiv) were added The suspension was stirred at rt for 10 min and then was filtered through a short plug of $SiO_2$. Purification of the residue by column chromatography ($SiO_2$, hexane/EtOAc, 20/1) and distillation afforded 200 mg (81%) of the previously described compound A-4.

Reaction of Ethyl 4-Iodobenzoate with Silane 85 from 4-(-Butoxyethenyl)benzoate B-4

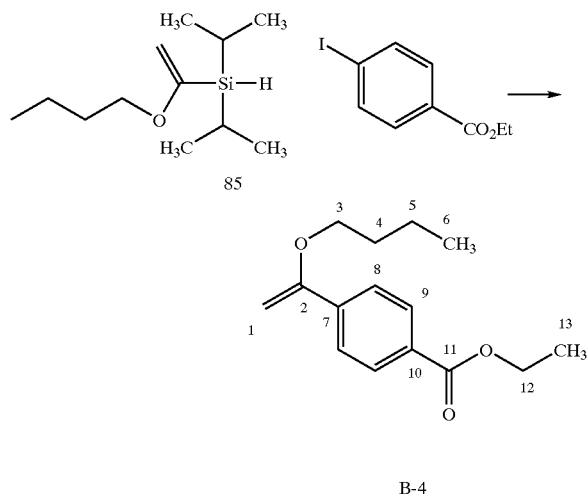

Following the General Procedure, 85 (300 mg, 1.4 mmol, 1.4 equiv), was dissolved in a solution of TBAF in THF (1.0 M, 2.8 mL, 2.8 mmol, 2.8 equiv) at 0° C. and was stirred for 10 min. The solution was allowed to warm to rt and was stirred for 10 min further. Ethyl 4-iodobenzoate (0.166 mL, 1.0 mmol) and [allylPdCl]$_2$ (9 mg, 0.025 equiv) were added. The suspension was stirred at rt for 10 min and then was filtered through a short plug of Al$_2$O$_3$. Purification of the residue by column chromatography (Al$_2$O$_3$, hexane/Et$_2$O, 30/1) and distillation afforded 221 mg (89%) of B-4 as a colorless oil.

Reaction of 4-Iodoacetophenone with Silane 86 to Form 1-[4-(4,5-Dihydro-furanyl)]ethanone C-4

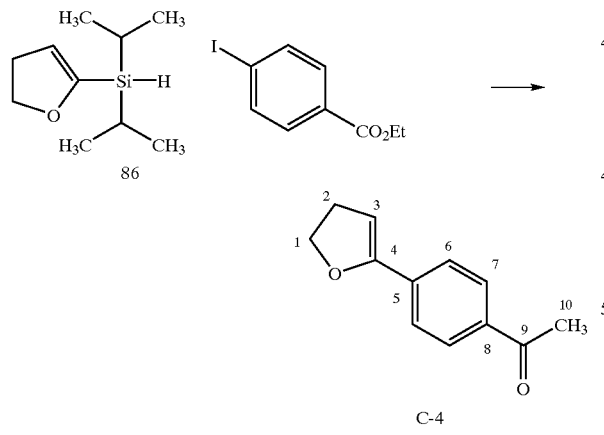

Following the General Procedure, 86 (220 mg, 1.2 mmol, 1.2 equiv), was dissolved in a solution of TBAOH in MeOH (1.0 M, 3 mL. 3.0 mmol, 3.0 equiv) at 0° C. and was stirred for 10 min. The solution was allowed to warm to rt and was stirred for 10 min further. 4-Iodoacetophenone (246 mg, 1.0 mmol, 1.0 equiv) and [allylPdCl]$_2$ (9 mg, 0.025 equiv) were added The suspension was stirred at rt for 10 min and then was filtered through a short plug of SiO$_2$. Purification of the residue by column chromatography (SiO$_2$, hexane/EtOAc, 8/1) and recrystallization from pentane afforded 133 mg (71%) of C-4 as a white solid.

EXAMPLE 6

Cross-coupling Reactions of Cycloalkenylsiloxanes Synthesized by Ring-closing Metathesis

General Experimental

All reactions were performed in oven-dried (140° C.) or flame-dried glassware under an inert atmosphere of dry Ar or N$_2$. The following reaction solvents were distilled from the indicated drying agents: diethyl ether (Na, benzophenone), THF (Na, benzophenone), CH$_2$Cl$_2$ (P$_2$O$_5$), benzene (Na), toluene (Na), methanol (Mg(OMe)$_2$), triethylamine (CaH$_2$). n-Butyllithium solution were titrated following the method of Gilman[1]. Brine refers to a saturated aqueous solution of NaCl. Grignard solutions were titrated using 2,2'-phenanthroline as an indicator[2]. Kugelrohr distillations were performed on a Büchi GKR-50 Kugelrohr; boiling points (bp) corresponding to uncorrected air-bath temperatures (ABT). All reaction temperatures correspond to internal temperatures measured by Teflon-coated thermocouples unless otherwise noted.

All commercial reagents were purified by distillation or recrystallization prior to use. A 1.0 M solution of tetrabutylammonium fluoride in THF was prepared from solid tetrabutylammonium fluoride trihydrate (TBAF.3H$_2$O, Fluka) and distilled THF in a volumetric flask and was stored in a Schlenk bottle. Palladium bis (dibenzylideneacetone) (Pd(dba)$_2$) was purchased from Jansen and used without purification. π-Allylpalladium chloride dimer [allylPdCl]$_2$ was purchased from ACROS and was recrystallized from benzene prior to use.

Literature Preparations

The following compounds were prepared by literature methods: 1-phenyl3-buten-1-ol,[3] 1-phenyl-2-propen-1-ol,[4] 1-phenyl-4-penten-1-ol[5] Schrock's catalyst[6] (2,6-diisopropylphenyl-imidoneophylidenemolybdenum(VI) bis (hexafluoro-t-butoxide).

Preparation of Dimethyl[(1-phenyl-3-butenyl)oxy] vinylsilane 73

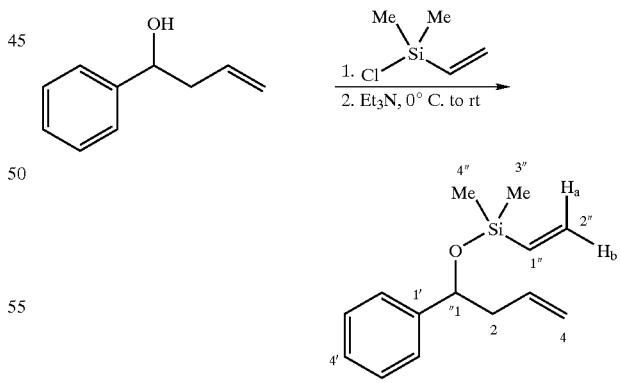

In a 50-mL flask was placed 1-phenyl-3-buten-1-ol (3.19 g, 21.5 mmol) and Et$_3$N (4.48 mL, 32.25 mmol, 1.5 equiv) in CH$_2$Cl$_2$ (30 mL) under N$_2$ atmosphere at 0° C. (ice bath temperature). To the mixture was added dropwise with chlorodimethylvinylsilane (3.86 mL, 28.0 mmol, 1.2 equiv).

The mixture was allowed to warm to room temperature and was stirred for 2 h. The mixture was then poured to ice water (30 mL) and was extracted with CH$_2$Cl$_2$ (2×30 mL). The combined organic layers were dried (Na$_2$SO$_4$), filtered and the solvent was removed by rotary evaporation. The residue was distilled under reduced pressure to afford 4.59 g (92%) of 73 as a colorless liquid.

General Procedure I. Molybdenum-catalyzed Ring-closing Metathesis

Into a flame-dried, 25-mL flask was placed freshly distilled benzene which was then moved into a dry box. Schrock's catalyst (0.05–0.08 equiv) and silyl ether (e g., 73) 1 equiv. were added sequentially to the flask. The yellow-brown solution was stirred at room temperature in the dry box. The mixture was monitored by $^1$H-NMR analysis. When the reaction was complete, the solvent was removed by rotary evaporation to give a brown residue, which was filtered through a short column of silica gel which was further eluted with hexane/EtOAc, 49/1. The filtrate was concentrated followed by Kugelrohr distillation to afford the product.

Ring-closing Metathesis of 73 Preparation of 2,2-Dimethyl-6-phenyl-1-oxa-2-silacyclohex-3-ene 74

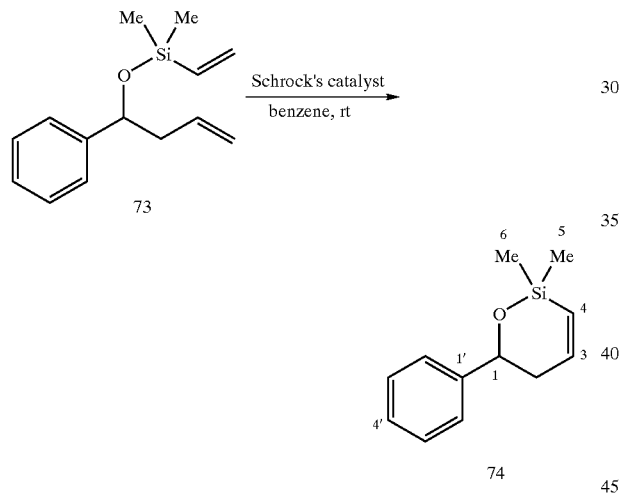

Following General Procedure I, benzene (10 mL), Schrock's catalyst (38 mg, 0.05 mmol, 0.05 equiv), and 73(232 mg, 1.0 mmol) were combined and the mixture was stirred at room temperature for 1 h in the dry box. After removal of the solvent by rotary evaporation, the residue was filtered through a short column of silica gel which was eluted with 100 mL of hexane/EtOAc, 49/1. The filtrate was concentrated followed by Kugelrohr distillation to afford 193 mg (95%) of 74 as a colorless liquid.

General Procedure II. Palladium-catalyzed Cross-coupling of 74 or 76 with Aryl or Alkenyl Halides Substrate 74 or 76 (1.1 equiv) was dissolved in a solution of TBAF (1.0 M in THF, 2.0 equiv) under an Ar atmosphere at ambient temperature. After 2 min, aryl or alkenyl halide (1.0 equiv) and the palladium catalyst (0.03–0.1 equiv) were then added sequentially. The reaction was monitored by TLC analysis. When the halide was consumed, 2 mL of EtOAc/hexane, 7/3 were added. The mixture was filtered through a shot column of silica gel, which was then eluted with EtOAc/hexane, 7/3 (150–200 mL). The filtrate was concentrated by rotary evaporation to give a crude product, which was purified by silica gel chromatography.

Coupling Reaction of 74 with 4-Iodoacetophenone. Preparation of 1-{4[(Z)-4-hydroxy-4-phenyl-1-butenyl]phenyl}ethanone (75a)

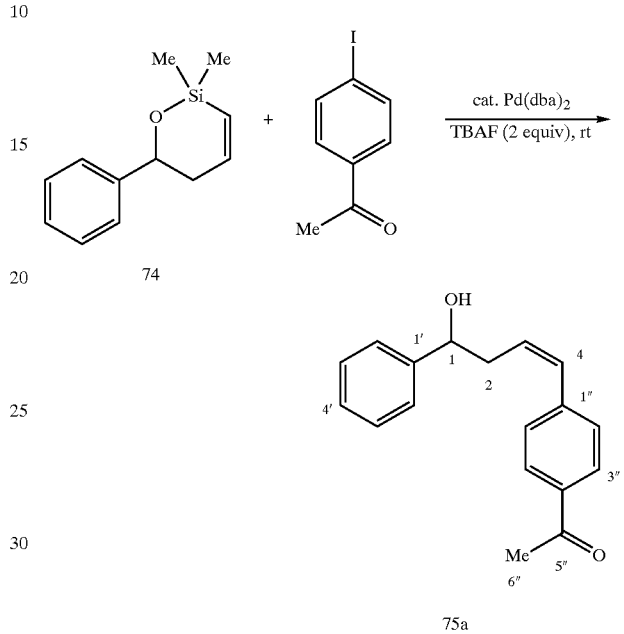

Following general Procedure II, 74 (225 mg, 1.1 mmol, 1.1 equiv), a solution of TBAF in THF (1.0 M, 2.0 mL, 2.0 mmol, 2.0 equiv), 4-iodoacetophenone (246 mg, 1.0 mmol) and Pd(dba)$_2$ (28.7 mg, 0.05 mmol, 0.05 equiv) were combined The mixture was stirred at room temperature for 10 min and then 2 mL of EtOAc/hexane, 7/3 were added. The mixture was filtered through a short column of silica gel which was eluted with 150 mL of EtOAc/hexane, 7/3. The filtrate was concentrated to give a crude product which was purified by chromatography (silica gel, hexane/EtOAc, 8/2 to 7/3) to afford 240 g (90%) in of 75a as a pale yellow (non-distillable) oil.

Coupling Reaction of 74 with 4-Iodoanisole. Preparation of (Z)-Phenyl-4-(4-methoxyphenyl)-3-buten-1-ol 75b

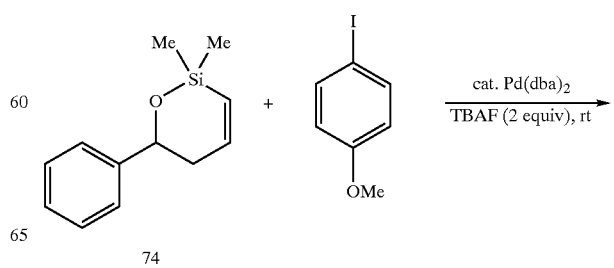

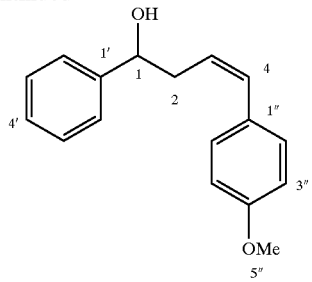

75b

Following General Procedure II, 74 (225 mg, 1.1 mmol, 1.1 equiv), a solution of TBAF in THF (1.0 M, 2.0 mL, 2.0 mmol, 2.0 equiv), 4-iodoanisole (234 mg, 1.0 mmoll) and Pd(dba)$_2$ (17.2 mg, 0.03 mmol, 0.03 equiv) were combined. The mixture was stirred at room temperature for 30 min and then 2 mL of EtOAc/hexane, 7/3 were added. The mixture was filtered though a short column of silica gel which was eluted with 150 mL of EtOAc/hexane, 7/3. The filtrate was concentrated to give a crude product which was purified by chromatography (silica gel, hexane/EtOAc. 9/1 to 4/1) to afford 234 mg (92%) of 75b as a pale yellow (non-distillable) oil.

Coupling Reaction of 74 with Ethyl 3-Iodobenzoate. Preparation of Ethyl 3-[(Z)-4-hydroxy-4-phenyl-1-butenyl]benzoate 75c

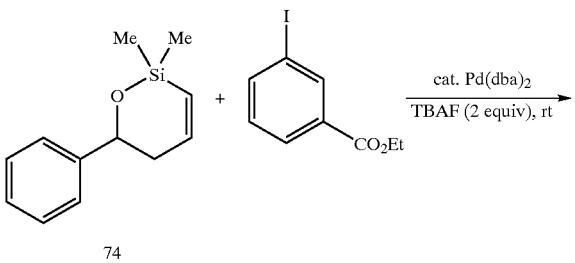

75c

Following General Procedure II, 74 (225 mg, 1.1 mmol, 1.1 equiv), a solution of TBAF in THF (1.0 M, 2.0 mL, 2.0 mmol, 2.0 equiv), ethyl 3-iodobenzoate (276 mg, 1.0 mmol) and Pd(ba)$_2$ (17.2 mg, 0.03 mmol, 0.03 equiv) were combined. The mixture was stirred at room temperature for 30 min and then 2 mL of EtOAc/hexane, 7/3 were added. The mixture was filtered through a short column of silica gel which was eluted with 150 in of EtOAc/hexane, 7/3. The filtrate was concentrated to give a crude product which was purified by chromatography (silica gel, hexane/EtOAc, 9/1 to 4/1) to afford 276 mg (93%) of 75c as a pale yellow (non-distillable) oil.

Coupling Reaction of 74 with 2-Iodotoluene. Preparation of (Z)-1-Phenyl-4-(2-methylphenyl)-3-buten-1-ol 75d

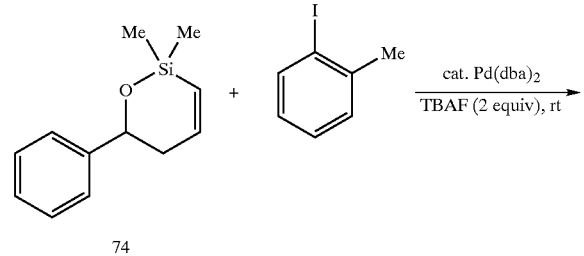

75d

Following General Procedure II, 74 (225 mg, 1.1 mmol, 1.1 equiv), a solution of TBAF in THF (1.0 M, 2.0 mL, 2.0 mmol, 2.0 equiv), 2-iodotoluene (218 mg, 1.0 mmol) and Pd(dba)$_2$ (17.2 ml, 0.03 mmol, 0.03 equiv) were combined. The mixture was stirred at room temperature for 30 min and then 2 mL of EtOAc/hexane, 7/3 were added. The mixture was filtered through a short column of silica gel which was eluted with 150 mL of EtOAc/hexane, 7/3. The filtrate was concentrated to give a crude product which was purified by chromatography (silica gel, hexane/EtOAc, 9/1 to 4/1) to afford 212 mg (89%) of 75d as a pale yellow (non-distillable) oil.

Coupling Reaction of 74 with (E)-2-Bromostyrene. Preparation of (3Z,5E)-1,6-Diphenyl-3,5-hexadien-1-ol (6).

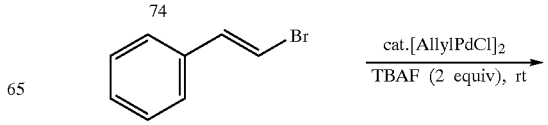

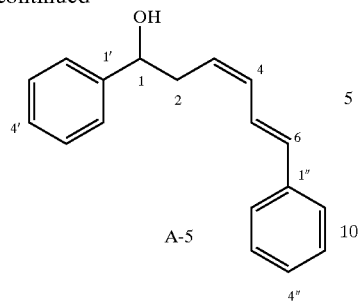

A-5

Preparation of 3-Methyl-1-phenyl-1-buten-1-ol

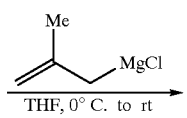
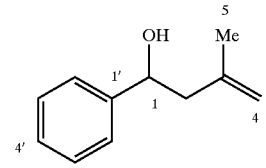

Following General Procedure II, 74 (225 mg, 1.1 mmol, 1.1 equiv), a solution of TBAF in THF (1.0 M, 2.0 mL, 2.0 mmol, 2.0 equiv), (E)-2-bromostyrene (183 mg, 1.0 mmol) and [allylPdCl]$_2$ (9.2 mg, 0.025 mmol, 0.025 equiv) were combined. The mixture was stirred at room temperature for 5 h and then 2 mL of EtOAc/hexane, 7/3 were added. The mixture was filtered through a short column of silica gel which was eluted with 150 mL of EtOAc/hexane, 7/3. The filtrate was concentrated to give a crude product which was purified by chromatography (silica gel, hexane/EtOAc, 19/1 to 17/3) to afford 194 mg (78%) of A-5 as a pale yellow (non-distillable) oil.

To a solution of benzaldehyde (3.05 mL, 30 mmol) in THF (30 mL) was added 2-methylallylmagnesium chloride (0.8 M in THF, 45 mL, 36 mmol, 1.2 equiv) under N$_2$ at 0° C. (internal). The mixture was warmed to room temperature and was stirred for 1.5 h. The mixture was then poured into saturated aqueous NH$_4$Cl solution (30 mL) and was extracted with EtOAc (2×30 mL). The combined organic layers were washed with brine (30 mL), then were dried (Na$_2$SO$_4$) and filtered. The solvent was removed by rotary evaporation and the residue was purified by Kugelrohr distillation to afford 4.33 g (89%) of 3-methyl-1-phenyl-1buten-1-ol as a colorless oil.

Preparation of Dimethyl[(1-phenyl-2-propenyl)oxy]vinylsilane,

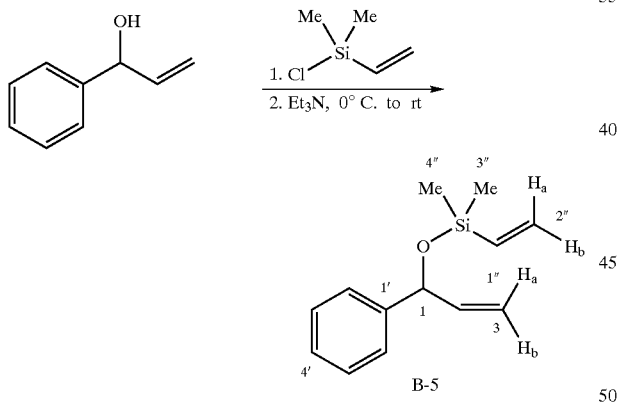

B-5

Preparation of Dimethyl[(1-phenyl-3-methyl-3-butenyl)oxy]vinylsilane

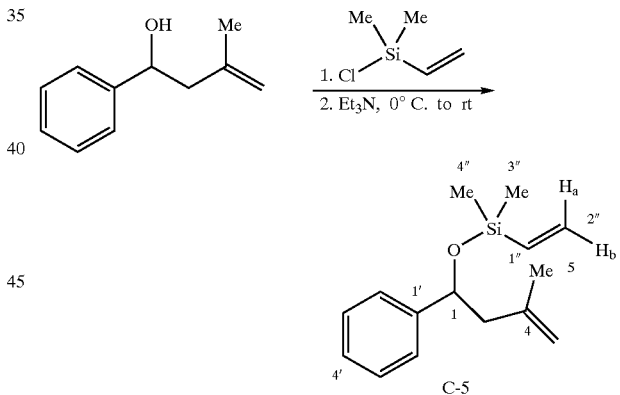

C-5

In a 25-mL flask was placed 1-phenyl-2-propen-1-ol (1.34 g, 10.0 mmol) and Et$_3$N (2.08 mL, 15.0 mmol, 1.5 equiv) in CH$_2$Cl$_2$ (10 mL) under N$_{12}$ atmosphere at 0° C. (internal). To the solution was added dropwise chlorodimethylvinylsilane (1.66 mL, 12.0 mmol, 1.2 equiv). The solution was allowed to warm to room temperature and was stirred for 1 h. The mixture was then poured to ice water (30 mL) and was extracted with CH$_2$Cl$_2$ (2×30 mL). The combined organic layers were dried (Na$_2$SO$_4$), filtered and the solvent was removed by rotary evaporation. The residue was purified by chromatography (silica gel, hexane/EtOAc, 49/1) followed Kugelrohr distillation under reduced pressure to afford 1.96 (90%) of B-5 as a colorless liquid.

In a 25-mL flask was placed 3-methyl-1-phenyl-3-buten-1-ol (2.43 g, 15.0 mmol) and Et$_3$N (3.13 mL, 22.5 mmol, 1.5 equiv) in CH$_2$C$_2$ (15 mL) under a N$_2$ atmosphere at 0° C. (internal). To the solution was added dropwise chlorodimethylvinylsilane (2.48 mL, 18.0 mmol, 1.2 equiv). The mixture was allowed to warm to room temperature and was stirred for 1 h. The mixture was then poured to ice water (30 mL) and the aqueous phase was extracted with CH$_2$Cl$_2$ (2×30 mL). The combined organic layers were dried (Na$_2$SO$_4$), filtered and the solvent was removed by rotary evaporation. The residue was purified by chromatography (silica gel, hexane/EtOAc, 49/1) followed Kugelrohr distillation under reduced pressure to afford 3.32 g (90%) of C-5 as a colorless liquid.

Preparation of (1-Phenyl-3-buten-1-yloxy)-(2-octenyl)dimethylsilane

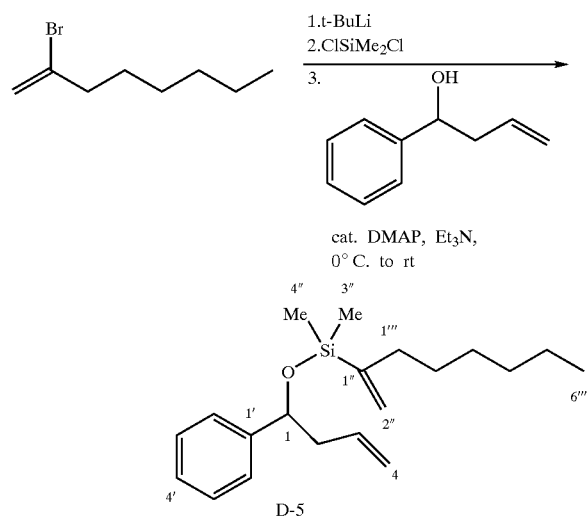

D-5

To a solution of 2-bromo-1-octene (1.25 g, 6.6 mmol, 1.1 equiv) in Et$_2$O (7 mL) was added dropwise t-BuLi (1.5 M, 8.8 mL, 13.2 mmol, 2.2 equiv) under a N$_2$ atmosphere at −78° C. (internal). The pale-yellow, cloudy mixture was stirred for 1 h at −78° C. (internal). The mixture was then added to a solution of dichlorodimethylsilane (1.82 mL, 15.0 mmol, 2.5 equiv) in Et$_2$O (10 mL) by cannula at −78° C. (internal). The mixture was allowed to warm to room temperature and was stirred for 2 h whereupon a white solid precipitated. After removal of solvent and excess dichlorodimethylsilane under reduced pressure, hexane (50 mL) was added and the solids were removed by Schlenk filtration. After removal of the solvent, the residue was dissolved in CH$_2$Cl$_2$ (5 mL). The solution was then added to a solution of 1-phenyl-3-buten-1-ol (888 mg, 6.0 mmol, 1.0 equiv), 4-dimethylaminopyridine (110 mg, 0.9 mmol, 0.15 equiv), and Et$_3$N (1.25 mL, 9.0 mmol, 1.5 equiv) in C$_2$Cl$_2$ (10 mL) under N$_2$ atmosphere at 0° C. (internal). The mixture was allowed to warm to room temperate and was stirred for 2 h. The mixture was then poured to ice water (20 mL) and the aqueous phase was extracted with CH$_2$Cl$_2$ (2×20 mL). The combined organic layers were dried (Na$_2$SO$_4$), filtered and the solvent was removed by rotary evaporation. The residue was purified by chromatography (silica gel, hexane) followed Kugelrohr distillation under reduced pressure to afford 1.25 g (66%) of D-5 as a colorless liquid.

Preparation of Dimethyl-(2octenyl)-[(1-phenyl-3-methyl-3-butenyl)oxy]silane

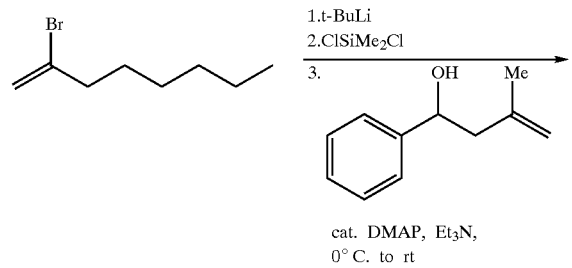

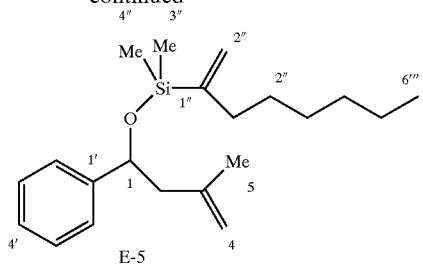

E-5

To a solution of 2-bromo-octene (2.85 g, 15.0 mmol 1.2 equiv) in Et$_2$O (15 mL) was added dropwise with t-BuLi (1.5 M, 20.0 mL, 30.0 mmol, 2.4 equiv) under N$_2$ atmosphere at −78° C. (internal). The pale-yellow, cloudy mixture was stirred for 1 h at −78° C. (internal). The mixture was then added to a solution of dichlorodimethylsilane (3.8 mL, 31.25 mmol, 2.5 equiv) in Et$_2$O (15 mL) via cannula at −78° C. (internal). The mixture was allowed to warm to room temperature and was stirred for 2 h whereupon a white solid precipitated. After removal of solvent and excess dichlorodimethylsilane under reduced pressure, hexane (50 mL) was added and the solids were removed by Schlenk filtration. After removal of the solvent, the residue was dissolved in CH$_2$Cl$_2$ (5 mL). The solution was then added to a solution mixture of 1-phenyl-3-methyl-3-buten-1-ol (2.03 g, 12.5 mmol, 1.0 equiv), 4dimethylaminopyridine (229 mg, 1.88 mmol, 0.15 equiv), and Et$_3$N (2.6 mL, 18.8 mmol, 1.5 equiv) in CH$_2$Cl$_2$ (10 mL) under N$_2$ atmosphere at 0° C. (internal). The mixture was allowed to warm to room temperature and was stirred for 2 h. The mixture was then poured to ice water (20 mL) and aqueous phase was extracted with CH$_2$Cl$_2$ (2×20 mL). The combined organic layers were dried (Na$_2$SO$_4$), filtered and the solvent was removed by rotary evaporation. The residue was purified by chromatography (silica gel, hexane) followed Kugelrohr distillation under reduced pressure to afford 2.85 g (69%) of E-5 as a colorless liquid.

Preparation of Dimethyl[(1-phenyl-4-pentenyl)oxy]vinylsilane

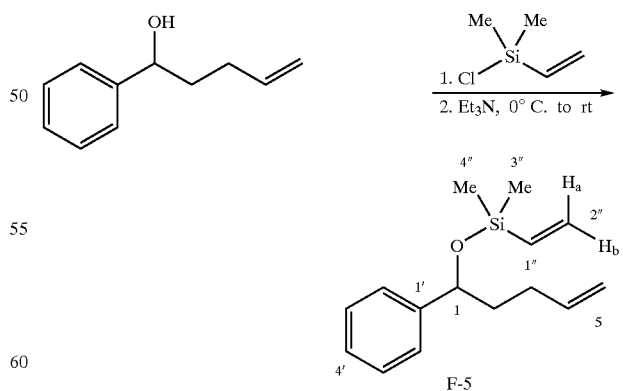

F-5

In a 50-mL flask was placed 1-phenyl-4-penten-1-ol (3.24 g, 20.0 mmol) and Et3N (4.2 mL, 30.0 mmol, 1.5 equiv) in CH$_2$Cl$_2$ (20 mL) under a N$_2$ atmosphere at 0° C. (internal). To the mixture was added dropwise chlorodimethylvinylsilane (3.3 mL, 24.0 mmol, 1.2 equiv). The mixture was allowed to warm to room temperature and was stirred for 0.5 h. The mixture was then poured to ice water (30 mL) and the aqueous phase was extracted with CH$_2$Cl$_2$ (2×30 mL). The combined organic layers were dried (Na$_2$SO$_4$), filtered and the solvent was removed by rotary evaporation. The residue was purified by chromatography (silica gel, hexane/EtOAc, 49/1) followed Kugelrohr distillation under reduced pressure to afford 4.48 g (91%) of F-5 as a colorless liquid.

Ring-closing Metathesis of G-5 Preparation of 2,2-Dimethyl-5-phenyl-1-oxa-2-silacyclopent-3-ene

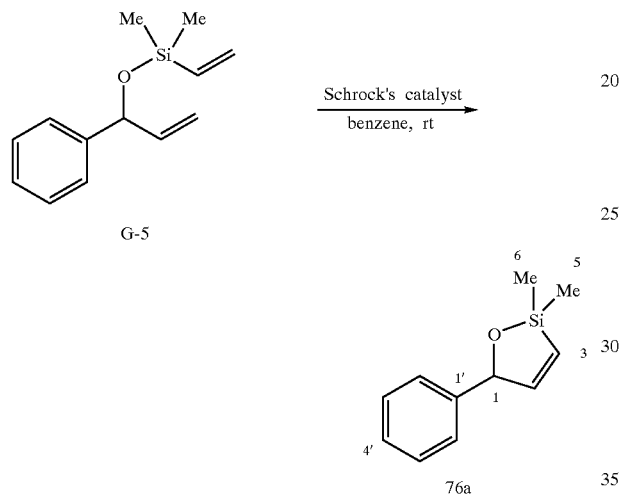

Following General Procedure I, benzene (10 mL), Schrock's catalyst (53.6 mg, 0.07 mmol, 0.07 equiv), and G-5 (218 mg, 1.0 mmol, 1.0 equiv) were combined and the mixture was stirred at room temperature for 3 h in the dry box. After removal of the solvent under reduced pressure, the residue was filtered through a short column of Celite which was then eluted with 100 mL of hexane/EtOAc, 49/1. The filtrate was concentrated followed by Kugelrohr distillation to afford 168 mg (89%) of 76a as a colorless liquid.

Ring-closing Metathesis of H-5. Preparation of 2,2,4-Trimethylphenyl-6-phenyl-1-oxa-2-silacyclohex-3-ene (76d).

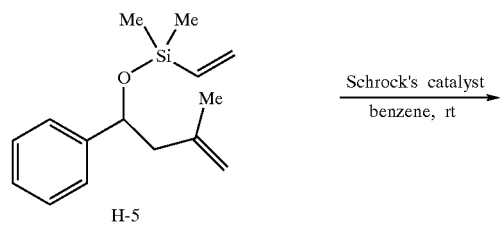

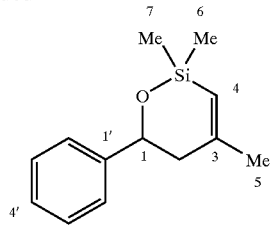

Following General Procedure I, benzene (10 mL), Schrock's catalyst (53.6 mg, 0.07 mmol, 0.07 equiv), and H-5 (246 mg, 1.0 mmol, 1.0 equiv) were combined and the mixture was stirred at room temperature for 12 h in the dry box. $^1$H NMR analysis showed that the reaction was not complete (conversion: 90%). To the mixture was added another portion of catalyst (7.6 mg, 0.01 mmol, 0.01 equiv) and the mixture was stirred for another 3 h. After removal of the solvent under reduced pressure, the residue was filtered through a short column of silica gel which was eluted with 100 mL of hexane/EtOAc, 49/1. The filtrate was concentrated and the residue was purified by Kugelrohr distillation to afford 199 mg (91%) of 76b as a colorless liquid.

Ring-closing Metathesis of I-5 Preparation of 2,2-Dimethyl-3-hexyl-6-phenyl-1-oxa-2-silacyclohex-3-ene 76c

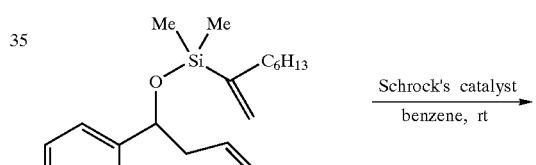

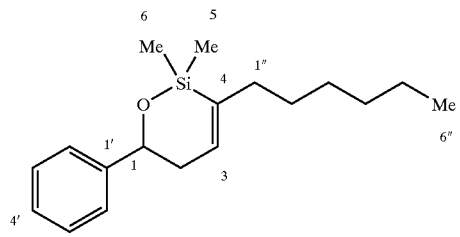

Following General Procedure I, benzene (10 mL), Schrock's catalyst (53.6 mg, 0.07 mmol, 0.07 equiv), and I-5 (316 mg, 1.0 mmol, 1.0 equiv) were combined and the mixture was stirred at room temperature for 12 h in the dry box. After removal of the solvent under reduced pressure, the residue was filtered through a short column of silica gel which was eluted with 100 mL of hexane/EtOAc, 49/1. The filtrate was concentrated followed by Kugelrohr distillation to afford 259 mg (90%) of 76c as a colorless liquid.

Ring-closing Metathesis of J-5 Preparation of 2,2-Dimethyl-7-phenyl-1-oxa-2-silacyclohex-3-ene 76d

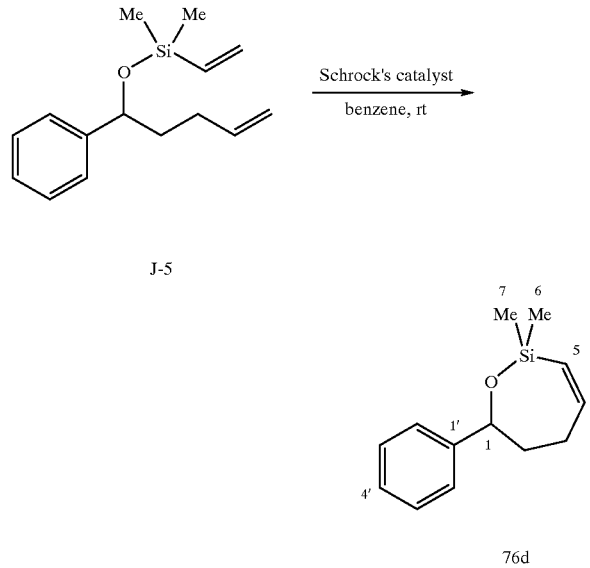

Following General Procedure II, benzene (10 mL), Schrock's catalyst (38.3 mg, 0.05 mmol, 0.05 equiv), J-5 (246 mg, 1.0 mmol, 1.0 equiv) were combined and the mixture was stirred at room temperature for 6 h in the dry box. $^1$H NMR analysis showed that the reaction was not complete (conversion: 80%). To the mixture was added another portion of catalyst (15.3 mg, 0.02 mmol, 0.02 equiv) and the mixture was stirred for another 6 h (conversion 91%). After removal of the solvent under reduced pressure, the residue was filtered through a short column of silica gel which was eluted with 100 mL of hexane/EtOAc, 49/1. The filtrate was concentrated and the residue was purified by chromatography (silica gel, hexane/CH$_2$Cl$_2$, 17/3) followed by Kugelrohr distillation to afford the product 176 mg (81%) of 76d as a colorless oil.

Coupling Reaction of 76a with Ethyl 4-Iodobenzoate. Preparation of Ethyl 4-[(Z)-3-hydroxy-3-phenyl-1-propenyl]benzoate

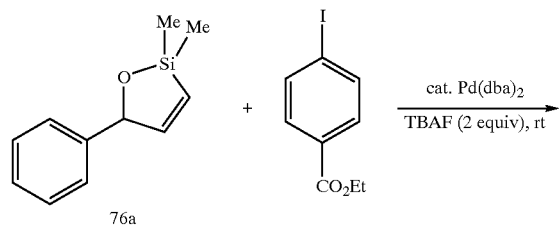

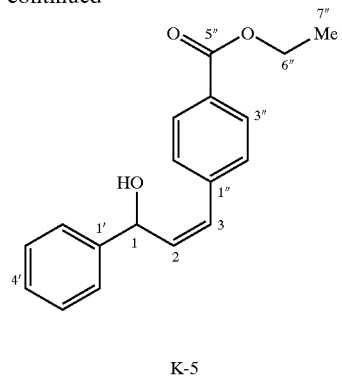

K-5

Following General Procedure II, 76a (209 mg, 1.1 mmol, 1.1 equiv), a solution of TBAF in THF (1.0 M, 2.0 mL, 2.0 mmol, 2.0 equiv), ethyl 4-iodobenzoate (276 mg, 1.0 mmol) and Pd(dba)$_2$ (17.2 mg, 0.03 mmol, 0.03 equiv) were combined. The mixture was stirred at room temperature for 30 min and then 2 mL of EtOAc/hexane, 7/3 were added. The mixture was filtered through a short column of silica gel which was eluted with 150 mL of EtOAc/hexane, 7/3. The filtrate was concentrated to give a crude product which was purified by chromatography (silica gel, hexane/EtOAc, 19/1 to 4/1) to afford 240 mg (85%) of K-5 as a pale yellow (non-distillable) oil.

Coupling Reaction of 76b with 2-Iodotoluene. Preparation of (Z)-1-Phenyl-3-methyl-4-(2-methylphenyl)-3-buten-1-ol

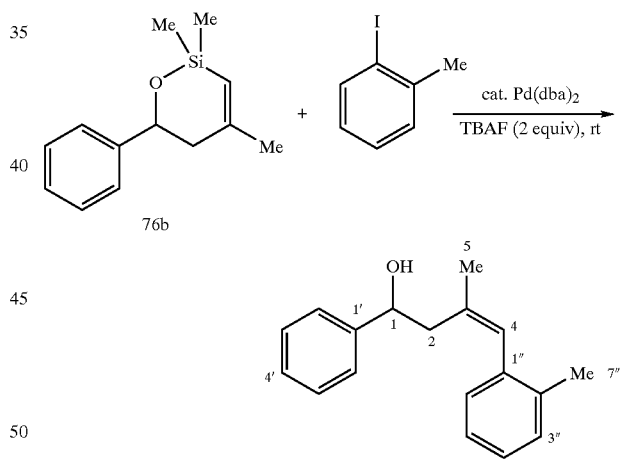

L-5

Following General Procedure II, 76b (240 mg, 1.1 mmol, 1.1 equiv), a solution of TBAF in THF (1.0 M, 2.0 mL, 2.0 mmol, 2.0 equiv), 2-iodotoluene (218 mg, 1.0 mmol) and Pd(dba)$_2$ (17.2 mg, 0.03 mmol, 0.03 equiv) were combined. The mixture was stirred at room temperature for 45 min and then 2 mL of EtOAc/hexane, 7/3 were added. The mixture was filtered through a short column of silica gel which was eluted with 150 mL of EtOAc/hexane, 7/3. The filtrate was concentrated to give a crude product which was purified by chromatography (silica gel, hexane/EtOAc, 19/1 to 9/1) to afford (209 mg (83%) of L-5 as a pale yellow (non-distillable) oil.

Coupling Reaction of 78c with Ethyl 3-Iodobenzoate. Preparation of Ethyl 3-[(Z)-1-hexyl-4-hydroxy-4-phenyl-1-butenyl]benzoate

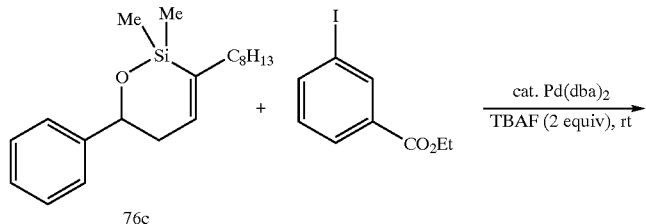

76c

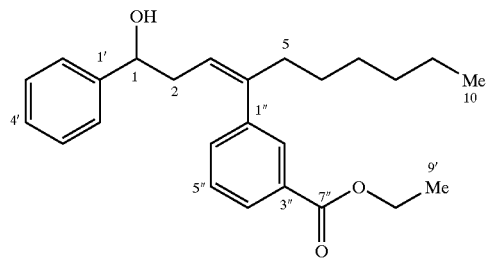

M-5

Siloxane 76c (317 mg, 1.1 mmol, 1.1 equiv) was dissolved in a solution of TBAF (1.0 M in THF, 2.0 mL, 2.0 mmol, 1.0 equiv) under an Ar atmosphere at ambient temperature. After 2 min, ethyl 3-iodobenzoate (69 mg, 0.25 mmol, 0.25 equiv) and Pd(dba)$_2$ (14.3 mg, 0.025 mmol, 0.025 equiv) were then added sequentially. The mixture was stirred at room temperature for 3 h. Additional portions of ethyl 3-iodobenzoate (69 mg, 0.25 mmol, 0.25 equiv) and Pd(dba)$_2$ (14.3 mg, 0.025 mmol, 0.025 equiv) were added 3 times at 3 h intervals. The mixture was stirred for 24 h at room temperature and then 2 mL of EtOAc/hexane, 7/3 were added. The mixture was filtered through a short column of silica gel which was eluted with 150 mL of EtOAc/hexane, 7/3. The filtrate was concentrated to give a crude product which was purified by chromatography (silica gel, hexane/EtOAc, 19/1 to 4/1) to afford 307 mg (81%) of M-5 as a pale yellow (non-distillable) oil.

Coupling Reaction of 76d with 4-Iodoanisole. Preparation of (Z)-1-Phenyl-5-(4-methoxyphenyl)-4-penten-1-ol

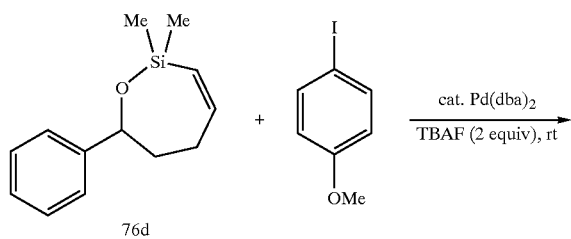

76d

-continued

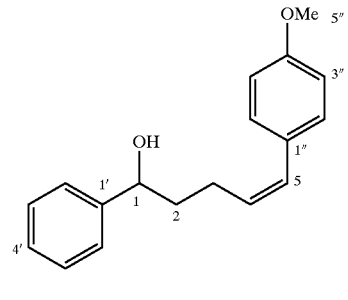

N-5

Following General Procedure II, 76d (240 mg, 1.1 mmol, 1.1 equiv), a solution of TBAF in THF (1.0 M, 2.0 mL, 2.0 mmol, 2.0 equiv), 4-iodoanisole (234 mg, 1.0 mmol, 1.0 equiv) and Pd(dba)$_2$ (17.2 mg, 0.03 mmol, 0.03 equiv) were combined. The mixture was stirred at room temperature for 30 min and then 2 mL of EtOAc/hexane, 7/3 were added. The mixture was filtered through a short column of silica gel which was eluted with 150 mL of EtOAc/hexane, 7/3. The filtrate was concentrated to give a crude product which was purified by chromatography (silica gel, hexane/EtOAc, 19/1 to 17/3) to afford 228 mg (85%) of N-5 as a pale yellow (non-distillable) oil.

References for Example 6

(1) Gilman, H.; Cartledge, F. K; Sin, S.-Y. *J. Organomet. Chem.* 1963, 1, 8.

(2) *Chemistry of Metal-Carbon Bonds*, Vol. 1, Patai and Hartley Ed. Chapter 156, p 639.

(3) Hart D. J.; Kanai, K.-I.; *J. Org. Chem.* 1982, 47, 1555.

(4) Gazzard, L. J.; Motherwell, W. B.; Sandhan, D. A. *J. Chem. Soc. Perkin Trans* 1 1999, 979.

(5) Rawel, V. H.; Singh, S. P.; Dufour, C.; Michoud, C. *J. Org. Chem.* 1993, 58, 7718.

(6) The molybdenum complex 2 is commercially available (Stem) and can be prepared according to the reported procedure with consistent purity and reactivity, see: (I) Fox, H. H.; Yap, K. B.; Robbins, J.; Cai, S.; Schrock, R. R. *Inorg. Chem.* 1992, 31, 2287 (b) Schrock, R. R.; Murdzek, J. S.; Bazan, G. C., Robbins, J.; DiMare, J.; M.; O'Regan, M. *J. Am. Chem. Soc.* 1990. 112, 3875. (c) Oskam, J. H.; Fox. H. H., Yap, K. B.; McConville, D. H.; O'Dell, R; Liechtenstein. B. J.; Schrock, R. R. *J. Organomet. Chem.* 1993, 459, 185 (d) Fox, H. H., Lee J.-K.; Park, L. Y.; Schrock, R. R. *Organometallics* 1993, 12, 759.

(7) Ishihara, K.; Mouri, M; Gao, Q; Maruyama, T. Furuta, K.; Yamamoto, H. *J. Am. Chem. Soc.* 1993, 115, 11490.

EXAMPLE 7

Preparation of Diisopropyl-(3-pentynyloxy)silane

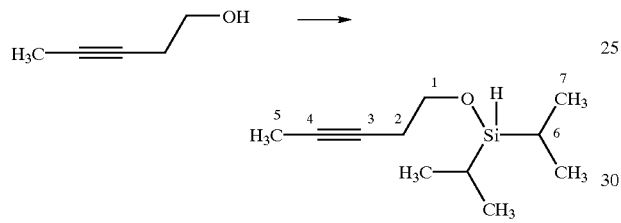

A-7

To a cold (0° C.) solution of 3-pentynol (5.880g, 70.0 mmol, 1.0 equiv), 4-dimethylaminopyridine (DMAP) (840 mg, 7.00 mmol, 0.10 equiv), and triethylamine (TEA) (9.80 ml, 71.0 mmol, 1.01 equiv) in 100 mL of dry hexane was added dropwise chlorodiisopropylsilane (11.0 g, 71.0 mmol, 1.01 equiv) over 20 minutes. The resulting white suspension was allowed to warm to room temperature and was stirred overnight. The reaction mixture was filtered through a short silica pad (10 g) and the solvent was then evaporated in vacuo to give a colorless liquid. Fractional distillation of this liquid afforded 11.2 g (81%) of A-7 as a colorless liquid. An analytical sample (0.48 g) was obtained by redistillation of a 0.50 g sample by Kugelrohr distillation.

Preparation of (E)-3-Ethylidene2,2-diisopropyl-1-oxa-2-silacyclopentane (78)

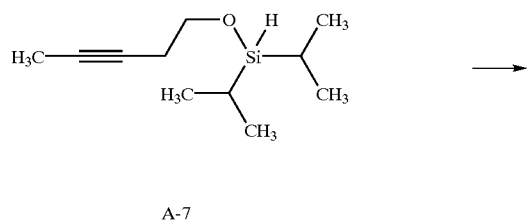

A-7

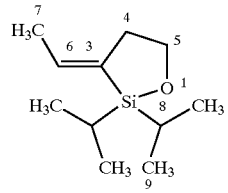

78

To a solution of silane A-7 (10.2 g, 51.5 mmol) in 200 mL of dry dichloromethane at room temperature was added $H_2PtCl_2 \cdot 6H_2O$ (0.90 mL of 0.2 M solution in isopropanol 0.18 mmol, 0.35% equiv). A vigorous exotherm was noted and reaction mixture was cooled in a tap water bath, and stirring was continued for 70 min. The solvent was then evaporated in vacuo give 10.7 g of an amber liquid. Fractional distillation of the liquid afforded 8.50 g of 78 (83%) as a colorless liquid.

General Procedure for Coupling of Oxasilacyclopentanes

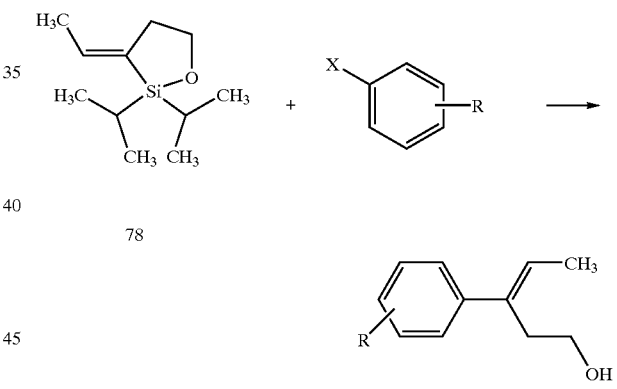

In a two-necked flask fitted with a rubber septum and gas inlet tube, the oxasilacyclopentane 78 (1.1 equiv) was dissolved in a solution of tetrabutylammonium fluoride (TBAF) (2.0 equiv), at ambient temperature under nitrogen. The electrophile (1.0 equiv) was added portionwise or in one portion as specified below. The palladium catalyst (5 mol % of Pd) was added in one portion to the mixture following the first portion of electrophile and the mixture was stirred at designated temperature for a designated period of time. The reaction mixture was purified with a specified amount of silica gel as indicated below by column chromatography. The products were further purified by Kugelrohr distillation and or sublimation.

Reaction of Iodobenzene with Oxasilacyclopentane 78. (E)-3-Phenyl-3penten-1-ol 79a

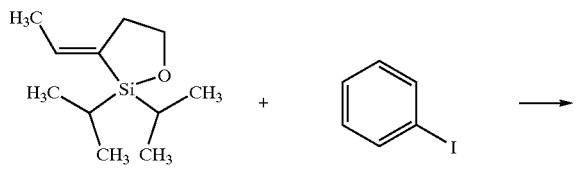

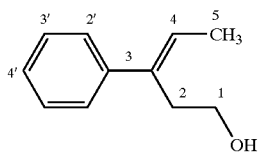

Following the General Procedure, 78 (432 mg, 2.18 mmol, 1.10 equiv), was dissolved in a solution of TBAF in THF (4.0 mL, 4.0 mmol, 2.0 equiv) and the mixture was stirred for 10 min at rt. Iodobenzene (405 mg, 1.98 mmol, 1.0 equiv) was added in three portions over 20-min intervals and Pd(dba)$_2$ (56 mg, 0.098 mmol, 0.050 equiv) was added following the first portion of iodide. The mixture was stirred at rt for a total of 400 min and then was extracted with 50 ml of 1/1 ether-pentane three times. Removal of tie solvents in vacuo afforded the crude product as a yellow oil. Purification of the oil by column chromatography (SiO$_2$, 63 g, pentane/ether, 9/1) and Kugelrohr distillation afforded 284 mg (88%) of 79a as a colorless oil. Biphenyl (4.0 mg, ca 2%) was also isolated.

Reaction of 1-Iodonaphthalene with Oxasilacyclopentane 78 (E)-3-(1-Naphthyl)-3-penten-1-ol 79k

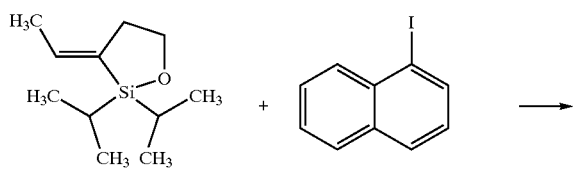

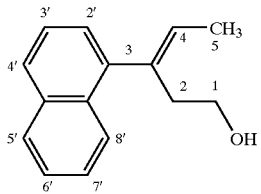

Following the General Procedure, 78 (243 mg, 1.23 mmol, 1.1 equiv), was dissolved in a solution of TBAF in THF (2.2 mL, 2.2 mmol, 2.0 equiv) and the mixture was stirred for 10 min at rt. 1-Iodonaphthalene (283 mg, 1.12 mmol, 1.0 equiv) was added in three portions over 55-min intervals and Pd(dba)$_2$ (32 mg, 0.056 mmol, 0.050 equiv) was added following the first portion of iodide. The mixture was stirred at 35° C. for a total of 500 min. The crude mixture was then loaded onto 2 g of silica gel and was purified by column chromatography (SiO$_2$, 32 g, pentane/ether, 9/1). Removal of the solvent and subsequent sublimation (60° C./0.1 mm Hg) of the resulting product afforded 180 mg (76%) of 79k as a white solid.

Reaction of 3-Iodopyridine with Oxasilacyclopentane 78 (E)-3-(3-Pyridyl-3-penten-1-ol 79m

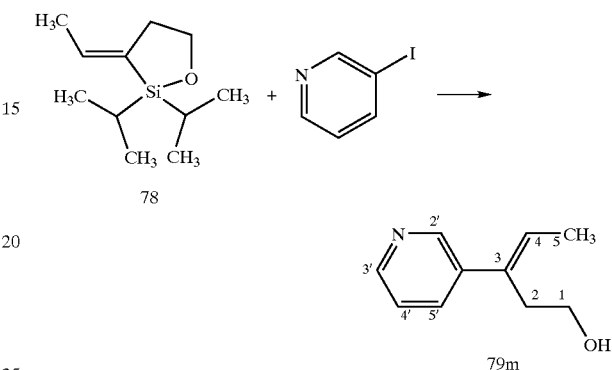

Following the General Procedure, 78 (440 mg, 2.2 mmol, 1.1 equiv), was dissolved in a solution of TBAF in THF (4.0 mL. 4.0 mmol, 2.0 equiv) and the mixture was stirred for 10 min at rt. 3-Iodopyridine (412 mg, 2.0 mmol, 1.0 equiv) was added in one portion and Pd(dba)$_2$ (57 mg, 0.10 mmol, 0.050 equiv) was then added. The mixture was stirred at 45° C. for a total of 45 h. The crude mixture was then loaded onto 4 g of silica gel and was purified by column chromatography (SiO$_2$, 75 g, pentane/ether, 1/1). Removal of the solvent and Kugelrohr distillation of resulting product afforded 240 mg (74%) of 79m as a colorless oil.

One-pot Arylation of 3-Pentyn-1-ol with Iodobenzene. (E)-3-Phenyl-3-penten-1-ol

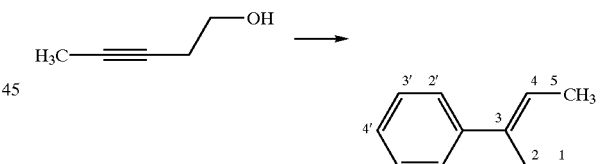

In a two-necked flask was placed 3-pentyn-1-ol (160 mg, 1.90 mmol, 1.3 equiv) and tetramethyldisiloxane (0.26 mL 1.50 mmol, 1.0 equiv) was added dropwise at rt. The mixture was stirred for 1 h, whereupon dry THF (3.0 mL) was added followed by platinum(0)-1,3-divinyl-1,1,3,3-tetramethyldisiloxane complex (50 uL, in xylenes). The mixture was stirred at rt for 1 h (GC/MS monitoring indicated hydrosilylation was completed). To this mixture was added dropwise a solution of TBAF in THF (3.3 mL, 3.3 mmol, 2.2 equiv). Iodobenzene (306 mg, 1.50 mmol, 1.0 equiv) and Pd(dba)$_2$ (84 mg, 0.15 mmol, 0.10 equiv) were each added in one portion, successively to the mixture. The mixture was stirred at rt for 40 min. Reaction mixture was loaded onto 4 g of silica gel and was purified by column chromatography (SiO$_2$, 40 g, pentane/ether, 9/1) and Kugelrohr distillation afforded 206 mg (85%) of 213 as a colorless oil Biphenyl was neither detected nor isolated.

One-pot Arylation of 3-Octyn-1-ol with 4-Iodobenzene with 10% Pd(dba)$_2$. (E-3-Phenyl-3-octen-1-ol 214

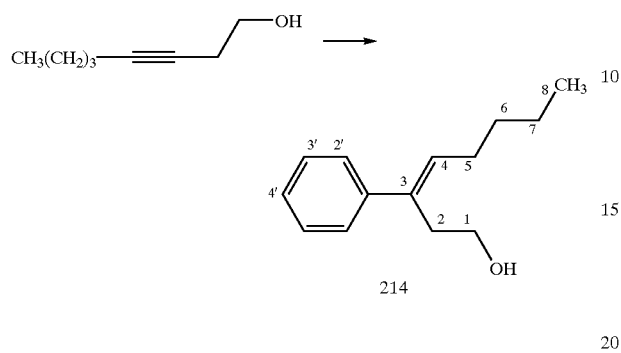

In a two-necked flask was placed 3-octyn-1-ol (246 m, 1.95 mmol 1.3 equiv) and tetramethyldisilazane (0.27 mL, 1.56 mmol, 1.04 equiv) was added dropwise at rt. The mixture was stirred for 1.5 h, then the reaction mixture was evacuated at rt for 10 m to remove TMDS. Dry THF (3.0 mL) was added followed by platinum(0)-1,3-divinyl-1,1,3,3-tetramethyldisiloxane complex (70 uL, in xylenes). The mixture was stirred at rt for 1.5 h (GC/MS monitoring indicated hydrosilylation was completed). To this mixture was added dropwise a solution of TBAF in THF (3.3 mL, 3.3 mmol, 2.2 equiv,). Iodobenzene (303 mg, 1.50 mmol, 1.0 equiv) and Pd(dba)$_2$ (84 mg, 0.15 mmol, 0.10 equiv) were added in one portion, successively to the mixture. The mixture was stirred at rt for 40 min. The reaction mixture was loaded onto 4 g of silica gel and was purified by column chromatography (SiO$_2$, 45 g, pentane/ether, 23/2) and Kugelrohr distillation afforded 257 mg (84%) of 214 as a colorless oil.

One-pot Arylation of 3-Octyn-1-ol with 4-Iodobenzene with 5% Pd(dba)$_2$. (E)-3-Phenyl-3-octen-1-ol 214

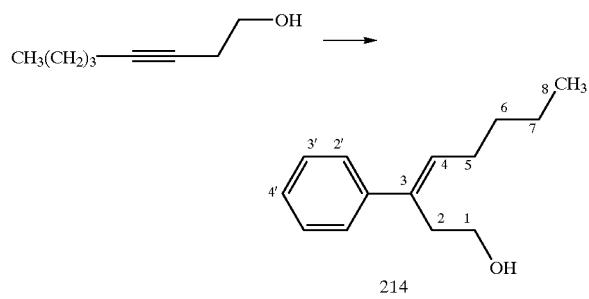

In a two-necked flask was placed 3-octyn-1-ol (246 mg, 1.90 mmol, 1.3 equiv) and tetramethyldisilazane (0.27 mL, 1.56 mmol, 1.04 equiv) was added dropwise at rt. The mixture was stirred for 1 h, then the mixture was evacuated at rt for 10 m to remove TMDS. Dry THF (3.0 mL) was added followed by platinum(0)-1,3-divinyl-1,1,3,3-tetramethyldisiloxane complex (50 uL, in xylenes). The mixture was stirred at rt for 1 h (GC/MS monitoring indicated hydrosilylation was completed). To this mixture was added dropwise a solution of TBAF in THF (3.3 mL, 3.3 mmol, 2.2 equiv). Iodobenzene (305 mg, 1.50 mmol, 1.0 equiv) and Pd(dba)$_2$ (42 mg, 0.15 mmol, 0.050 equiv) were added in one portion, successively to the mixture. The mixture was stirred at rt for 90 min. The reaction mixture loaded onto 4 g of silica gel and was purified by column chromatography (SiO$_2$, 46 g, pentane/ether, 23/2) and Kugelrohr distillation afforded 257 mg (85%) of 214 as a oil.

One-pot Arylation of 3-Octyn-1-ol with 4-Iodobenzene with 5% Pd(dba)$_2$ and Lower Hydrosilylation Concentration. (E)-3-Phenyl-3-octen-1-ol

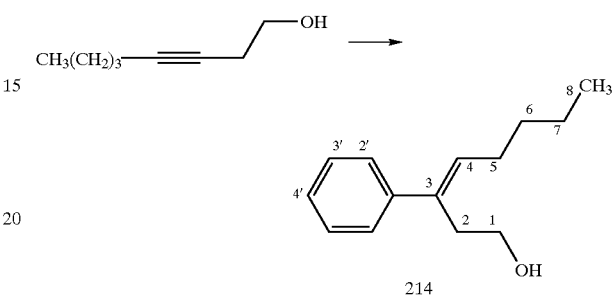

In a two-necked flask was placed 3-octyn-1-ol (246 mg, 1.95 mmol, 1.3 equiv) and tetramethyldisilazane (0.27 mL, 1,56 mmol, 1.04 equiv) was added dropwise at rt. The mixture was stirred for 1 h, then the mixture was evacuated at rt for 10 m to remove TMDS. Dry THF (10.0 mL) was added followed by platinum(0)-1,3-divinyl-1,1,3,3-tetramethyldisiloxane complex (30 uL, in xylenes). The mixture was stirred at rt for 2 h (GC/MS monitoring indicated hydrosilylation was completed), then was concentrated to 2.0 mL. To this mixture was added dropwise a solution of TBAF in THF (3.3 mL, 3.3 mmol, 2.2 equiv). Iodobenzene (303 mg, 1.50 mmol, 1.0 equiv) and Pd(dba)$_2$ (42 mg, 0.15 mmol; 0.050 equiv) were added in one portion, successively to the mixture. The mixture was stirred at rt for 90 min. The reaction mixture was loaded onto 4 g of silica gel and was purified by column chromatography (SiO$_2$, 56 g, pentane/ether, 9/1) afforded 275 mg of 214 as a yellow liquid. The NMR data matched those for the previous reaction, but the material was not pure. However, the isomeric ratio was not changed.

EXAMPLE 8

Cross-coupling of Vinylpolysiloxanes

A representative procedure for the cross-coupling of 1,3,5,7-tetramethyl-1,3,5,7-tetravinylcyclotetrasiloxane (92) with 4-iodoacetophenone follows. To a solution of 92 (207 mg, 0.6 mmol, 1.2 equivalents) in THF (0.2 ml) was added a solution of TBAF (Fluka, 1 M in THF, 4.0 ml). After 10 min, 4-iodoacetophenone (492 mg, 2.0 mmol) and Pd(dba)$_2$ (58 mg, 0.10 mmol, 5 mol %) were added sequentially. A strong exotherm was observed (the temperature of reaction solution increased from 24 to 55° C. within 6 min). After 10 min, GC analysis showed that the iodide was consumed (HP-5, 200° C., 15 psi: tR 6, 5.40 min). Diethyl ether (10 ml) was added and the mixture was stirred for an additional 5 min. The mixture was filtered though a short column of silica gel, which was further eluted with ether (50 ml). The combined eluate was concentrated by rotary evaporation and vacuum drying to give the crude product which was purified by silica gel chromatography (24×162 mm, pentane-ethyl acetate, 40:1) to afford 4-vinylacetophenone as a white solid 258 mg (88%).

Procedure II for the Cross-coupling of 92 with 4-iodoacetophenone

To a solution of 92 (207 mg, 0.6 mmol) in THF (0.2 ml) was added a solution of TBAF (Fluka, 1 M in THF, 4.0 ml). After 10 min, Pd(dba)$_2$ (58 mg, 0.10 mmol, 5 mol %) was added. Then a solution of 4-iodoacetophenone in THF (2.0 ml, 1.0 M) was slowly added by syringe such that the reaction temperature did not exceed 30° C. (45 min). After complete addition of 4-iodoacetophenone, the reaction mixture was stirred at room temperature for 10 min, whereupon GC analysis showed that the iodide was consumed. Ether (10 ml) was added and the mixture was stirred for an additional 5 min. The mixture was filtered though a short column of silica gel, then was eluted with ether (50 ml). The combined eluate was concentrated by rotary evaporation and vacuum drying to give the crude product which was purified by silica gel chromatography (24×155 mm, hexane-ethyl acetate, 40:1) to afford 4-vinylacetophenone as a white solid 233 mg (80%).

EXAMPLE 9

Hydrocarbation of Terminal Alkynes

General Experimental

Solutions of tetrabutylammonium fluoride (TBAF) in THF (1.0 M) employed in all descriptive runs were prepared from colorless crystalline tetrabutylammonium fluoride trihydrate (Fluka). Tetramethyldisiloxane was from Lancaster and directly used without further purification. Phenylacetylene (Aldrich) was distilled prior to use. All other alkynes, heptyne, 4-pentyn-1-ol (GFS) and 2-phenyl-3-butyn-1-ol (Fluka) were directly used without further purification. All the commercial halide reagents (Aldrich, ACROS) were purified by distillation or column chromatography prior to use. Allylpalladium chloride dimer [allylPdCl] 2 was purchased from ACROS. Platinum(0)-1,3-divinyl-1,1,3,3,-tetramethyldisiloxane complex, solution in xylene was purchased from Aldrich.

t-Bu 3 P—Pt(0) complex was prepared according to the literature procedure [1]: t-Bu 3 P (32 mg, 0.158 mmol) (Strem Chemicals) was dissolved in platinum(0)-1,3-divinyl-1,1,3,3-tetramethyldisiloxane complex (1.5 mL solution in xylene, Aldrich). The mixture was stirred at 65° C. (oil bath) for 5 min and then was slowly cooled to rt. This solution could be stored under N$_2$ in the freezer indefinitely.

Literature Preparations

The following compounds were prepared by literature methods: t-Bu$_3$ P—Pt(0) complex.[1] (E)-1-iodoheptene,[2] diethylethoxysilane,[3] 2-bromostyrene[4] and 5-(2-propenyloxy)-1-pentyne,[5] Pd(dba)$_2$,[6]

General Procedure I: One-pot Cross-coupling Reaction of Terminal Alkynes with Aryl or Alkenyl Halides To a solution of 1,1,3,3-tetramethyldisiloxane (0.65-t.8 mmol, 1.3/2–1.8/2 equiv) in THF was added t-Bu$_3$P—Pt(0) complex (25–50 μL). The neat alkyne (1.3–3.6 mmol, 1.3–1.8 equiv) was then slowly added with external cooling with a water bath (the temperature of reaction was not allowed to exceed 30° C.). The hydrosilylation mixture was stirred at rt for 30 min after the complete addition of the alkyne.

A solution of TBAF (Fluka, 1.0 M in THF, 2.0–6.0 mmol, 2.0–3.0 equiv) was added to above solution. After 10 min, the aryl or alkenyl halide (1.0–2.0 mmol, 1.0 equiv), Pd(dba)$_2$ (5 mol %) and (if required) Ph$_3$As (10 mol %) were sequentially added. A strong exotherm was observed. The reaction was monitored by GC or GC-MS. When the halide was consumed, ether (10 mL) was then aided and the mixture was stirred for an additional 5 min. The mixture was filtered through a short column of silica gel, then was eluted with ether (50–120 mL). The combined eluate was concentrated by rotary evaporation and vacuum drying to give the crude product which was purified by silica gel chromatography or RP chromatography and Kugelrohr distillation to afford the product.

General Procedure II: One-pot Cross-coupling Reaction of Terminal Alkyne and Aryl Halides, Reverse Order To a solution of 1,1,3,3-tetramethyldisiloxane (0.65–1.95 mmol, 1.3/2–1.95/2 equiv) in THF was added t-Bu$_3$P—Pt(0) complex (25–50 μL). The neat alkyne (1.3–3.0 mmol, 1.3–1.5 equiv) was then slowly added with external cooling with a water bath (the temperature of reaction was not allowed to exceed 30° C.). The hydrosilylation mixture was stirred at rt for 30 min after the complete the addition of the alkyne.

A solution of TBAF (Fluka, 1.0 M in THF, 4.0–6.0 mmol, 2.0–3.0 equiv) was added to above solution. After 10 min, Pd(dba)$_2$ (57.5 mg, 0.10 mmol, 5 mol %) was added. A solution of the aryl iodide (2.0 mmol, 1.0 equiv) in THF (2.0 mL, 1.0 M) was then slowly added by syringe such that temperature of reaction solution did not exceed 30° C. (addition time is about 45 min). The reaction mixture was stirred at room temperature and was monitored by GC. When the iodide was consumed, ether (10 mL) was then added and the mixture was stirred for an additional 5 min, The mixture was filtered through a short column of silica gel, then was eluted with ether. The combined eluate was concentrated by rotary evaporation and vacuum drying to give the crude product which was purified by silica gel chromatography and Kugelrohr distillation to afford the product.

Preparation of 1-[4-((1E)-2-phenylethenyl)phenyl]ethanone

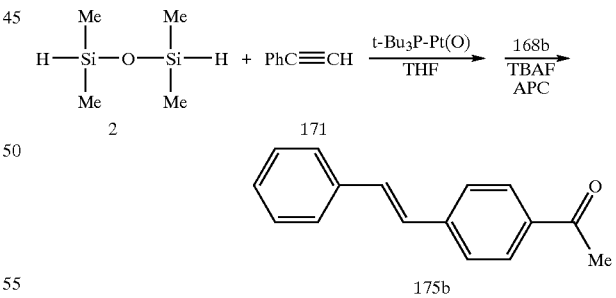

Following General Procedure I, a solution of 1,1,3,3-tetramethyldisiloxane (96 mg, 0.72 mmol, 1.43/2 equiv), t-Bu$_3$P—Pt(0) complex (25 μL) and phenylacetylene (133 mg, 1.3 mmol, 1.3 equiv) in 0.15 mL of THF was stirred at rt for 30 min. A solution of TBAF in THF (2.0 mL, 1.0 M, 2.0 equiv), 4-iodoacetophenone (246 mg, 1.0 mmol, 1.0 equiv) and [allylPdCl]$_2$ (9.1 mg, 2.5 mol %) were added and the mixture was stirred at rt for 10 min. Ether (10 mL) was added, then the mixture was filleted through a short column of SiO$_2$, which was eluted with ether (100 ml) and then was concentrated. Purification of the crude product by column chromatography on silica gel (pentane/EtOAc, 30/1) afforded 197 mg (89%) of 175h as a white solid Preparation of (E)-1-Heptenyl)naphthalene

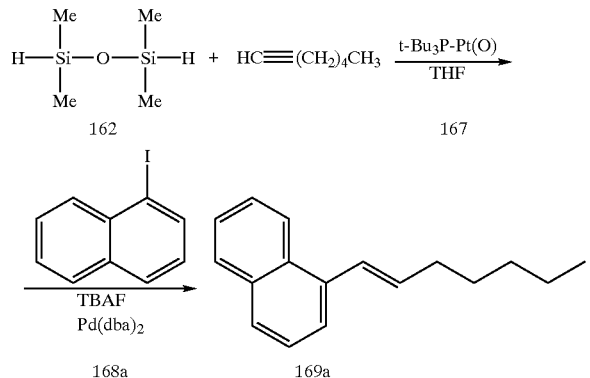

Following General Procedure I, a solution of 1,1,3,3-tetramethyldisiloxane (175 mg, 1.3 mmol, 1.3/2 equiv), t-Bu$_3$P—Pt(0) complex (50 µL) and heptyne (250 mg, 2.6 mmol, 1.3 equiv) in 0.2 mL of THF was stirred at rt for 30 min. A solution of TBAF in THF (4.0 mL, 1.0 M, 2,0 equiv), 1-iodonaphthalene (508 mg, 2.0 mmol, 1.0 equiv) and Pd(dba)$_2$ (57.5 mg, 5 mol %) were added and the mixture was stirred at rt for 10 min. Ether (10 mL) was added, then the mixture was filtered through a short column of SiO$_2$, which was eluted with ether (50 mL) and then was concentrated. Purification of the residue by column chromatography on silica gel (pentane) and RPC (C18, MeOH/H$_2$O, 9/1) followed by Kugelrohr distillation afforded 366.6 mg (82%) of 169a as colorless oil.

References (1) Chandra, G.; Lo, P, Y.; Hitchcock P. B.; Lappert, M. F. *Organometallics* 1987, 6, 191.

(2) Zweifel, G., Whitney, C. C. *J. Am, Chem. Soc.* 1967, 89, 2753.

(3) Ojima L; Kogure, T.; Nihonyanagi, M,; Kono, H.; Inaba, S.; Nagai, Y. *Chem. Let.* 1973, 501.

(4) Lloyd-Jones, G. C.; Butts, C. P. *Tetrahedron* 1998, 54, 901.

(5) (a) Harvey, D. F.; Lund, K. P.; Neil, D. A. *J. Am. Chem. Soc.* 1992, 114, 8424; (b) Daniel, D.; Middleton R.; Henry, H. L.; Okamura W. H. *J. Org. Chem.* 1996, 61, 5617.

(6) Ukai, T,; Kawazura,; H; Ishii Y. J. *Organomet. Chem.* 1974, 65, 253.

EXAMPLE 10

Fluorine-free Cross-coupling Reactions

General Procedure I: Palladium-catalyzed, Cross-coupling Reaction of (E)- or (Z)-(1-Heptenyldimethylsilanol ((E)-21) with 1-Iodonaphthalene using Various Activators

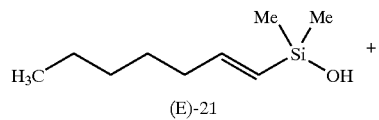

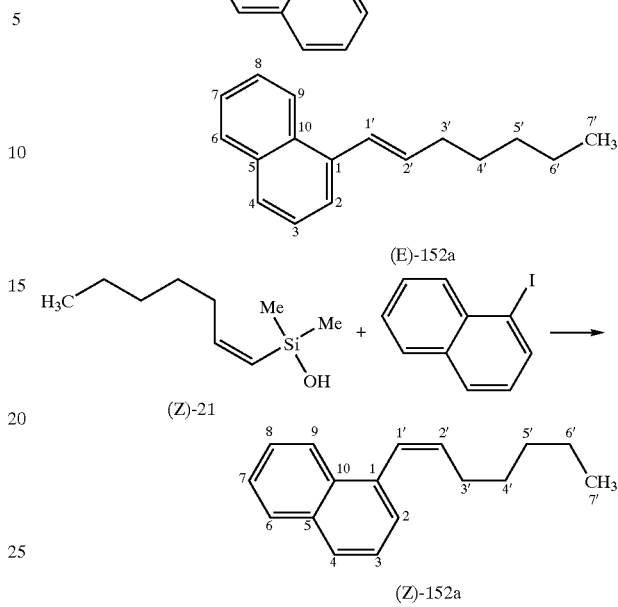

The activator (4.0 mmol 2.0 equiv) was dissolved or suspended in dry solvent (4 mL) at room temperature under an atmosphere of dry argon. To this solution was added in the following order; the silanol (2.0 mmol, 1.0 equiv), 1-iodonaphthalene (2.0 mmol) and then the palladium catalyst (5 mol %). The mixture was stirred at room temperature for 15 min–5 h. The reaction mixture was then filtered through a short silica gel column (20 g) The plug was eluted with diethyl ether (100 ml) and the eluate was evaporated in vacuo. The residue was purified by column chromatography (Reverse Phase C18 or SiO$_2$, 25 g) to afford the corresponding product which was further purified by bulb-to-bulb distillation.

Reaction of (E)-21 with 1-Iodonaphthalene using MeLi in THF [Table 20, entry 1]

Following General Procedure I, a solution of MeLi in ether (2.5 mL of a 1.6 M solution 4.0 mmol, 2.0 equiv), (E)-21 (344 mg, 2.0 mmol, 1.0 equiv), 1-iodonaphthalene (292 µL, 2.0 mmol) and Pd(dba)$_2$ (58 mg, 0.1 mmol, 0.05 equiv) was stirred in THF (4 mL) at room temperature for 24 h, and then was filtered through SiO$_2$. Purification by column chromatography (RP C18, MeOH/H$_2$O, 9/1) afforded 241 mg (47%) of 1-iodonaphthalene and 113 mg) (40%) of 1-methylnaphthalene.

Reaction of (E)-21 with 1-Iodonaphthalene using NaH and Hexamethyldisilazane in THF [Table 20, entry 2]

Following General Procedure I, a mixture of hexane washed NaH (96 mg, 4.0 mmol, 2.0 equiv), hexamethyldisiloxane (106 µL, 0.5 mmol, 0.25 equiv), (E)-21 (344 mg, 2.0 mmol, 1.0 equiv), 1-iodonaphthalene (292 µL, 2.0 mmol) and Pd(dba)$_2$ (58 mg, 0.1 mmol, 0.05 equiv) was stirred in DMF (4 mL) at room temperature for 7 h, and then was filtered through SiO$_2$. Purification by column chromatography (RP C18, MeOH/H$_2$O, 9/1) afforded 363 mg (81%) of (E)-152a as colorless oil.

Reaction of (E)-21 with 1-Iodonaphthalene using NaH in DMF [Table 20, entry 3]

Following General Procedure I, a mixture of hexane washed NaH (96 mg, 4.0 mmol, 2.0 equiv), (E)-21 (344 mg, 2.0 mmol, 1.0 equiv), 1-iodonaphthalene (292 µL, 2.0 mmol) and Pd(dba)$_2$ (58 mg, 0.1 mmol, 0.05 equiv) was stirred in DMF (4 mL) at room temperature for 90 min, and then was filtered through SiO$_2$. Purification by column chromatography (RP C18, MeOH/H$_2$O, 9/1) afforded 359 mg (78%) of (E)-152a as colorless oil.

Reaction of (E)-21 with 1-Iodonaphthalene using NaH in DME [Table 20, entry 4]

Following General Procedure I, a mixture of hexane washed NaH (96 mg, 4.0 mmol, 2.0 equiv), (E)-21 (344 mg, 2.0 mmol 1.0 equiv), 1-iodonaphthalene (292 µL, 2.0 mmol) and Pd(dba)$_2$ (58 mg, 0.1 mmol, 0.05 equiv) was stirred in DME (4 mL) at room temperature for 60 min, and then was filtered through SiO$_2$. Purification by column chromatography (RP C18, MeOH/H$_2$O, 9/1) afforded 365 mg (81%) of (E)-152a as colorless oil.

Reaction of (E)-21 with 1-Iodonaphthalene using KH in THF [Table 20, entry 5]

Following General Procedure I, a mixture of hexane washed KH (160 mg, 4.0 mmol) and 2.0 equiv), (E)-21 (344 mg, 2.0 mmol, 1.0 equiv), 1-iodonaphthalene (292 µL, 2.0 mmol) and Pd(dba)$_2$ (58 mg, 0.1 mmol, 0.05 equiv) was stirred in THF (4 mL) at room temperature for 120 min, and then was filtered through SiO$_2$. Purification by column chromatography (RP C18, MeOH/H$_2$O, 9/1) afforded 381 mg (85%) of (E)-152a as colorless oil.

Reaction of (E)-21 with 1-Iodonaphthalene using KH in DME [Table 20, entry 6]

Following General Procedure I, a mixture of hexane washed KH (160 mg, 4.0 mmol, 2.0 equiv), (E)-21 (344 mg, 2.0 mmol, 1.0 equiv), 1-iodonaphthalene (292 µL, 2.0 mmol) and Pd(dba)$_2$ (58 mg, 0.1 mmol, 0.05 equiv) was stirred in DME (4 mL) at room temperature for 15 min, and then was filtered through SiO$_2$. Purification by column chromatography (RP C18, MeOH/H$_2$O, 9/1) afforded 370 mg (82%) of (E)-152a as colorless oil.

Reaction of (E)-21 with 1-Iodonaphthalene using KOtBu in DME [Table 20, entry 7]

Following General Procedure I, a mixture KOtBu (449 mg, 4.0 mmol, 2.0 equiv), (E)-21 (344 mg, 2.0 mmol, 1.0 equiv), 1-iodonaphthalene (292 µL, 2.0 mmol) and Pd(dba)$_2$ (58 mg, 0.1 mmol, 0.05 equiv) was stirred in DME (4 mL) at room temperature for 180 min, and then was filtered through SiO$_2$. Purification by column chromatography (RP C18, MeOH/H$_2$O, 9/1) afforded 403 mg (90%) of (E)-152a as colorless oil.

General Procedure II: Palladium-catalyzed Cross-coupling Reaction of Alkenylsilanes with Aryl Halides Potassium trimethylsilanoate (90%) (4.0 mmol, 2.0 equiv) was dissolved in dry DME (4 mL) at room temperature under an atmosphere of dry argon. To this solution was added the neat silanol (2.2 mmol, 1.1 equiv) followed by the aryl iodide (2.0 mmol), and then the palladium catalyst (5 mol %. The mixture was stirred at room temperature for 15 min–14 h. The reaction mixture was then filtered through a short silica gel column (20 g) The plug was eluted with diethyl ether (100 mL) and the eluate was evaporated in vacuo. The residue was purified by column chromatography (Reverse Phase C18 or SiO$_2$, 25 g) to afford the corresponding product which was further purified by bulb-to-bulb distillation.

Reaction of (Z)-21 with 1-Iodonaphthalene using KH in DME [Table 21, entry 1]

Following General Procedure I, a mixture of hexane washed KH (160 mg, 4.0 mmol, 2.0 equiv), (Z)-21 (344 mg, 2.0 mmol, 1.0 equiv), 1-iodonaphthalene (292 µL, 2.0 mmol) and Pd(dba)$_2$ (58 mg, 0.1 mmol, 0.05 equiv) was stirred in DME (4 mL) at room temperature for 15 min, and then was filtered through SiO$_2$. Purification by column chromatography (RP C18, MeOH/H$_2$O, 9/1) afforded 219 mg (49%) of (Z)-152a and 77 mg (30%) of naphthalene.

Reaction of (Z)-21 with 1-Iodonaphthalene using KOtBu in DME [Table 21, entry 2]

Following General Procedure I, a mixture KOtBu (449 mg, 4.0 mmol 2.0 equiv), (Z)-21 (344 mg, 2.0 mmol, 1.0 equiv), 1-iodonaphthalene (292 µL, 2.0 mmol) and Pd(dba)$_2$ (58 mg, 0.1 mmol, 0.05 equiv) was stirred in DME (4 mL) at room temperature for 24 h, and then was filtered trough SiO$_2$. Purification by column chromatography (RP C18, MeOH/H$_2$O, 9/1) afforded 238 mg (53%) of (Z)-152a.

Reaction of (Z)-21 with 1-Iodonaphthalene using KOSiMe$_3$ in DME [Table 21, entry 3]

Following General Procedure I, a mixture of KOSiMe$_3$ (570 mg 4.0 mmol, 2.0 equiv), (Z)-21 (344 mg, 2.0 mmol, 1.0 equiv), 1-iodonaphthalene (292 µL, 2.0 mmol) and Pd(dba)$_2$ (58 mg, 0.1 mmol, 0.05 equiv) was stirred in DME (4 mL) at room temperature for 24 h, and then was filtered through SiO$_2$. Purification by column chromatography (RP C18, MeOH/H$_2$O, 9/1) afforded 394 mg (88%) of (Z)-152a.

Preparation of (E)-1-(Heptenyl)naphthalene ((E)-154a) [Table 22, entry 1]

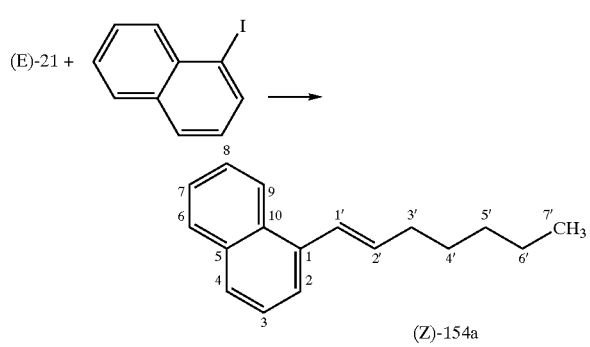

Following General Procedure II, a mixture of KOSiMe$_3$ (570 mg, 4.0 mmol, 2.0 equiv), (E)-21 (379 mg, 2.2 mmol, 1.1 equiv), 1-iodonaphthalene (292 µL, 2.0 mmol) and Pd(dba) (58 mg, 0.1 mmol, 0.05 equiv) was stirred at room temperature for 2 h, and then was filtered through SiO$_2$. Purification by column chromatography (RP C18, MeOH/H$_2$O, 9/1) and Kugelrohr distillation afforded 416 mg (93%) of (E)-154a as colorless oil.

Preparation of (Z)-1-(1-Heptenyl)naphthalene ((Z)-154a) [Table 22, entry, 2]

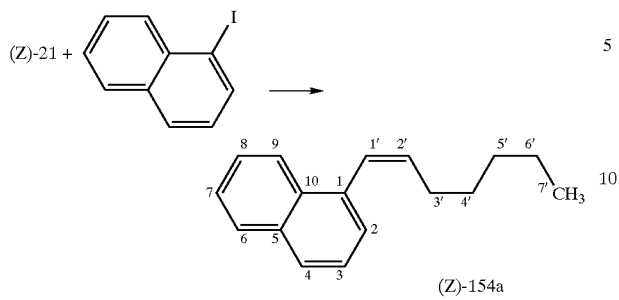

Following General Procedure II, a mixture of KOSiMe$_3$ (570 mg, 4.0 mmol, 2.0 equiv), (Z)-21 (379 mg, 2.2 mmol, 1.1 equiv), 1-iodonaphthalene (292 µL, 2.0 mmol) and Pd(dba)2 258 mg, 0.1 mmol, 0.05 equiv) was stirred at room temperature for 9 h, and then was filtered through SiO$_2$. Purification by column chromatography (RP C18, MeOH/H$_2$O, 9/1) and Kugelrohr distillation afforded 394 mg (88%) of (Z)-154a as colorless oil.

Preparation of (E)-1-Heptenylbenzene ((E)-154b) [Table 22, entry 3]

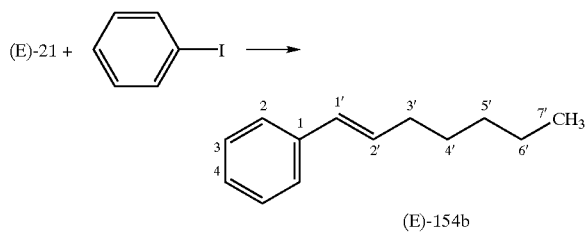

Following General Procedure II, a mixture of KOSiMe$_3$ (570 mg, 4.0 mmol, 2.0 equiv), (E)-21 (379 mg, 2.2 mmol, 1.1 equiv), iodobenzene (224 µL, 2.0 mmol) and Pd(dba$_2$) (58 mg, 0.1 mmol, 0.05 equiv) was stirred at room temperature for 0.5 h, and then was filtered through SiO$_2$. Purification by column chromatography (RP C18, MeOH/H$_2$O, 9/1) and Kugelrohr distillation afforded 318 mg (91%) of (E)-154b as colorless oil.

Preparation of (Z)-21-Heptenylbenzene ((Z)-154b) [Table 22, entry 4]

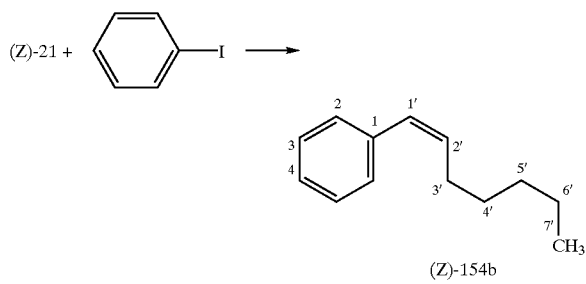

Following General Procedure II, a mixture of KOSiMe$_3$ (570 mg, 4.0 mmol, 2.0 equiv), (Z)-21 (379 mg, 2.2 mol, 1.1 equiv), iodobenzene (1.0 mmol) and Pd(dba)$_2$ (58 mg, 0.1 mmol, 0.05 equiv) was stirred at room temperature for 7.5 h, and then was filtered through SiO$_2$. Purification by column chromatography (RP C18, MeOH.H$_2$O, 9/1) and Kugelrohr distillation afforded 298 mg (86%) of (Z)-154b as colorless oil.

Preparation of (E)-1-[4-(1-Heptenyl)phenyl]ethanone ((E)-154c) [Table 22, entry 5]

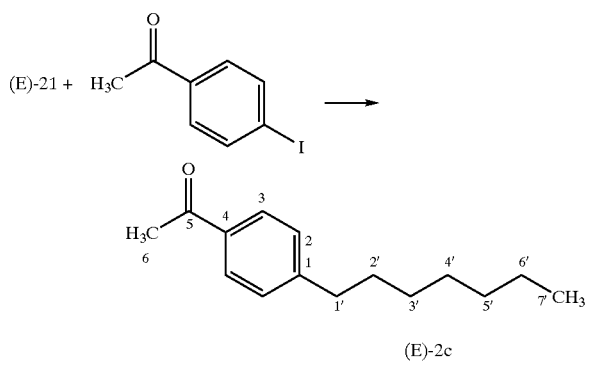

Following General Procedure II, a mixture of KOSiMe$_3$ (570 mg, 4.0 mmol, 2.0 equiv), (E)-21 (379 mg, 2.2 mmol, 1.1 equiv), 4-iodoacetophenone (492 mg, 2.0 mmol) and Pd(dba$_2$) (58 mg, 0.1 mmol, 0.05 equiv) was stirred at room temperature for 9 h, and then was filtered through SiO$_2$. Purification by column chromatography (RP C18, MeOH/H$_2$O, 9/1) and Kugelrohr distillation afforded 354 mg (82%) of (E)-154c as colorless oil.

Preparation of (Z)-1-[4-(1-Heptenyl)phenyl]ethanone [Table 22, entry 6]

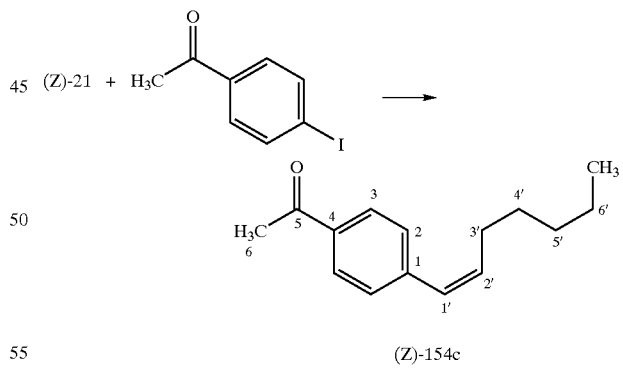

Following General Procedure II, a mixture of KOSiMe$_3$ (570 mg, 4.0 mmol, 2.0 equiv), (Z)-21 (379 mg, 2.2 mmol, 1.1 equiv), 4-iodoacetophenone (492 mg, 2.0 mmol) and Pd(dba$_2$) (58 mg, 0.1 mmol, 0.05 equiv) was stirred at room temperature for 13 h, and then was filtered through SiO$_2$. Purification by column chromatography (RP C18, MeOH/H$_2$O, 9/1) and Kugelrohr distillation afforded 360 mg (83%) of (Z)-154c as colorless oil.

Preparation of (E)-1-(1-Heptenyl)-4-methoxybenzene ((E)-154d) [Table 22, entry 7]

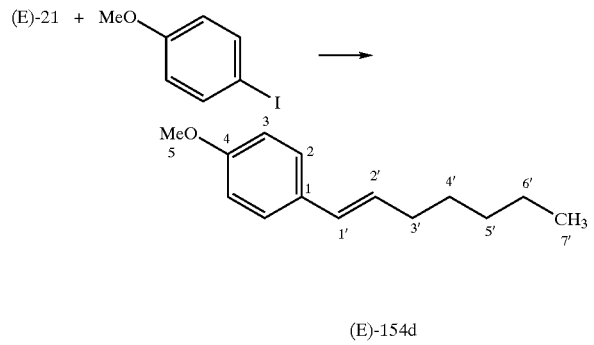

(E)-154d

Following General Procedure II, a mixture of KOSiMe₃ (570 mg, 4.0 mmol, 2.0 equiv), (E)-21 (379 mg, 2.2 mmol, 1.1 equiv), 4-iodoanisole (468 mg, 2.0 mmol) and Pd(dba₂) (58 mg, 0.1 mmol, 0.05 equiv) was stirred at room temperature for 1 h, and then was filtered through SiO₂. Purification by column chromatography (RP C18, MeOH/H₂O, 9/1) and Kugelrohr distillation afforded 361 mg (88%) of (E)-154d as colorless oil.

Preparation of (Z)-1-(1-Heptenyl)-4-methoxybenzene ((Z)-154d) [Table 22, entry 8]

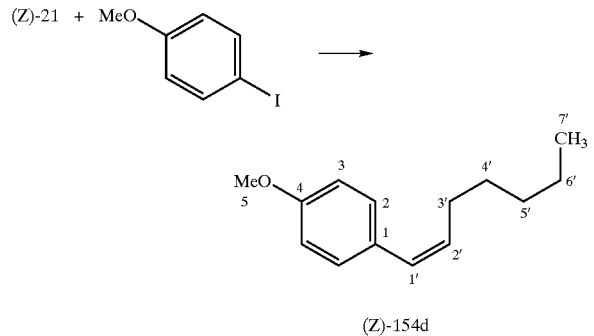

(Z)-154d

Following General Procedure II, a mixture of KOSiMe₃ (570 mg, 4.0 mmol, 2.0 equiv), (Z)-21 (379 mg, 2.2 mmol, 1.1 equiv), 4-iodoanisole (468 mg, 2.0 mmol ), and Pd(dba₂) (58 mg, 0.1 mmol, 0.05 equiv) was stirred at room temperature for 9.5 h, and then was filtered through SiO₂. Purification by column chromatography (RP C18, MeOH/H₂O, 9/1) and Kugelrohr distillation afforded 373 mg (91% ) of (Z)-154d as colorless oil.

Preparation of (E)-(1-Heptenyl)-4-nitrobenzene ((E)-154e) [Table 22, entry 9]

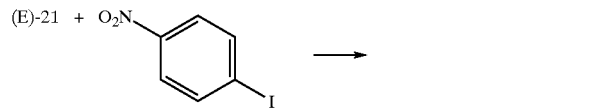

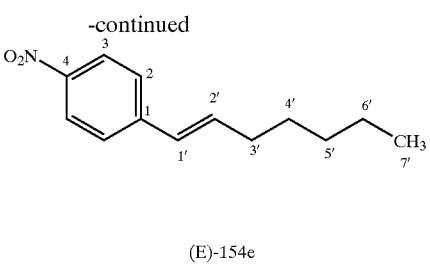

(E)-154e

Following General Procedure II, a mixture of KOSiMe₃ (570 mg , 4.0 mmol, 2.0 equiv), (E)-21 (379 mg, 2.2 mmol, 1.1 equiv), 1-iodo-4-nitrobenzene (498 mg, 2.0 mmol) and Pd(dba₂) (58 mg, 0.1 mmol, 0.05 equiv) was stirred at room temperature for 15 min, and then was filtered through SiO₂. Purification by column chromatography (RP C18, MeOH/H₂O, 9/1) and Kugelrohr distillation afforded 415 mg (95%) of (E)-154e as colorless oil.

Preparation of (Z)-(1-Heptenyl)-4-nitrobenzene ((Z)-154e) [Table 22, entry 10]

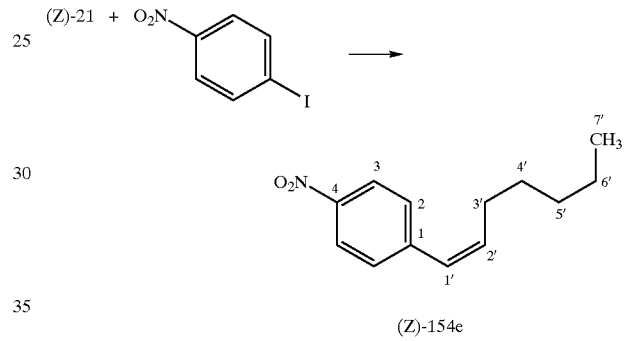

(Z)-154e

Following General Procedure II, a mixture of KOSiMe₃ (570 mg, 4.0 mmol, 2.0 equiv), (Z)-21 (379 mg, 2.2 mmol, 1.1 equiv), 1-iodo-4-nitrobenzene (498 mg, 2.0 mmol) and Pd(dba₂) (58 mg, 0.1 mmol, 0.05 equiv) was stirred at room temperature for 15 min, and then was filtered through SiO₂. Purification by column chromatography (RP C18, MeOH/H₂O, 9/1) and Kugelrohr distillation afforded 374 mg (85%) of (Z)-154e as colorless oil.

Preparation of Ethyl-(E)-4-(1-heptenyl)benzoate ((E)-154f) [Table 22, entry 11]

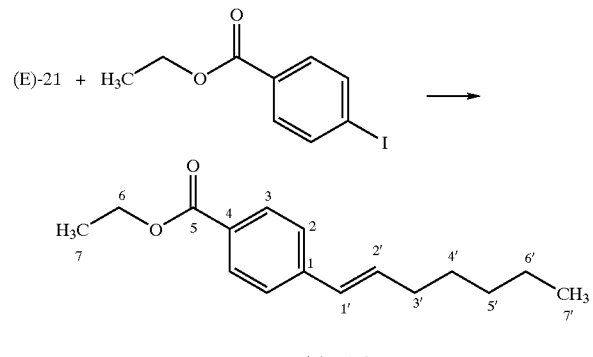

(E)-154f

Following General Procedure II, a mixture of KOSiMe₃ (570 mg, 4.0 mmol, 2.0 equiv), (E)-21 (379 mg, 2.2 mmol, 1.1 equiv), ethyl-4-iodobenzoate (2.0 mmol) and Pd(dba)2 (58 mg, 0.1 mmol, 0.05 equiv) was stirred at room temperature for 15 min, and then was filtered through SiO₂. Purification by column chromatography (SiO₂, Hexane/Ethyl Acetate, 50/1) and Kugelrohr distillation afforded 413 mg (84%) of (E)-154f as colorless oil.

Preparation of Ethyl-(Z)-4-(1-heptenyl)benzoate ((Z)-154f) [Table 22, entry 12]

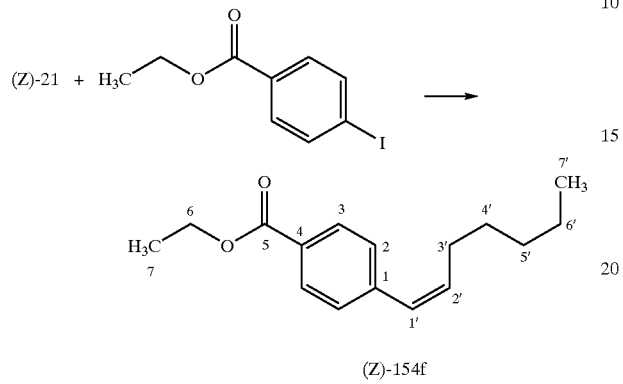

(Z)-154f

Following General Procedure II, a mixture of KOSiMe₃ (570 mg, 4.0 mmol, 2.0 equiv), (Z)-21 (379 mg, 2.2 mmol, 1.1 equiv), ethyl-4-iodobenzoate (2.0 mmol) and Pd(dba)2 (58 mg, 0.1 mmol, 0.05 equiv) was stirred at room temperature for 15 min, and then was filtered through SiO₂. Purification by column chromatography (RP C18, MeOH/H₂O, 9/1) and Kugelrohr distillation afforded 411 mg (83%) of (Z)-154f as colorless oil.

Preparation of (1,1-Dimethylethyl)[(2-(E)-(1-heptenylphenyl))methoxy]dimethylsilane ((E)-154g) [Table 22, entry 13]

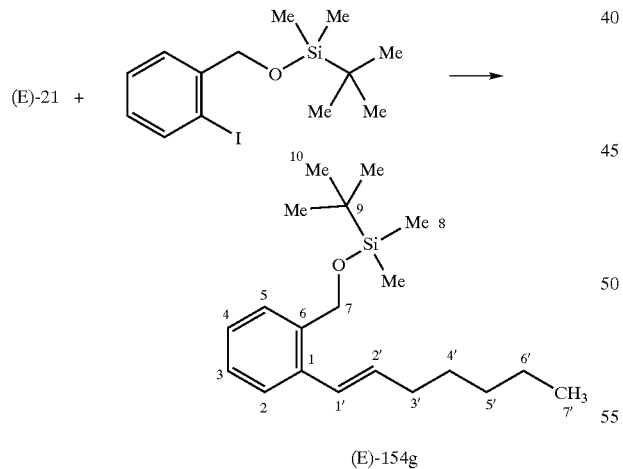

(E)-154g

Following General Procedure II, a mixture of KOSiMe₃ (570 mg, 4.0 mmol, 2.0 equiv), (E)-21 (379 mg, 2.2 mmol, 1.1 equiv), ethyl-4-iodobenzoate (696 mg, 2.0 mmol) and Pd(dba₂) (58 mg, 0.1 mmol, 0.05 equiv) was stirred at room temperature for 2 h, and then was filtered through SiO₂. Purification by column chromatography (RP C18, MeOH/H₂O, 9/1) and Kugelrohr distillation afforded 510 mg (80%) of (E)-154g as colorless oil.

Preparation of (1,1-Dimethylethyl)[(2-(Z)-(1-heptenylphenyl))methoxy]dimethylsilane ((Z)-154g) [Table 22, entry 14]

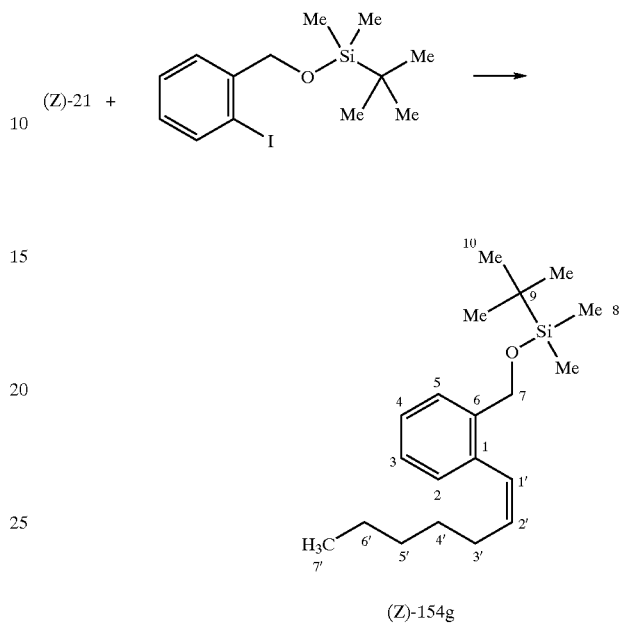

(Z)-154g

Following General Procedure II, a mixture of KOSiMe₃ (570 mg, 4.0 mmol, 2.0 equiv), (Z)-21 (379 mg, 2.2 mmol, 1.1 equiv), ethyl-4-iodobenzoate (696 mg, 2.0 mmol) and Pd(dba₂) (58 mg, 0.1 mmol, 0.05 equiv) was stirred at room temperature for 2 h, and then was filtered through SiO₂. Purification by column chromatography (RP C18, MeOH/H₂O, 9/1) and Kugelrohr distillation afforded 488 mg (76%) of (E)-154g as colorless oil.

Preparation of (1,1-Dimethylethyl)[(2-iodophenyl)methoxy]dimethylsilane.

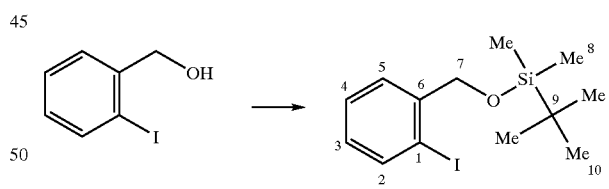

To a stirring solution of 2-iodobenzylalcohol (2.34 g, 10 mmol) in 50 mL DMF was added imidazole (1.02 g, 15 mmol, 1.5 equiv) and TBSCl (1.66 g, 11 mmol, 1.1 equiv). The mixture was stirred at room temperature for 5 h, then 40 mL of water was added. The mixture was transferred to a separatory funnel. The aqueous layer was separated and extracted with ether (2×40 mL). The combined organic layers were then washed with water (2×40 mL), dried with MgSO₄ and filtered. The solvent was removed in vacuo and the residue was purified by column chromatography and then Kugelrohr distillation to afford the product (3.107 g, 89%) as a clear colorless liquid.

All references cited herein are incorporated by reference herein to the extent that they are not inconsistent with the disclosures herein. References 18, 28, 29 and 30 (Appendix D) are each individually incorporated by reference in their entirety herein to the extent that they are not inconsistent herewith.

Further details of the cross coupling reactions of organosilicon reagents of this invention may be found in the following references as well as in references cited in the listed references:

Denmark, S. E. and Choi, J. Y. J. (1999) J. Am. Chem. Soc. 121:5821

Denmark, S. E. and Wu, Z. (1999) Org. Lett. 1:2137

Denmark, S. E. and Wang, Z. (2000) Synthesis, p. 999

Denmark S. E. and Wehrli, D. (2000) Org. Lett. 2:565

Denmark, S. E. and Neuville, L. (000) Org. Lett. 2:3221

Denmark, S. E. and Pan, W. (2001), Org. Lett. 3:61

Denmark, S. E. et al. (2000) Org. Lett. 2:2491

Denmark, S. E. and Wang, Z. (2001) J. Organometall. Chem. 624:372–375

Denmark, S. E. and Wang, Z. (2001) Organ. Lett. 3(7):1073–1076

Denmark S. E. and Yang, S-M. (2001) Organ. Lett. 3(11):1749–1752

These references may include additional information on starting materials, reagents, reaction conditions and purification procedures useful in the practice of this invention. All of these references and references cited therein are incorporated by reference herein to the extent that they are not inconsistent with the disclosures herein.

References 1. (a) Diederich, F., Stang, P. J., Eds. *Metal-Catalyzed, Cross-Coupling Reactions*; Wiley-VCH: Weinheim, 1998; (b) Heck, R. F. (1985) *Palladium Reagents in Organic Syntheses*; Academic Press: New York; (c) Tsuji, I.(1995) *Palladium Reagents and Catalysts. Innovations in Organic Synthesis*; Wiley: Chichester, U.K.
2. (a) Tamao, K. et al. (1972) *J. Am. Chem. Soc.* 94:4374; (b) Corriu, R. J. P. and Masse, J. P. (1972) *Chem. Commun.*, p. 144
3. (a) Miyaura, N. and Suzuki, A. (1995) *Chem Rev.* 95:2457; (b) Suzuki, A. (1998), in *Metal-Catalyzed, Cross-Coupling Reactions*; Diederich, F. et al. (eds.), Wiley-VCH; Weinheim, Chapter II.
4. (a) Stille, J. K. (1986) *Angew. Chem., Int. Ed. Engl.* 25:508; (b)Farina, V. et al. (1998) *J. Org. React.* 50:1; (c) Mitchell, T. N. (1998) in *Metal-Catalyzed, Cross-Coupling Reactions*; Diederich, F. et al. (eds), Wiley-VCH; Weinheim, Chapter 4.
5. Corriu, R. J. P and Masse, J. P. (1972) *Chem. Commun.*, p. 144
6. (a) Diederich, F., Stang, P. J., Eds. *Metal-Catalyzed, Cross-Coupling Reactions*; Wiley-VCH: Weinheim, 1998; (b) Heck, R. F. (1985) *Palladium Reagents in Organic Syntheses*; Academic Press: New York; (c) Tsuji, I.(1995) *Palladium Reagents and Catalysts. Innovations in Organic Synthesis*; Wiley: Chichester, U.K.
7. Hatanaka, Y. and Hiyama, T. (1991) *Synlett*, p. 845
8. Hiyama, T. in *Metal-Catalyzed, Cross-Coupling Reactions*; Diederich, F. et al. (eds.), Wiley-VCH; Weinheim (1998); Chapter 10.
9. Horn, K. A. (1995) *Chem. Rev.*, pp. 95, 1317.
10. Mowery, M. E. and DeShong, P. (1999) *J. Org. Chem.* 64:1684.
11. Hiyama, T. and Hatanaka, Y. (1994) *Pure Appl. Chem.* 66:1471
12. Shibata, K. et al. (1997) *Chem. Commun.*, p. 1309
13. Hirabayashi, K. et al. (1999) *Org. Lett.* 1:299.
14. Matsumoto, D. et al. (1995) *Bull. Chem. Soc. Jpn.* 68:250.
15. Denmark, S. E. et al. (1994) *J. Am. Chem. Soc.* 116:7026.
16. Laane, J. (1967) *J. Am. Chem. Soc.* 89:1144.
17. 4(b) pp. 48–49 (above)
18. Denmark and Choi (1999) *JACS* 121:3821–3822.
19. Ikeyashira, K. et al. (1997) *J. Chem. Soc., Chem. Commun.*, p. 1039.
20. Littke, A. F. and Fu, G. C. (1998) *Angew. Chem. Int. Ed. Engl.* 37:3387
21. Aranyos, A. et al. (1999) *J. Am. Chem. Soc.* 121:4369.
22. Hirabayashi K. et al. (1998) *Bull Chem. Soc. Jpn.* 71:2409.
23. (a) Sieburth, S. McN. and Mu, W. (1993) *J. Org. Chem.* 58:6314; (b) Sieburth, S. McN. and Fensterbank, L. (1993) *J. Org. Chem.* 58:7584.
24. Kropp, P. J. and Crawford, S. D. (1994) *J. Org. Chem.* 59:3102
25. Miller, R. B. and McGarvey, G. (1978) *J. Org. Chem.* 43:4424.
26. Ravid, U. et al. (1978) *Tetrahedron* 34:1449.
27. Matos, K. and Soderquist, J. A. (1998) *J. Org. Chem.* 63:461
28. Denmark, S. E. and Wu, Z. (1999) *Org. Lett.* 1(9):1495–1498.
29. Denmark, S. E. and Wehrli, D. (2000) *Org. Lett.* 2(4):565–568.
30. Denmark, S. E. and Wang, Z. (2000) *Synthesis* (in press) (Attachment D)
31. Soderquist, J. A. and Hsu, G. J-H (1982) *organometallus* 1:830–833
32. Sieburth, S. McN. and Mu, W. (1993) *J. Org. Chem.* 58:6314–6318; Sieburth, S. McN. and Fensterbank, L. (1993) *J. Org. Chem.* 58:7584–7586
33. Chang, S. and Grubbs, R. H. (1997) Tetrahedron Lett. 38: 4757; Ahmed, M. et al. (1999) Tetrahedron 55:3219; Barrett, A. G. M. et al. (2000) J. Org. Chem. 65:6508; Kirkland, T. A. and Grubbs, R. H. (1997) J. Org. Chem. 62:7310
34. Furstner, A. (2000) Angew. Chem. Int. Ed. 39:3012; Grubbs, R. H. and Chang, S. (1998) Tetrahedron 54:4413; Schuster, M. and Blechert, S. (1997) Angew. Chem., Int. Ed. Engl. 36: 2036; Fursnter, A. (ed.) (1998), *Alkene Metathesis in Organic Synthesis*, Springer: Berlin
35. Ojima, I. et al. (1998), in *The chemistry of organic silicon compounds*, Rappoport, A., Apeloig, Y. (eds.), John Wiley & Sons: Great Britain, Vol. 2, pp. 1687–1792

Scheme 2
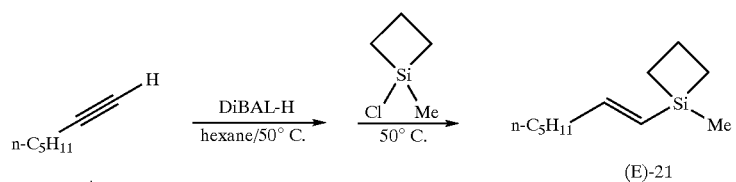
Scheme 3
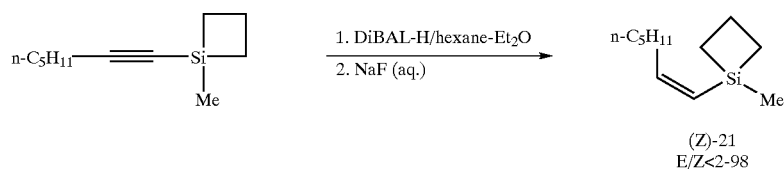
Scheme 4
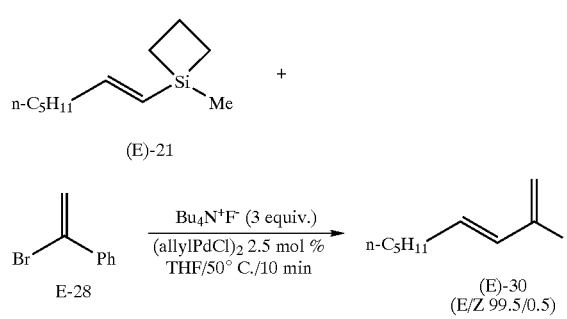
Me = Methyl
Ph = Phenyl
Scheme 5
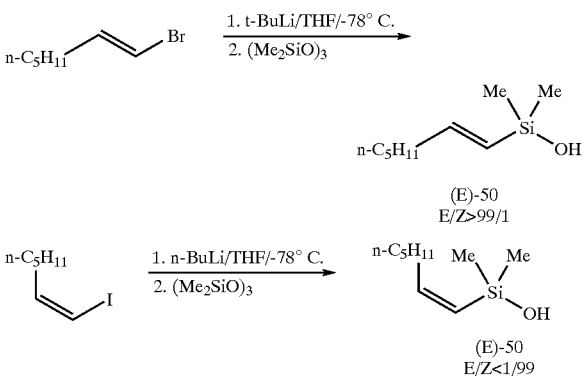
Scheme 6
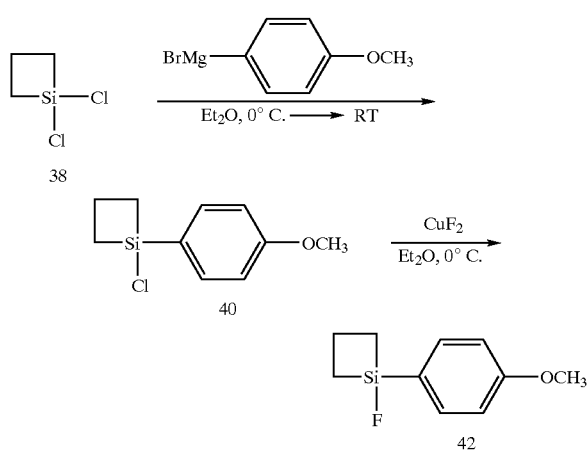
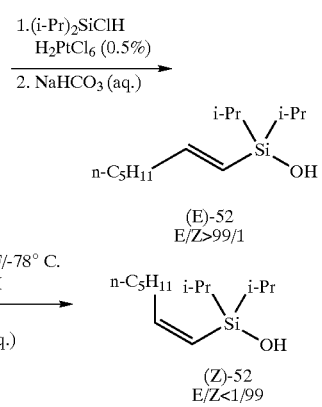
i-Pr = iso-propyl Scheme 7A and 7B
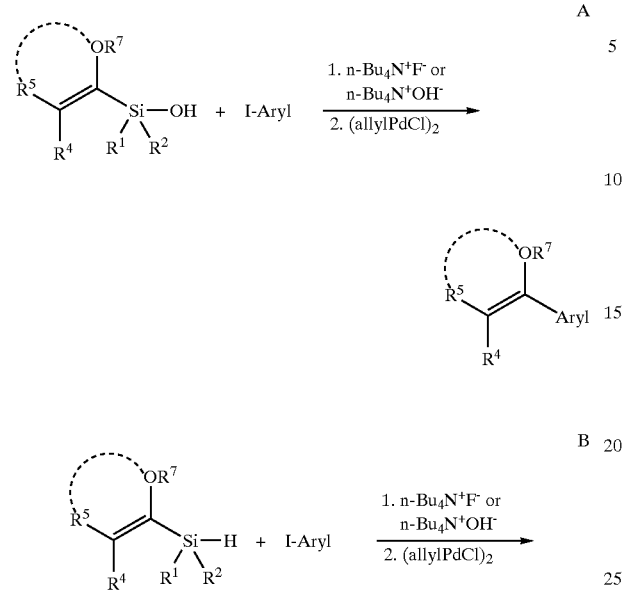
Exemplary T-siloxanes:
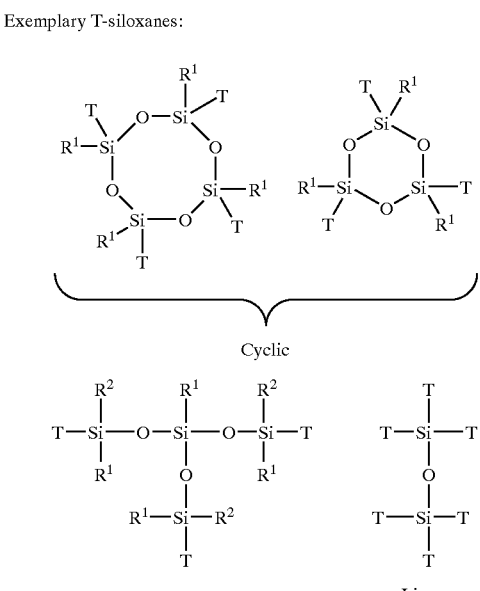
Scheme 8
Scheme 9
Scheme 10
Scheme 11
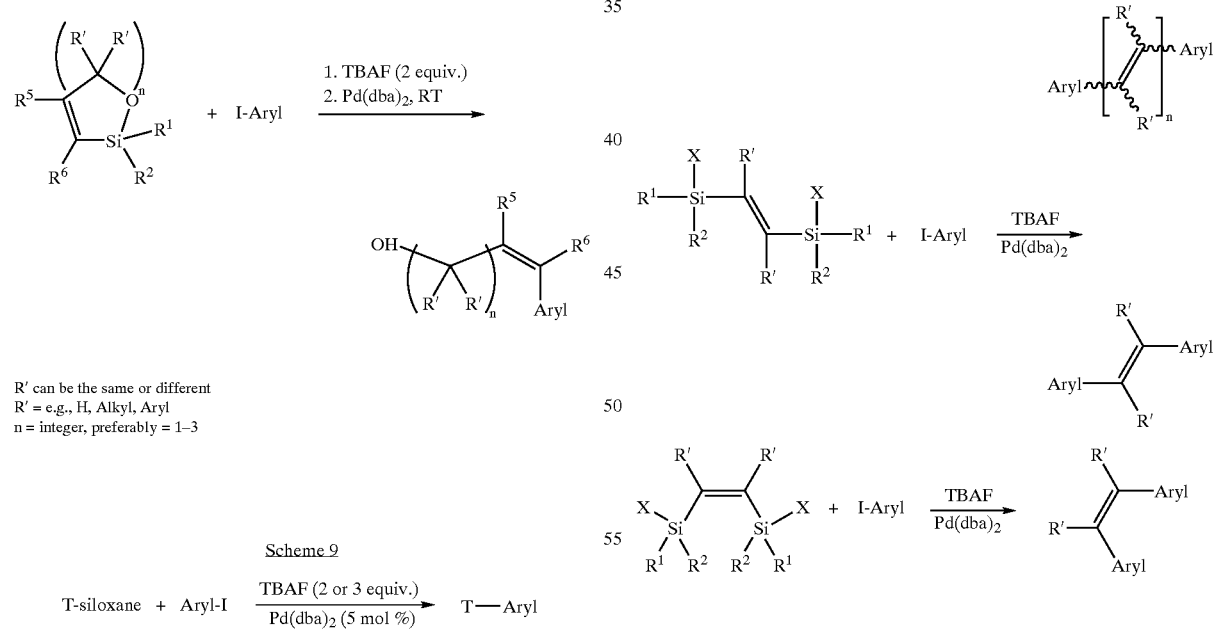
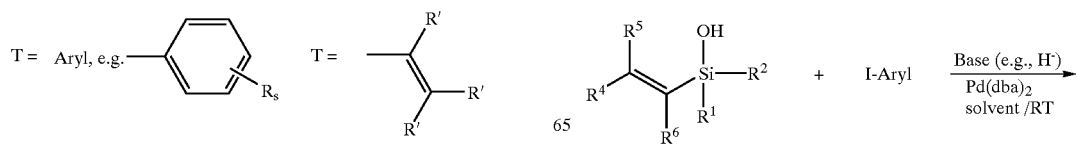
R' can be the same or different
R' = e.g., H, Alkyl, Aryl
n = integer, preferably = 1–3

Scheme 14
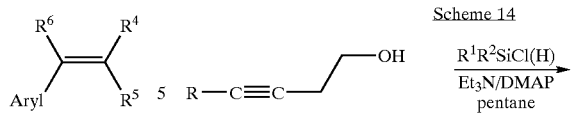
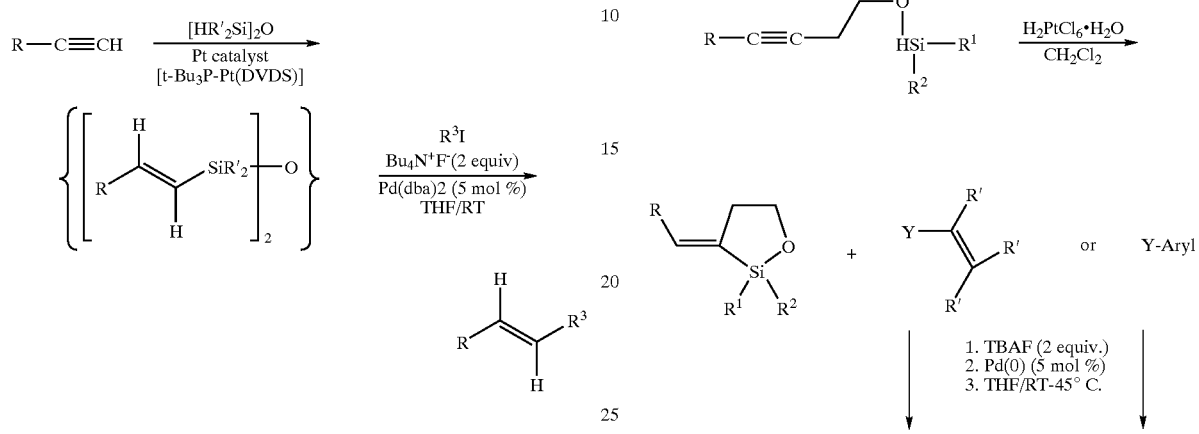
Scheme 12
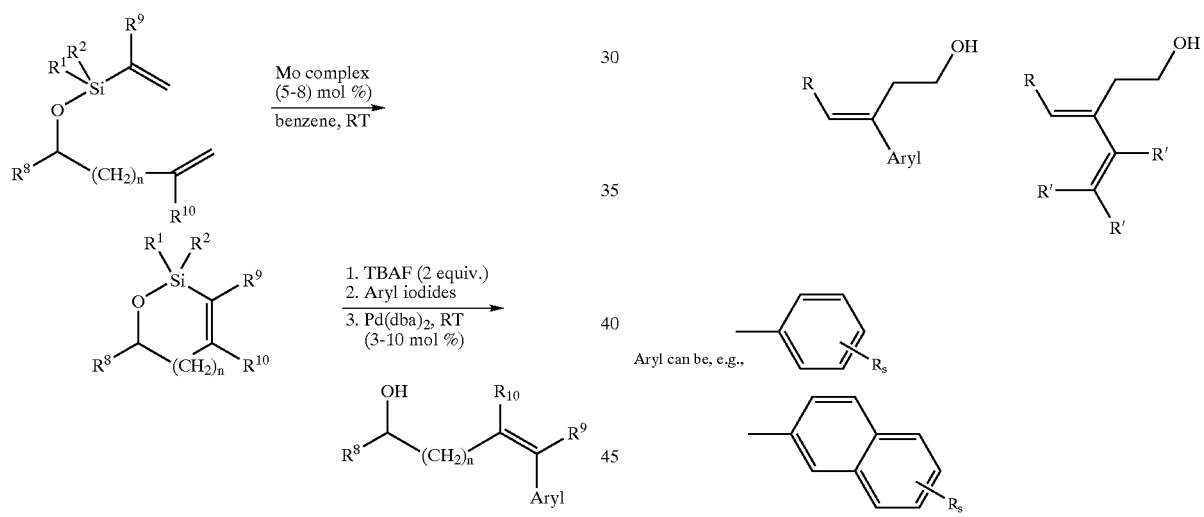
Scheme 13
TABLE 1
Pd-Catalyzed Coupling of (E)- and (Z)-21 with Aryl Iodides[a]
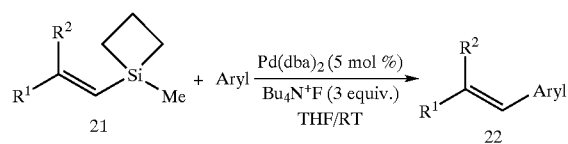
| entry | silane | $R^1$ | $R^2$ | aryl | time, min | product | yield, %[b] | ratio, E/Z[c] |
|---|---|---|---|---|---|---|---|---|
| 1 | (E)-21 | n-$C_5H_{11}$ | H | $C_6H_5$ | 10 | (E)-22a | 91 | 99.9/0.1 |
| 2 | (Z)-21 | H | n-$C_5H_{11}$ | $C_6H_5$ | 10 | (Z)-22a | 90 | 0.9/99.1 |
| 3 | (E)-21 | n-$C_5H_{11}$ | H | 1-naphthyl | 30 | (E)-22b | 93 | 99.8/0.2 |
| 4 | (Z)-21 | H | n-$C_5H_{11}$ | 1-naphthyl | 30 | (Z)-22b | 91 | 1.5/98.5 |
| 5[d] | (E)-21 | n-$C_5H_{11}$ | H | 2-thienyl | 180 | (E)-22c | 89 | 99.0/1.0 |
| 6[d] | (Z)-21 | H | n-$C_5H_{11}$ | 2-thienyl | 180 | (Z)-22c | 85 | 2.2/97.8 |

TABLE 1-continued

Pd-Catalyzed Coupling of (E)- and (Z)-21 with Aryl Iodides[a]

$$\underset{21}{\overset{R^2}{\underset{R^1}{\diagup}}\!\!=\!\!\overset{}{\underset{}{\diagdown}}\!\!Si\!\!\underset{Me}{\diagup}} + Aryl \xrightarrow[\text{Bu}_4\text{N}^+\text{F (3 equiv.)}]{\text{Pd(dba)}_2 \text{ (5 mol \%)}} \underset{\text{THF/RT}}{\overset{R^2}{\underset{R^1}{\diagup}}\!\!=\!\!\overset{}{\underset{}{\diagdown}}\!\!Aryl}$$
22

| entry | silane | R¹ | R² | aryl | time, min | product | yield, %[b] | ratio, E/Z[c] |
|---|---|---|---|---|---|---|---|---|
| 7 | (E)-21 | n-C₅H₁₁ | H | 4-(CH₃CO)C₆H₄ | 10 | (E)-22d | 84 | 99.7/0.3 |
| 8 | (Z)-21 | H | n-C₅H₁₁ | 4-(CH₃CO)C₆H₄ | 10 | (Z)-22d | 88 | 2.0/98.0 |
| 9 | (E)-21 | n-C₅H₁₁ | H | 4-(CH₃O)C₆H₄ | 10 | (E)-22e | 94 | 99.0/1.0 |
| 10 | (Z)-21 | H | n-C₅H₁₁ | 4-(CH₃O)C₆H₄ | 10 | (Z)-22e | 90 | 2.5/97.5 |

[a]Reactions used 1.1 equiv of 21 unless otherwise noted.
[b]Yield of analytically pure materials.
[c]Determined by GC analysis.
[d]1.2 equiv of 21 used.

TABLE 2

Pd-Catalyzed Coupling of (E)- and (Z)-1 with Alkenyl Halides[a]

| entry | silane | R¹ | R² | R³ | R⁴ | X | time, min | product | yield, %[b] | ratios[c,d] | ratio, 4/5[d] |
|---|---|---|---|---|---|---|---|---|---|---|---|
| 1 | (E)-21 | n-C₅H₁₁ | H | C₆H₅ | H | I | 10 | (E,E)-24a | 73 | 98.0/2.0[f] | 96/4 |
| 2[e] | (E)-21 | n-C₅H₁₁ | H | C₆H₅ | H | Br | 60 | (E,E)-24a | 80 | 98.4/1.6[f] | 98/2 |
| 3 | (Z)-21 | H | n-C₅H₁₁ | C₆H₅ | H | I | 10 | (E,Z)-24a | 75 | 97.2/2.8[g] | 98/2 |
| 4 | (E)-21 | n-C₅H₁₁ | H | (CH₂)₄OH | H | I | 90 | (E,E)-24c | 95 | 98.4/1.6[f] | 90/10 |
| 5 | (Z)-21 | H | n-C₅H₁₁ | (CH₂)₄OH | H | I | 90 | (E,Z)-24c | 74 | 97.0/3.0[g] | 85/15 |
| 6 | (E)-21 | n-C₅H₁₁ | H | H | (CH₂)₄OH | I | 90 | (Z,E)-24c | 70 | 97.3/3.0[f] | 99/1 |
| 7[e] | (Z)-21 | H | n-C₅H₁₁ | H | (CH₂)₄OH | I | 300 | (Z,Z)-24c | 65 | 94.8/5.2[h] | 99/1 |

[a]Reactions employed 1.1 equiv of 21 and 5 mol % Pd(dba)₂ unless otherwise noted,
[b]Yield of analytically pure materials,
[c]Isomeric purity of major component,
[d]Determined by GC analysis,
[e]1.2 to 1.5 equiv of 1 and 2.5 mol % of [allylPdCl]₂ were used,
[f]Ratio (E,E)/(E,Z),
[g]Ratio (Z,E)/(ZZ) + (E,E).
[h]Ratio (Z,Z)/all other isomers.

TABLE 3

The Effect of Additive on the Coupling with 42 at Room Temperature

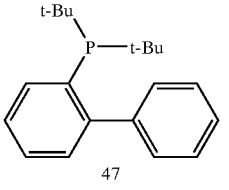

| entry | ligand | time (h) | conversion (%) | product ratio (4:5:6) |
|---|---|---|---|---|
| 1 | — | 68 | 100 | 71:15:13 |
| 2 | (o-tol)$_3$P | 46 | 0 | |
| 3 | (C$_6$F$_5$)$_3$P | 24 | 0 | |
| 4 | (furyl)$_3$P | 46 | 100 | 86:14:0 |
| 5 | Ph$_3$As | 96 | 100 | 93:7:0 |
| 6 | (t-Bu)$_3$P | 90 | 78 | 73:5:0 |
| 7 | (c-Hex)$_3$P | 72 | 100 | 91:9:0 |
| 8 | 47 | 48 | 100 | 75:25:0 |
| 9 | 48 | 24 | 16 | 8:8:0 |
| 10 | DMPE | 24 | 85 | 74:11:0 |

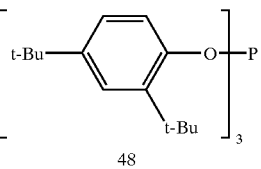

TABLE 4

The Effect of Additives for the Coupling with 42 at 50° C.

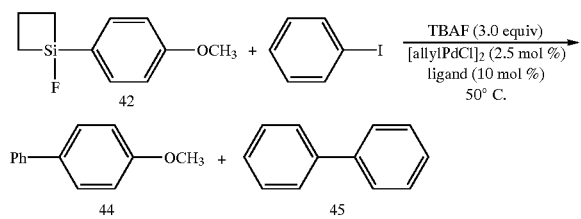

| entry | ligand | time (h) | comversion (%) | product ratio (4:5) |
|---|---|---|---|---|
| 1 | (o-tol)$_3$P | 22 | 100 | 88:12 |
| 2 | (C$_6$F$_5$)$_3$P | 24 | 0 | |
| 3 | DPPE | 22 | 100 | 87:13 |
| 4 | DPPF | 22 | 100 | 50:50 |

TABLE 4-continued

The Effect of Additives for the Coupling with 42 at 50° C.

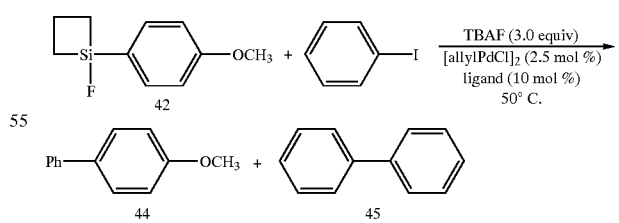

| entry | ligand | time (h) | comversion (%) | product ratio (4:5) |
|---|---|---|---|---|
| 5 | DMPE | 24 | 0 | |
| 6 | (c-Hex)$_3$P | 22 | 100 | 75:25 |
| 7 | (t-Bu)$_3$P | 22 | 100 | 94:6 |

TABLE 5

The Effect of Ligand/Pd Ratio on the Coupling with 42[a]

| entry | (t-Bu)₃P[b] | (t-Bu)₃P/Pd | conversion (%) | 4:5 |
|---|---|---|---|---|
| 1 | 6 | 1.2 | 100 | 7:1 |
| 2 | 10 | 2.0 | 100 | 12:1 |
| 3 | 21 | 4.2 | 57 | 56:1 |
| 4 | 36 | 7.2 | 35 | 1:0 |

[a]See Table 4 for reaction conditions.
[b]Mole % (t-Bu)₃P with respect to 42.

TABLE 6

The Effect of Ligand/Pd Ratio on the Coupling with 40.

| (t-Bu)₃P | (t-Bu)₃P/Pd | 4:5 |
|---|---|---|
| 11 mol % | 2.2 | 89:11 |
| 16 mol % | 3.2 | 92:8 |
| 20 mol % | 4.0 | 95:5 |

TABLE 7

Cross-Coupling of Selected Aryl Iodides with 40

(a) TBAF (3.0 equiv), [allylPdCl]₂ (2.5 mol %), (t-Bu)₃P (20 mol %), THF, reflux.

| entry | Aryl-I | time (h) | yield (%) |
|---|---|---|---|
| 1 | C₆H₅–I | 1 | 91 |
| 2 | EtO₂C–C₆H₄–I | 1 | 83 |
| 3 | H₃COC–C₆H₄–I | 1 | 73 |
| 4 | O₂N–C₆H₄–I | 1 | 75 |
| 5 | NC–C₆H₄–I | 1 | 81 |
| 6 | H₃C–C₆H₄–I | 1 | 92 |
| 7 | 1-naphthyl-I | 2 | 85 |
| 8 | 3-methylphenyl-I | 1 | 85 |
| 9 | 3-nitrophenyl-I | 1 | 90 |
| 10 | 2-methylphenyl-I | 3 | 89 |
| 11 | 2-nitrophenyl-I | 3 | 84 |
| 12 | 3-pyridyl-I | 5 | 71 |

TABLE 8

Cross-Coupling of Selected Aryl Iodides with Aryl Silane 49

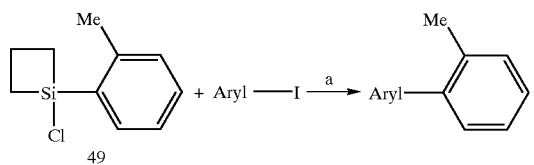

(a) TBAF (3.0 equiv), [allylPdCl]$_2$ (2.5 mol %), (t-Bu)$_3$P (20 mol %), THF, reflux.

| entry | Aryl-I | time (h) | yield (%) |
|---|---|---|---|
| 1 | O$_2$N-C$_6$H$_4$-I (4-) | 2 | 73 |
| 2 | 3-CH$_3$-C$_6$H$_4$-I | 8 | 76 |
| 3 | 2-NO$_2$-C$_6$H$_4$-I | 3 | 77 |
| 4 | 2-CH$_3$-C$_6$H$_4$-I | 12 | 85 |

TABLE 9

Palladium-Catalyzed Cross-Coupling of (E)-1 and (Z)-1 with Aryl Iodides.[a]

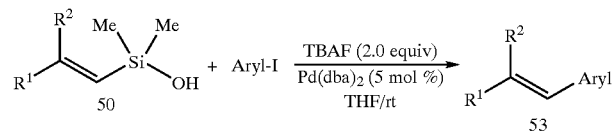

| entry | silane | R$^1$ | R$^2$ | Aryl | time, min | product | yield[b], % | ratio[c], E/Z |
|---|---|---|---|---|---|---|---|---|
| 1 | (E)-50 | n-C$_5$H$_{11}$ | H | C$_6$H$_5$ | 10 | (E)-53[a] | 91 | 97.8/2.2 |
| 2 | (Z)-50 | H | n-C$_5$H$_{11}$ | C$_6$H$_5$ | 10 | (Z)-53[a] | 90 | 2.7/97.3 |
| 3 | (E)-50 | n-C$_5$H$_{11}$ | H | 1-naphthyl | 30 | (E)-53[b] | 89 | 96.5/3.5 |
| 4 | (Z)-60 | H | n-C$_5$H$_{11}$ | 1-naphthyl | 30 | (Z)-53[b] | 85 | 3.3/96.7 |
| 5[d] | (E)-50 | n-C$_5$H$_{11}$ | H | 1-naphthyl | 30 | (E)-53[b] | 76 | 96.6/3.4 (2.5% cine) |
| 6[e] | (E)-50 | n-C$_5$H$_{11}$ | H | 2-thienyl | 180 | (E)-53[c] | 83 | 95.7/4.3 |
| 7[e] | (Z)-50 | H | n-C$_5$H$_{11}$ | 2-thienyl | 180 | (Z)-53[c] | 81 | 2.5/97.5 |
| 8 | (E)-50 | n-C$_5$H$_{11}$ | H | 4-(CH$_3$CO)C$_6$H$_4$ | 10 | (E)-53[d] | 93 | 96.5/3.5 |
| 9[f] | (E)-50 | n-C$_5$H$_{11}$ | H | 4-(CH$_3$CO)C$_6$H$_4$ | 60 | (E)-53[d] | 87 | 95.5/4.5 |
| 10[g] | (E)-50 | n-C$_5$H$_{11}$ | H | 4-(CH$_3$CO)C$_6$H$_4$ | 180 | (E)-53[d] | 74 | 96.9/3.1 |
| 11 | (Z)-50 | H | n-C$_5$H$_{11}$ | 4-(CH$_3$CO)C$_6$H$_4$ | 10 | (Z)-53[d] | 92 | 4.8/95.2 |
| 12 | (E)-50 | n-C$_5$H$_{11}$ | H | 4-(CH$_3$O)C$_6$H$_4$ | 10 | (E)-53[e] | 95 | 97.2/2.8 |
| 13 | (Z)-50 | H | n-C$_5$H$_{11}$ | 4-(CH$_3$O)C$_6$H$_4$ | 10 | (Z)-53[e] | 94 | 2.6/97.4 |

[a]All reactions employed 1.1 equiv of 1 unless otherwise noted.
[b]Yield of chromatographically homogeneous materials.
[c]Determined by GC analysis.
[d]2.0 equiv of tetrabutylammonium hydroxide (2.0 M solution in CH$_3$OH) was employed.
[e]1.2 equiv of 1 used.
[f]1.0 equiv of TBAF was used.
[g]1.2 equiv of 1 and 2.5 mol % of [allylPdCl]$_2$ were used with 4-bromoacetophenone, after 2 h, an additional equivalent of TBAF and 1.25 mol % of [allylPdCl]$_2$ were added.

TABLE 10

Palladium-Catalyzed Cross-Coupling of (E)-52 and (Z)-52 with Aryl Iodides.[a]

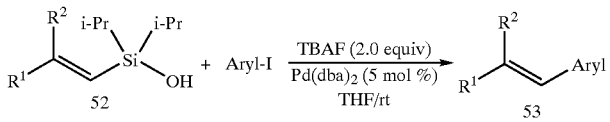

| entry | silane | $R^1$ | $R^2$ | Aryl | time, min | product | yield[b], % | ratio[c], E/Z |
|---|---|---|---|---|---|---|---|---|
| 1 | (E)-52 | n-$C_5H_{11}$ | H | $C_6H_5$ | 10 | (E)-53[a] | 82 | 99.2/0.8 |
| 2 | (Z)-52 | H | n-$C_5H_{11}$ | $C_6H_5$ | 10 | (Z)-53[a] | 81 | 0.6/99.4 |
| 3 | (E)-52 | n-$C_5H_{11}$ | H | 1-naphthyl | 30 | (E)-53[b] | 85 | 98.4/1.6 |
| 4 | (Z)-52 | H | n-$C_5H_{11}$ | 1-naphthyl | 30 | (Z)-53[b] | 79 | 2.3/97.7 |
| 5 | (E)-52[d] | n-$C_5H_{11}$ | H | 1-naphthyl | 30 | (E)-53[b] | 78 | 99.2/0.8 |
| 6 | (E)-52 | n-$C_5H_{11}$ | H | 4-($CH_3CO$)$C_6H_4$ | 10 | (E)-53[d] | 80 | >99.5/0.5 |
| 7 | (Z)-52 | H | n-$C_5H_{11}$ | 4-($CH_3CO$)$C_6H_4$ | 10 | (Z)-53[d] | 86 | 1.0/99.0 |

[a]All reactions employed 1.1 equiv of 52
[b]Yield of chromatographically homogeneous materials.
[c]Determined by GC analysis.
[d]2.0 equivalents of tetrabutylammonium hydroxide were used instead of TBAF.

TABLE 11

Palladium-Catalyzed Cross-Coupling of (E)-1 and (Z)-1 Alkenyl Iodides.[a]

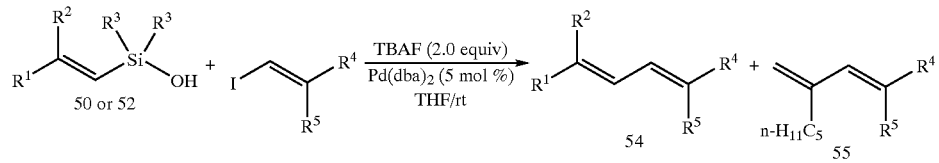

| entry | silane | $R^1$ | $R^2$ | $R^3$ | $R^4$ | $R^5$ | time, min | product | yield[b], % | ratios[c,d] | ratio[d] 4/5 |
|---|---|---|---|---|---|---|---|---|---|---|---|
| 1 | (E)-50 | n-$C_5H_{11}$ | H | Me | $(CH_2)_4OH$ | H | 90 | (E,E)-54 | 91 | 95.8/4.2[f] | 86/14 |
| 2 | (E)-52 | n-$C_5H_{11}$ | H | i-Pr | $(CH_2)_4OH$ | H | 90 | (E,E)-54 | 87 | 97.8/2.2 | 96/4 |
| 3 | (Z)-50 | H | n-$C_5H_{11}$ | Me | $(CH_2)_4OH$ | H | 90 | (E,Z)-54 | 72 | 95.4/4.6[g] | 91/9 |
| 4 | (E)-50 | n-$C_5H_{11}$ | H | Me | H | $(CH_2)_4OH$ | 90 | (Z,E)-54 | 73 | 5.9/94.1 | >99/1 |
| 5[e] | (Z)-50 | H | n-$C_5H_{11}$ | Me | H | $(CH_2)_4OH$ | 300 | (Z,Z)-54 | 64 | 12.2/87.8[h] | >99/1 |
| 6[e] | (Z)-52 | H | n-$C_5H_{11}$ | i-Pr | H | $(CH_2)_4OH$ | 300 | (Z,Z)-54 | 68 | 7.6/92.4[h] | 93.2/6.8 |

[a]All reactions employed 1.1 equiv of 50 and 5 mol % Pd(dba)$_2$ unless otherwise noted.
[b]Yield of chromatographically pure materials.
[c]Isomeric purity of major component.
[d]Determined by GC analysis.
[e]1.5 equiv of 50 and 2.5 mol % of [allylPdCl]$_2$ were used.
[f]Ratio (E,E)/(E,Z).
[g]Ratio (Z,E)/(Z,Z) + (E,E).
[h]Ratio (Z,Z)/all other isomers.

TABLE 12

Palladium-Catalyzed Cross-Coupling of 61 with Aryl Iodides[a]

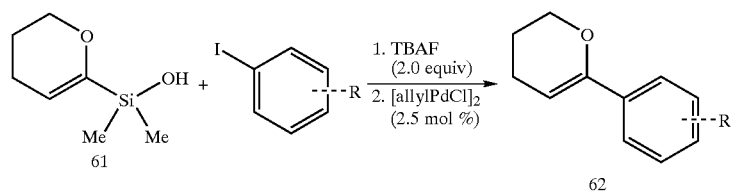

| entry | R | time, min | product | yield,[b] % |
|---|---|---|---|---|
| 1 | 4-$CO_2Et$ | 10 | 62a | 84 |
| 2 | 3-$CO_2Et$ | 10 | 62b | 86 |
| 3 | 2-$CO_2Me$ | 240 | 62c | 92 |
| 4 | 2-$NO_2$ | 10 | 62d | 85 |

TABLE 12-continued

Palladium-Catalyzed Cross-Coupling of 61 with Aryl Iodides[a]

| entry | R | time, min | product | yield,[b] % |
|---|---|---|---|---|
| 5[c,d] | 2-CH$_3$ | 20 | 62e | 80 |
| 6 | 2-OCH$_3$ | 10 | 62f | 74 |
| 7[c,d] | 2-CH$_2$OH | 20 | 62g | 88 |
| 8 | 3-CH$_2$OAc | 20 | 62h | 87 |

[a] All reactions employed 1.2 equiv of 61
[b] Yield of analytically pure materials.
[c] Yield of chromatographically homogeneous materials.
[d] 1.2 equiv of 61 and 5 mol % of Pd(dba)$_2$ were used.

TABLE 13

Palladium-Catalyzed Cross-Coupling of 74 with Aryl Iodides[a]

| entry | R | Pd(dba)$_2$, mol % | time, min | product | yield,[b] % |
|---|---|---|---|---|---|
| 1[c] | 4-COMe | 5.0 | 10 | 75a | 90 |
| 2 | 4-OMe | 3.0 | 30 | 75b | 92 |
| 3 | 3-CO$_2$Et | 3.0 | 30 | 75c | 93 |
| 4 | 2-Me | 3.0 | 30 | 75d | 89 |
| 5 | 2-NO$_2$ | 3.0 | 90 | 75e | 86 |
| 6 | 2-CH$_2$OH | 5.0 | 180 | 75f | 90 |
| 7 | 2-CO$_2$Me | 5.0 | 360 | 75g | 84 |

[a] All reactions employed 4 (1.1 equiv), TBAF (2.0 equiv), aryl iodide (1.0 equiv), and Pd(dba)$_2$ (3.0–5.0 mol %) in THF at room temperature.
[b] Yields of analytically pure materials.
[c] Yield of chromatographically homogeneous material.

TABLE 14

Palladium-Catalyzed Cross-Coupling of 76 with Aryl Iodides[a]

| entry | substrate, n | $R^1$ | $R^2$ | $R^3$ | Pd(dba)$_2$, mol % | time, h | product | yield,[b] % |
|---|---|---|---|---|---|---|---|---|
| 1 | 76a, 0 | H | H | 4-CO$_2$Et | 3.0 | 0.5 | 77a | 85 |
| 2 | 76b, 1 | H | Me | 2-Me | 3.0 | 0.75 | 77b | 83 |
| 3[c] | 76c, 1 | C$_6$H$_{13}$ | H | 3-CO$_2$Et | 10.0 | 24 | 77c | 81 |
| 4 | 76d, 2 | H | H | 4-OMe | 3.0 | 0.5 | 77d | 85[d] |

[a]All reactions employed 76 (1.1 equiv), TBAF (2.0 equiv), aryl iodide (1.0 equiv), and Pd(dba)$_2$ (3.0 mol %) at room temperature unless otherwise specified.
[b]Yields of analytically pure materials.
[c]Pd(dba)$_2$ (2.5 mol %/3 h) and 0.25 mmol/3 h) were added portionwise.
[d]Yield of chromatographically homogeneous material.

TABLE 15

Palladium-Catalyzed Cross-Coupling of 78 with Aryl Iodides(a)

| entry | R | time, h/temperature, °C | product | yield,[b] % |
|---|---|---|---|---|
| 1 | H | 6.66/rt | 79a | 88 |
| 2 | 2-Me | 6.83/rt | 79b | 74 |
| 3 | 2-MeO | 10.0/35 | 79c | 74 |
| 4 | 2-NO$_2$ | 23/35 | 79d | 56 |
| 5 | 3-HOCH$_2$ | 6.0/rt | 79e | 81 |
| 6 | 4-CH$_{3O}$ | 6.50/rt | 79f | 72 |
| 7 | 4-MeCO | 6.0/rt | 79g | 70 |
| 8 | 4-NO$_2$ | 6.25/rt | 79h | 67[c] |
| 9 | 4-CN | 46/45 | 79i | 70 |
| 10 | 4-COOEt | 16/45 | 79j | 86 |

[a]Reaction conditions: 1.1 equiv of 78 2.0 equiv of TBAF, and 5 mol % of Pd(dba)$_2$ were employed for 1.0 equiv of iodide in THF at rt. The iodide was added in portions as specified (see Supporting Information).
[b]Yields of analytically pure materials.
[c]Isomeric ratio 95.2/4.8 by capillary GC analysis.

TABLE 16

Palladium-Catalyzed Cross-Coupling of Silyl Hydrides with Aryl Iodides[a]

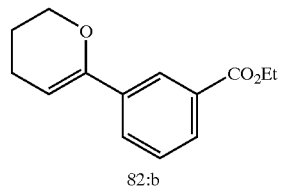

| entry | silane | $R^3$ | time, min | product | yield %[b] |
|---|---|---|---|---|---|
| 1[c] | 84 | 3-CO$_2$Et | 10 | 82:b | 81 |

TABLE 16-continued

Palladium-Catalyzed Cross-Coupling of Silyl Hydrides with Aryl Iodides[a]

| entry | silane | $R^3$ | time, min | product | yield %[b] |
|---|---|---|---|---|---|
| 2[c,d] | 85 | 4-CO$_2$Et | 10 | 87 | 89 |
| 3[d] | 85 | 2-Me | 30 | 88 | 83 |
| 4[c,d,e] | 85 | 4-OMe | 10 | 89 | 94 |
| 5[d,f] | 85 | 2-CN | 900 | 90 | 76 |
| 6[g] | 86 | 4-MeCO | 10 | 91 | 71 |

[a]1.2 equiv of silyl hydride, 2.0 equiv of TBAF, and 2.5 mol % of [allylPdCl]$_2$ were used unless otherwise specified.
[b]Yield of analytically pure materials.
[c]Yield of chromatographically homogeneous materials.
[d]1.4 equiv of 85 and 2.5 mol % of [allylPdCl]$_2$ were used.
[e]The intermediate enol ether was hydrolyzed directly (1 N HCl).
[f]2-Bromobenzonitrile was used.
[g]3.0 equiv of TBAOH was used.

TABLE 17

Optimization of the coupling of vinylpolysioxanes with 96

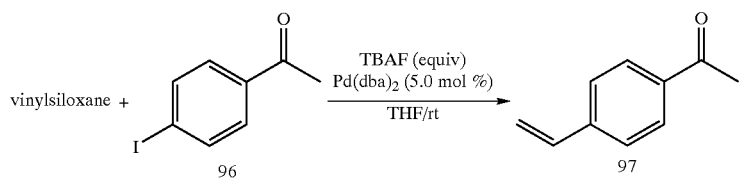

| Entry | Vinylsiloxane (equivalents) | TBAF (equivalents) | Time (min) | Conversion (%) |
|---|---|---|---|---|
| 1 | 92 (1.2/4) | 2.0 | 10 | 100 (88) |
| 2 | 93 (1.2/3) | 2.0 | 10 | 100 (85) |
| 3 | 94 (1.2/3) | 2.0 | 10 | 100 (89) |
| 4 | 95 (1.2/6) | 2.0 | 10 | 78 |
| 5 | 95 (1.5/6) | 2.0 | 10 | 94 (51) |
| 6 | 95 (1.5/6) | 2.0 | 10 | 93 (53) |

*The numbers in parentheses are isolated yields from 2.0 mmol scale experiments.

TABLE 18

Cross-coupling of 92 ($D_4^V$) with aryl iodides[a]

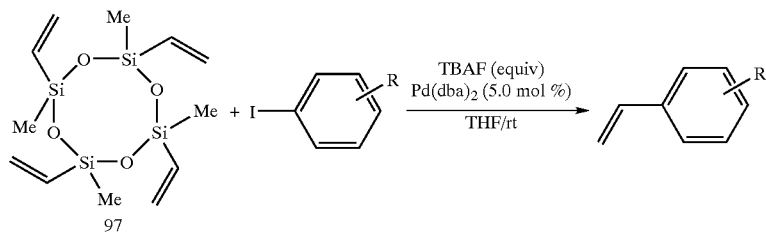

| Entry | Aryl, R | 92 (equivalents) | TBAF (equivalents) | Time (min) | Product | Yield (%) |
|---|---|---|---|---|---|---|
| 1 | 1-COMe$_{93}$ | 1.2 | 1 | 2.0 | 10 | 97 | 8.8 |
| 2[b] | 1-COMe$_{96}$ | 1.2 | 4 | 2.0 | 10 | 97 | 8.0 |
| 3 | 1-COOEt$_{98}$ | 1.2 | 4 | 2.0 | 10 | 99 | 8.5 |
| 4[c] | 4-COOEt$_{98}$ | 1.2 | 4 | 2.0 | 60 | 99 | 8.3 |
| 5 | 1-COMe$_{100}$ | 1.5 | 4 | 3.0 | 240 | 101 | 46 |
| 6[d] | 1-COMe$_{100}$ | 1.5 | 4 | 3.0 | 360 | 101 | 63 |
| 7 | 3-NO$_2$102 | 1.2 | 4 | 2.0 | 10 | 103 | 87 |
| 8[a] | 3-CH$_2$OH$_{104}$ | 1.2 | 4 | 2.0 | 480 | 105 | 59 |
| 9[d] | 2-OMe$_{106}$ | 1.5 | 4 | 3.0 | 24 h | 107 | 72 |
| 10[d] | 2-COOMe$_{108}$ | 1.2 | 4 | 2.0 | 480 | 109 | 83 |
| 11 | 1-naphthyl-1$_{110}$ | 1.2 | 4 | 2.0 | 180 | 111 | 64 |

[a]All the reactions were conducted under argon on 2.0 mmol scale.
[b]4-Iodoacetophenone added last over 45 min at <30° C.
[c]1 mol % Pd(dba), loading.
[d]10 mol %, AsPh, added.

TABLE 19

| Iodide | Step | Product | Yield |
|---|---|---|---|
| 4-iodoanisole | 1 | (E)-4,4'-dimethoxystilbene | 0.411 mmol (82.2%) |
| 4'-iodoacetophenone | 2 | (E)-4,4'-diacetylstilbene | 0.144 mmol (57.5%) |
| ethyl 4-iodobenzoate | 3 | diethyl (E)-stilbene-4,4'-dicarboxylate | 0.236 mmol (94.3%) |
| 4-iodobenzonitrile | 2 | (E)-4,4'-dicyanostilbene | 0.181 mmol (72.3%) |
| ethyl 3-iodobenzoate | 2 | diethyl (E)-stilbene-3,3'-dicarboxylate | 0.207 mmol (83.0%) |
| 2-iodotoluene | 2 | (E)-2,2'-dimethylstilbene | 0.195 mmol (78.1%) |
| methyl 2-iodobenzoate | 2 | dimethyl (E)-stilbene-2,2'-dicarboxylate | 0.159 mmol (63.4%) |

TABLE 19-continued

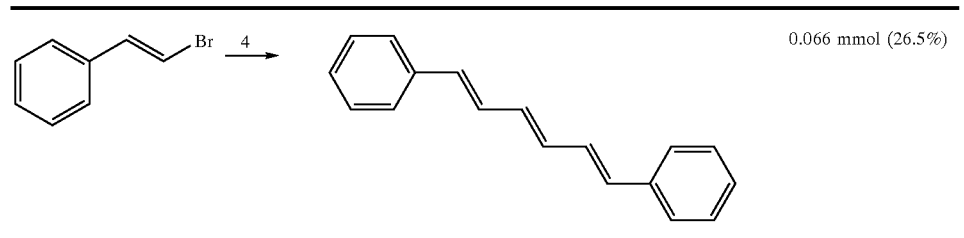

0.066 mmol (26.5%)

1: 0.6 mmol 1,2-bis(dimethylethoxysilyl)ethene; 2 ml TBAF (1 M in THF); 1.0 mmol ArI; 28.8 mg Pd(dba)$_2$
2: 0.3 mmol 1,2-bis(dimethylethoxysilyl)ethene; 1 ml TBAF (1 M in THF); 0.5 mmol ArI; 14.4 mg Pd(dba)$_2$
3: 0.25 mmol 1,2-bis(dimethylethoxysilyl)ethene; 1 ml TBAF (1 M in THF); 0.5 mmol ArI; 14.4 mg Pd(dba)$_2$
4: 0.3 mmol 1,2-bis(dimethylethoxysilyl)ethene; 1 ml TBAF (1 M in THF); 0.5 mmol bromostyrene; 4.57 mg (allylPdCl)$_2$

TABLE 20

Palladium Catalyzed Coupling of (E)-21 with 1-Iodonaphthalene

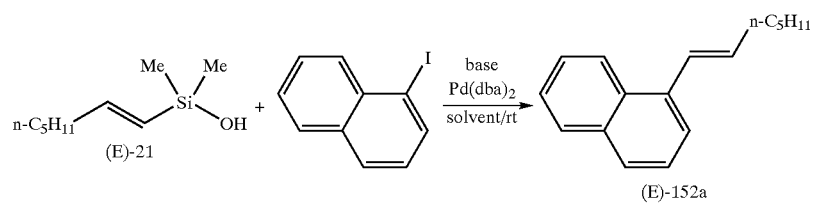

| entry | base   | solvent | time, min | yield, %[b] | E/Z-152a  |
|-------|--------|---------|-----------|-------------|-----------|
| 1     | MeLi   | THF     | 1440      | —[c,d]      |           |
| 2     | NaH    | THF     | 480       | 85          | 99.7/0.3  |
| 3     | NaH    | DMF     | 90        | 78          | 99.5/0.5  |
| 4     | NaH    | DME     | 60        | 81          | 99.5/0.5  |
| 5     | KH     | THF     | 120       | 85          | 99.7/0.3  |
| 6     | KH     | DME     | 15        | 82          | 99.6/0.4  |
| 7     | KOt-Bu | DME     | 180       | 90          | 99.4/0.6  |

[a]All reactions performed with 2.0 equiv of base and 5 mol % Pd(dba)$_2$.
[b]Yields of chromatographically homogeneous material.
[c]47% recovery of 1-iodonaphthalene.
[d]40% yield of 1-methylnaphthalene.

TABLE 21

Palladium Catalyzed Coupling of (Z)-21 with 1-Iodonaphthalene.[a]

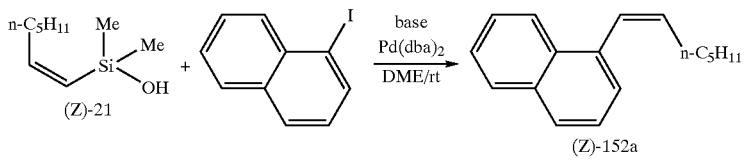

| entry | base    | equiv  | time, h | yield, %  | Z/E-152a  |
|-------|---------|--------|---------|-----------|-----------|
| 1     | KH      | 2.0    | 0.25    | 48[b]     | 98.3/1.7  |
| 2     | KOt-Bu  | 2.0    | 24      | 53[c]     | 85.5/14.5 |
| 3     | KOSiMe$_3$ | 2.0 | 8       | 88        | 98.0/2.0  |
| 4     | KOSiMe$_3$ | 3.0 | 8       | 73[d]     | —         |
| 5     | KOSiMe$_3$ | 1.0 | 18      | 74[d]     | —         |
| 6     | KOSiMe$_3$ | 2.0[e] | 8    | 85[d]     | —         |

[a]All reactions employed 5 mol % Pd(dba)$_2$.
[b]30% of naphthalene isolated.
[c]65% conversion of 1-iodonaphthalene.
[d]conversion, %.
[e]0.25 equiv of (Me$_3$Si)$_2$O added.

TABLE 22

Palladium catalyzed Coupling of (E) and (Z)-21 with Aryl Iodides.[a]

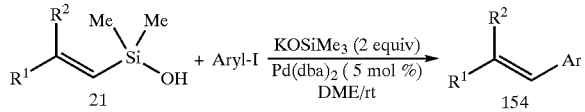

| entry | silane21 | R[1] | R[2] | aryl | time, h | product 154 | yield, % | ratio, E/Z[b] |
|---|---|---|---|---|---|---|---|---|
| 1 | (E) | n-C$_5$H$_{11}$ | H | 1-naphthyl | 2 | (E) a | 93[c] | 97.9/2.1 |
| 2 | (Z) | H | n-C$_5$H$_{11}$ | 1-naphthyl | 9 | (Z) a | 88[c] | 2.8/97.2 |
| 3 | (E) | n-C$_5$H$_{11}$ | H | phenyl | 0.5 | (E) b | 91[c] | 99.3/0.7 |
| 4 | (Z) | H | n-C$_5$H$_{11}$ | phenyl | 7.5 | (Z) b | 86[d] | 1.8/98.2 |
| 5 | (E) | n-C$_5$H$_{11}$ | H | 4-(CH$_3$CO)C$_6$H$_4$ | 9 | (E) c | 82[d] | 98.8/1.2 |
| 6 | (Z) | H | n-C$_5$H$_{11}$ | 4-(CH$_3$CO)C$_6$H$_4$ | 13 | (Z) c | 83[d] | 2.9/97.1 |
| 7 | (E) | n-C$_5$H$_{11}$ | H | 4-CH$_3$O)C$_6$H$_4$ | 1 | (E) d | 88[e] | 99.3/0.7[d] |
| 8 | (Z) | H | n-C$_5$H$_{11}$ | 4-(CH$_3$O)C$_6$H$_4$ | 9.5 | (Z) d | 91[e] | 1.1/98.9[e] |
| 9 | (E) | n-C$_5$H$_{11}$ | H | 4-(NO$_2$)C$_6$H$_4$ | 0.25 | (E) e | 95[f] | 98.5/1.5 |
| 10 | (Z) | H | n-C$_5$H$_{11}$ | 4-(NO$_2$)C$_6$H$_4$ | 0.25 | (Z) e | 85[f] | 3.8/96.2 |
| 11 | (E) | n-C$_5$H$_{11}$ | H | 4-(EtO$_2$C)C$_6$H$_4$ | 0.25 | (E) f | 85[f] | 99.8/0.2 |
| 12 | (Z) | H | n-C$_5$H$_{11}$ | 4-(EtO$_2$C)C$_6$H$_4$ | 0.25 | (Z) f | 83[f] | 0.7/99.3 |
| 13 | (E) | n-C$_5$H$_{11}$ | H | 2-(TBSOCH$_3$)C$_6$H$_4$ | 9 | (E) g | 80[f] | 99.5/0.5 |
| 14 | (Z) | H | n-C$_5$H$_{11}$ | 2-(TBSOCH$_3$)C$_6$H$_4$ | 14.5 | (Z) g | 76[f] | 2.0/98.0[g] |

[a]Reactions employed 1.1 equiv of 21
[b]Determined by GC analysis.
[c]yield of chromatographed, distilled products.
[d]Accompanied by 3.8% cine-rearranged product.
[e]Accompanied by 6.2% cine-rearranged product.
[f]yield of analytically pure material.
[g]at 50° C.

TABLE 23

One-Pot Hydrosilylation/Cross-Coupling of 1-Heptyne with Aryl and Alkenyl Iodides[a]

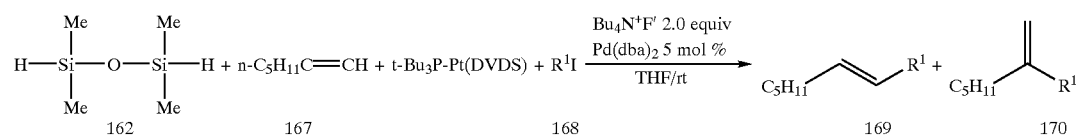

| entry | halide, R[1](168) | time, min | product 169 | yield,[b] % | ratio (E)-169/(Z)-169/170[c] |
|---|---|---|---|---|---|
| 1 | 1-naphthyl (a) | 10 | a | 82 | 98.4/0.1/1.5 |
| 2 | 4-(CH$_3$CO)C$_6$H$_4$ (b) | 10 | b | 94 | 99.1/0.4/0.5 |
| 3 | 4-(CH$_3$O)C$_6$H$_4$ (c) | 10 | c | 84 | 96.5/1.4/2.1 |
| 4[d] | 4-(CH$_3$O)C$_6$H$_4$ (c) | 10 | c | 89 | 97.7/1.0/1.3 |
| 5 | 3-(NO$_2$)C$_6$H$_4$ (d) | 10 | d | 85 | 97.5/2.5[e] |
| 6[f] | 3-(NO$_2$)C$_6$H$_4$ (d) | 60 | d | 89 | 98.5/1.5[e] |
| 7 | 3-(CH$_3$)C$_6$H$_4$ (e) | 10 | e | 78 | 97.4/2.6[e] |
| 8[g] | 2-(CH$_3$OCO)C$_6$H$_4$ (f) | 20 h | f | 88 | 96.7/2.3[e] |
| 9 | 2-(CH$_3$O)C$_6$H$_4$ (g) | 10 | g | 82 | 99.4/0.6[e] |
| 10 | (E)-ICH=CHC$_5$H$_{11}$ (h) | 16 h | h | 67 | 91.4/8.6[h] |
| 11[i] | (E)-BrCH=CHC$_6$H$_5$ (i) | 14 h | i | 70 | 92.0/3.2/4.8 |

[a]All reactions used 1.3/2 equiv of 162 and 1.3 equiv of 167 except entry 3 which used 1.56/2 eqiv of 162 1.3 equiv of 167 hydrosilylation required 30 min at rt.
[b]Yield of analytically pure materials.
[c]Determined by GC or GC-MS anaylsis.
[d]Iodide added last.
[e]Ratio (E)-169/((Z)-169) + 1/0f.
[f]1.0 mol % of Pd(dba)$_2$.
[g]10 mol % of Ph$_3$As was used.
[h]Ratio (E.E)-169/((E.Z)-169h 170
[i]2.5 mol % of [allylPdCl]$_2$ was used.

TABLE 24

One-Pot Hydrosilylation/Cross-Coupling of 1-Alkynes with Aryl Iodidies[a]

$$H-Si(Me)_2-O-Si(Me)_2-H + R^2-C\equiv CH + t\text{-}Bu_3P\text{-}Pt(DVDS) + R^1I \xrightarrow[\text{THF/rt}]{Bu_4N^+F^-\ 2.0\ \text{equiv},\ Pd(dba)_2\ 5\ \text{mol \%}} R^2\text{-CH=CH-}R^1 + R^2\text{-C(=CH}_2\text{)-}R^1$$

162 + 171–174 + 168 → 175–178 + 178–182

| entry | alkyne, $R^2$ | 168, $R^1$ | ratio (2/alkyne), equiv | time, min | product | yield,[b] % | ratio[c] |
|---|---|---|---|---|---|---|---|
| 1 | $C_6H_5$(171) | b | 0.72/1.5 | 10 | 175b | 89 | ≧99% |
| 2 | $C_6H_5$(171) | c | 0.72/1.5 | 10 | 175c | 74 | ≧99% |
| 3 | $HO(CH_2)_3$(172) | b | 0.9/1.8 | 30 | 176b | 82 | ≧99% |
| 4 | $HO(CH_2)_3$(172) | c | 0.9/1.8 | 60 | 176c | 89 | ≧99% |
| 5 | $C_6H_5C(OH)(CH_3)$(173) | b | 0.65/1.3 | 24 h | 177b | 72 | ≧98%[d] |
| 6 | $C_6H_5C(OH)(CH_3)$(173) | c | 0.65/1.3 | 24 h | 177c | 79 | ≧98%[d] |
| 7 | $CH_2=CHCH_2O(CH_2)_3$(174) | b | 0.98/1.5 | 10 | 178b | 78 | ≧99% |
| 8 | $CH_2=CHCH_2O(CH_2)_3$(174) | c | 0.98/1.5 | 10 | 178c | 76 | 99.6/0.4 |

[a] Procedure I was employed in entries 1–6; procedure II was employed in entries 7–8.
[b] Yield of analytically pure materials.
[c] Ratio of (E)-175-(E)-178/((Z)-175-(Z)-178 + (179–182)) was determined by GC-MS.
[d] ratio was determined by $^1H$ NMR.

TABLE 25

Molybdenum-Catalyzed Ring-Closing Metathesis of '207[a]

207 → (202 Schrock catalyst i, benzene, rt) → 208

| entry | substrate, 207 n | $R^1$ | $R^2$ | catalyst, mol % | time, h | 208 product | yield,[b] % |
|---|---|---|---|---|---|---|---|
| 1 | a, 0 | H | H | 7.0 | 3 | a | 89 |
| 2 | b, 1 | H | Me | 8.0 | 15 | b | 91 |
| 3 | c, 1 | $C_6H_{13}$ | H | 7.0 | 12 | c | 90 |
| 4 | d, 1 | $C_6H_{13}$ | Me | | | | |
| 5[c] | e, 2 | H | H | 7.0 | 12 | d | 81 |

[a] Reactions were performed at 0.1 M concentration.
[b] Yields of analytically pure materials.
[c] 91% conversion was observed by $^1H$ NMR analysis.

TABLE 26

One-Pot Arylation of Homopropargylic Alcohols

211 → (1. TMDS, 2. Pt(DVDS), 3. a. Aryl-i, b. TBAF, c. Pd(dba)$_2$) → 213 or 214

| entry | R | R' | Pd. % | time, min/ cmp. °C. | product | yield,[c] % (isomeric ratio) |
|---|---|---|---|---|---|---|
| 1[a] | Me | H | 10 | 40/rt | 213a | 85 (97.2/2.8) |
| 2[a] | Me | 2-OMe | 10 | 480/35 | 213c | 75 (98.3/1.7) |
| 3[a] | Me | 4-CN | 10 | 300/rt | 213i | 74 (96.7/3.3) |

TABLE 26-continued

One-Pot Arylation of Homopropargylic Alcohols

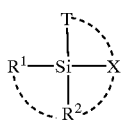

R—≡—/\—OH
1. TMDS
2. Pt(DVDS)
3. a. Aryl-i
   b. TBAF
   c. Pd(dba)₂
→ 213 or 214

211

| entry | R | R' | Pd. % | time, min/ cmp. °C. | product | yield,[c] % (isomeric ratio) |
|---|---|---|---|---|---|---|
| 4[b] | n-Bu | H | 10 | 40/rt | 214 | 84 (97.7/2.3) |
| 5[b] | n-Bu | H | 5 | 90/rt | 214 | 85 (98.3/1.7) |

[a]Reaction conditions: (1) homopropargylic alcohols (1.3 equiv.), TMDS (1.0–1.2 equiv), (2) 0.30–0.37% Pt(DVDS) in THF (1.5 mL/mmol alcohol). (3) TBAF (2.2 equiv), aryl iodide (1.0 equiv).
[b]Reaction conditions: (1) homopropargylic alcohol (1.3 equiv), TMDS (1.0 equiv); (2) remove TMDS in vacuo, (3) 0.30–0.37% Pt(DVDS) in THF (1.5 mL/mmol alcohol), (4) TBAF (2.2 equiv), aryl iodide (1.0 equiv).
[c]Yields of analytically pure materials.

We claim:

1. A method for generating a carbon-carbon bond between a transferable group and an acceptor group which comprises the steps of:
   a. reacting a organosilicon reagent of the formula:

$R^1-\underset{\underset{R^2}{|}}{\overset{\overset{T}{|}}{Si}}-X$ where T is the transferable group that can be selected from an aromatic group, a substituted aromatic group, a heteroaromatic group, an olefinic group, a substituted olefinic group, an allylic group, a substituted allylic group, an acetylenic group, a substituted acetylenic group, an allenic group, a substituted allenic group, an alkyl group, and a substituted alkyl group;
   X is selected from the group consisting of a hydrogen, an alkyl group, a substituted alkyl group, an olefinic group, a substituted olefinic group, an acetylenic group, a substituted acetylenic group, an aromatic group, a substituted aromatic group, a heteroaromatic group, a halide, OR or N(R)₂ groups, where R is hydrogen, an alkyl group or a substituted alkyl group, and a silane or siloxane group; and
   $R^1$ and $R^2$ are, independently, selected from the group consisting of alkyl or substituted alkyl groups, a silane group or a siloxane group; and where dashed lines indicate that any two of $R^1$, $R^2$, T or X can be covalently linked and $R^1$ and $R^2$ can be a transferable group T;
   with an organic electrophile $R^3Y$ in the presence of a basic and nucleophilic activator anion and a Group 10 metal catalyst; and
   b. recovering the desired cross-coupling product T-$R^3$ in which the —C—C— bond is formed.

2. The method of claim 1 wherein the activator anion is present at a level in molar equivalents in excess of the organosilicon reagent.

3. The method of claim 1 wherein the activator anion is present in an amount in molar equivalents ranging from about 2 to 3 times that of the organosilicon nucleophile.

4. The method of claim 1 wherein the activator anion is hydride.

5. The method of claim 1 wherein the activator anion is a trialkyl silanolate.

6. The method of claim 1 wherein the activator anion is trimethyl silanolate.

7. The method of claim 1 wherein the activator anion is fluoride-free.

8. The method of claim 1 wherein the activator is a tetraalkylammonium fluoride, tetraalkylammonium hydroxide, or a tetraalkylammonium alkoxide.

9. The method of claim 1 wherein the activator is a tetrabutylammonium fluoride, tetrabutylammonium hydroxide, or a tetrabutylammonium alkoxide.

10. The method of claim 1 further comprising the step of combining the organosilicon reagent with the activator anion to activate the organosilicon reagent before it is reacted with the organic electrophile.

11. The method of claim 1 wherein the Group 10 metal catalyst is a palladium catalyst.

12. The method of claim 1 wherein the palladium catalyst is selected from the group consisting of Pd(dba)₂; Pd(dba)₃; [Pd(allyl)Cl]₂; PdCl₂; Pd(OAc)₂; Pd(OTFA)₂; (COD)PdBr₂; Pd(OTf)₂; and (PhCN)₂PdCl₂.

13. The method of claim 1 wherein the palladium catalyst is Pd(dba)₂ or [Pd(allyl)Cl]₂.

14. The method of claim 1 wherein the reaction is carried out in a polar aprotic solvent.

15. The method of claim 1 wherein the reaction is carried out in a solvent selected from an ether, DMF, THF, CH₃CN, TBME and mixtures thereof.

16. The method of claim 1 wherein the method is carried out in DMF or DME.

17. The method of claim 1 wherein the reaction is carried out at ambient temperature.

18. The method of claim 1 wherein the organosilicon reagent is an aromatic or alkenylsilanol.

19. The method of claim 18 wherein T is selected from the group consisting of an olefinic group, a substituted olefinic group, an aromatic group, a substituted aromatic group, an allylic group, a substituted allylic group, an acetylenic group, a substituted acetylenic group, an allenic group, a substituted allenic group, an alkyl group, and a substituted alkyl group.

20. The method of claim 18 wherein T is selected from the group consisting of an olefinic group, a substituted olefinic group, an aromatic group, a substituted aromatic group, an allylic group, a substituted allylic group, an acetylenic group, a substituted acetylenic group, an allenic group, and a substituted allenic group.

21. The method of claim 18 wherein T is an olefinic group, or a substituted olefinic group.

22. The method of claim 1 wherein the organosilicon reagent is an alkenyl silanol.

23. The method of claim 22 wherein T is selected from the group consisting of an olefinic group, a substituted olefinic group, an aromatic group, a substituted aromatic group, an allylic group, a substituted allylic group, an acetylenic group, a substituted acetylenic group, an allenic group, a substituted allenic group, an alkyl group, and a substituted alkyl group.

24. The method of claim 22 wherein T is selected from the group consisting of an olefinic group, a substituted olefinic group, an aromatic group, a substituted aromatic group, an allylic group, a substituted allylic group, an acetylenic group, a substituted acetylenic group, an allenic group, and a substituted allenic group.

25. The method of claim 22 wherein T is an olefinic group, or a substituted olefinic group.

26. The method of claim 1 wherein in the organic electrophile, $R^3Y$, Y is a leaving group and $R^3$ is the acceptor group which is selected from the group consisting of an aromatic group, a substituted aromatic group, a heteroaromatic group, an olefinic group, a substituted olefinic group, an allylic group, a substituted allylic group, an acetylenic group, a substituted acetylenic group, an allenic group, a substituted allenic group, an alkyl group, and a substituted alkyl group.

27. The method of claim 1 wherein in the organic electrophile, $R^3Y$, Y is a leaving group and $R^3$ is the acceptor group which is selected from the group consisting of an aromatic group, a substituted aromatic group, an olefinic group, a substituted olefinic group, an allylic group, a substituted allylic group, an acetylenic group, a substituted acetylenic group, an allenic group, and a substituted allenic group.

28. The method of claim 1 wherein in the organic electrophile, $R^3Y$, Y is a leaving group and $R^3$ is the acceptor group which is selected from the group consisting of an aromatic group, a substituted aromatic group, an olefinic group, and a substituted olefinic group.

29. The method of claim 1 wherein in the organic electrophile, $R^3Y$, Y is a leaving group and $R^3$ is the acceptor group is an aromatic group, a heteroaromatic group, or a substituted aromatic group.

30. The method of claim 29 wherein T is an aromatic group or a substituted aromatic group.

31. The method of claim 29 wherein T is an olefinic group or a substituted olefinic group.

32. The method of claim 1 wherein in the organic electrophile, $R^3Y$, Y is a leaving group and $R^3$ is the acceptor group is an aromatic group, a heteroaromatic group or a substituted aromatic group.

33. The method of claim 29 wherein T is an aromatic group or a substituted aromatic group.

34. The method of claim 29 wherein T is an olefinic group or a substituted olefinic group.

35. The method of claim 1 wherein the organosilicon reagent has the formula:

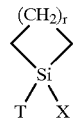

where X is, a hydrogen, a halide, an alkyl group, a substituted alkyl group, or an OR group, where R is a hydrogen, an alkyl group or a substituted alkyl group.

36. The method 35 wherein X is OR.

37. The method of claim 36 wherein X is OH.

38. The method of claim 35 wherein T is an alkenyl group or a substituted alkenyl group.

39. The method of claim 35 wherein T is an aromatic group, a substituted aromatic group or a heteroaromatic group.

40. The method of claim 35 wherein r is 1.

41. The method of claim 40 wherein X is OH.

42. The method of claim 41 wherein T is selected from the group consisting of an olefinic group, a substituted olefinic group, an aromatic group, a substituted aromatic group and a heteroaromatic group.

43. The method of claim 1 wherein the organosilicon reagent has the formula:

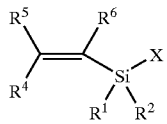

where X is a hydrogen or an OH or an OR group;
$R^1$ and $R^2$ are independently selected from the group consisting of alkyl or substituted alkyl groups wherein $R^1$ and $R^2$ may be covalently linked to each other; and
$R^{4-6}$ are independently selected from H, alkyl, substituted alkyl, alkoxy, aryl or substituted aryl groups wherein any two of $R^1$, $R^2$, $R^4$, $R^5$, or $R^6$ may be covalently linked.

44. The method of claim 43 wherein X is OH.

45. The method of claim 44 wherein $R^{4-6}$ are independently selected from the group consisting of H, alkyl, and substituted alkyl wherein any two of $R^1$, $R^2$, $R^4$, $R^5$, or $R^6$ maybe covalently linked.

46. The method of claim 1 wherein the organonucleophile has the formula:

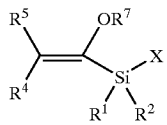

where X is a hydrogen or an OH or an OR group;
$R^1$ and $R^2$ are independently selected from the group consisting of alkyl or substituted alkyl groups wherein $R^1$ and $R^2$ may be covalently linked to each other; and
$R^{4-5}$ and $R^7$ independently selected from H, alkyl, substituted alkyl, alkoxy, aryl or substituted aryl groups wherein any two of $R^1$, $R^2$, $R^4$, $R^5$, or $R^7$ may be covalently linked.

47. The method of claim 46 wherein X is OH.

48. The method of claim 47 wherein $R^{4-6}$ are independently selected from the group consisting of H, alkyl, and substituted alkyl wherein any two of $R^1$, $R^2$, $R^4$, $R^5$, or $R^6$ may be covalently linked.

49. The method of claim 1 wherein in T groups that contain —$CH_2$— groups one or more non-neighboring —$CH_2$— groups can be replaced with —O—; —S—; —NH—; —NH—CO—; —NR—, or —NR—CO—, where R is alkyl; —C=O; or —O—C=O.

50. The method of claim 1 wherein the T group is substituted with one or more groups selected from a halide; and acyl group; an OR or $N(R)_2$ group, where R is a hydrogen, an alkyl or aryl group; an SR' group, where R' is an alkyl, aryl group, a substituted alkyl group, or a substituted aryl group.

51. The method of claim 1 wherein the organoelectrophile is an aryl halide, a heteroaryl halide, or a substituted aryl halide.

52. The method of claim 51 wherein the organoelectrophile is an aryl iodide or a substituted aryl iodide.

53. The method of claim 1 wherein the organoelectrophile is an alkenyl halide or a substituted alkenyl halide.

54. The method of claim 1 wherein the organoelectrophile is an alkenyl iodide or a substituted alkenyl iodide.

55. The method of claim 1 wherein the activator anion is added as a salt of the activator anion.

56. The method of claim 55 wherein the salt of the activator anion is not a silver salt.

57. The method of claim 55 wherein the salt of the activator anion is not AgOTf, $AgBF_4$, or $AgNO_3$.

58. The method of claim 55 wherein the salt of the activator anion is not $Ag_2O$.

59. The method of claim 1 wherein the organosilicon reagent has the formula:

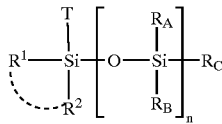

where n is an integer greater than or equal to 1; and $R_A$, $R_B$ and $R_C$, independently, are selected from the group consisting of an alkyl group, a substituted alkyl group, a halide, an OR or $NR^2$ group, where each R independently of other R groups is a hydrogen, an alkyl group or a substituted alkyl group, or any of $R_A$, $R_B$ or $R_C$ can be transferable groups, and wherein any two of $R_A$, $R_B$ and $R_C$ can be covalently linked.

60. The method of claim 1 wherein the organosilicon nucleophile is:

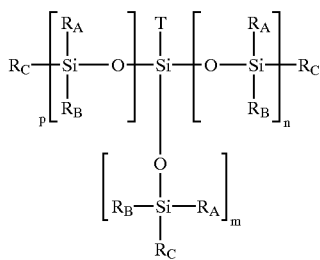

wherein n, m and p are zero or integers that are greater than or equal to 1 and wherein at least one of n, m or p is 1 or greater; and $R_A$, $R_B$ and $R_C$, independently, are selected from the group consisting of an alkyl group, a substituted alkyl group, a halide, an OR or $NR_2$ group, where each R independently of other R groups is a hydrogen, an alkyl group or a substituted alkyl group, or any of $R_A$, $R_B$ or $R_C$ can be transferable groups, and wherein any two of $R_A$, $R_B$ and $R_C$ can be covalently linked.

61. The method of claim 1 wherein the organosilicon nucleophile has the formula:

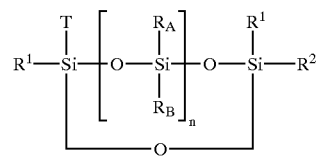

where n is an integer greater than or equal to 1, $R_A$ and $R_B$, independently, are selected from the group consisting of an alkyl group, a substituted alkyl group, a halide, an OR or $NR_2$ group, where each R independently of other R groups is a hydrogen, an alkyl group or a substituted alkyl group, or one or both or $R_A$ and $R_B$ can be transferable groups.

62. The method of claim 61 wherein the organosilicon nucleophile has the formula:

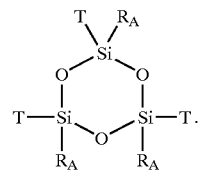

63. The method of claim 1 wherein the organosilicon reagent has the formula:

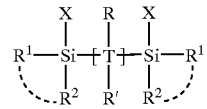

wherein R and R', independently, can be $R^1$, $R^2$ or X groups.

64. The method of claim 1 wherein the organosilicon reagent has the formula:

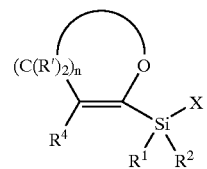

where n is 2–4.

65. The method of claim 1 wherein the organosilicon nucleophile has the formula:

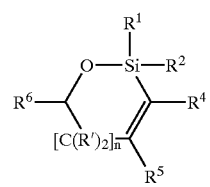

where n is 0, 1, 2, or 3, $R^1$ and $R^2$ independently are selected from alkyl or substituted alkyl groups, are $R^{4-6}$ selected from hydrogen, alkyl, substituted alkyl, alkoxy, aryl, substituted aryl, or heteroaromatic groups, and R' are independently selected from hydrogen, alkyl or substituted alkyl groups.

66. The method of claim 1 wherein the organosilicon nucleophile is a siloxane.

67. The method of claim 1 wherein the organosilicon nucleophile is a bis-silyl compound.

68. The method of claim 1 wherein the activator anion is a trialkyl silanolate.

69. The method of claim 1 wherein the activator anion is trimethyl silanolate.

70. The method of claim 1 wherein the activator anion is fluoride-free.

71. The method of claim 1 wherein the activator is a tetraalkylammonium fluoride, tetraalkylammonium hydroxide, or a tetraalkylammonium alkoxide.

72. The method of claim 1 wherein the activator is a tetrabutylammonium fluoride, tetrabutylammonium hydroxide, or a tetrabutylammonium alkoxide.

* * * * *